United States Patent
Matsushima et al.

(10) Patent No.: US 8,791,106 B2
(45) Date of Patent: Jul. 29, 2014

(54) FUSED RING PYRIDINE COMPOUND

(71) Applicant: Astellas Pharma Inc., Chuo-ku (JP)

(72) Inventors: Yuji Matsushima, Chuo-ku (JP);
Minoru Kameda, Chuo-ku (JP); Shugo Honda, Chuo-ku (JP); Yukihito Sugano, Chuo-ku (JP); Hiroyuki Usuda, Chuo-ku (JP); Tadashi Terasaka, Chuo-ku (JP); Takeshi Terasawa, Chuo-ku (JP); Fusako Nishigaki, Chuo-ku (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 13/753,005

(22) Filed: Jan. 29, 2013

(65) Prior Publication Data

US 2013/0143874 A1    Jun. 6, 2013

Related U.S. Application Data

(63) Continuation-in-part of application No. PCT/JP2011/067222, filed on Jul. 28, 2011.

(30) Foreign Application Priority Data

Jul. 29, 2010 (JP) .................. 2010-170338

(51) Int. Cl.
*A61K 31/54* (2006.01)
*C07D 417/00* (2006.01)

(52) U.S. Cl.
USPC .......................... 514/228.2; 544/62; 544/58.2

(58) Field of Classification Search
USPC ................... 514/228.2; 544/62, 58.2
See application file for complete search history.

(56) References Cited

U.S. PATENT DOCUMENTS

| | | | |
|---|---|---|---|
| 6,608,071 B2 * | 8/2003 | Altmann et al. ............... | 514/269 |
| 7,799,782 B2 * | 9/2010 | Munson et al. ............ | 514/234.5 |
| 2006/0247261 A1 | 11/2006 | Eatherton et al. | |
| 2006/0293354 A1 | 12/2006 | Eatherton et al. | |
| 2007/0219229 A1 | 9/2007 | Eatherton et al. | |
| 2008/0039464 A1 | 2/2008 | Berry et al. | |
| 2008/0200501 A1 | 8/2008 | Muthuppalaniappan et al. | |
| 2008/0221097 A1 | 9/2008 | Eatherton et al. | |
| 2009/0018114 A1 | 1/2009 | Carroll et al. | |
| 2009/0041722 A1 | 2/2009 | Liu et al. | |
| 2011/0071127 A1 | 3/2011 | Berry et al. | |

FOREIGN PATENT DOCUMENTS

| | | |
|---|---|---|
| WO | WO 2004/018433 | 3/2004 |
| WO | WO 2005/121140 | 12/2005 |
| WO | WO 2007/017237 | 2/2007 |
| WO | WO 2007/017264 | 2/2007 |
| WO | WO 2008/116816 | 10/2008 |

OTHER PUBLICATIONS

Altmann et al. CAS: 132: 166131, 2000.*
Giblin et al, "Discovery of 1-[4-(3-Chlorophenylamino)-1-methyl-1H-pyrrolo[3-2-c]pryidin-7-yl]-1-morpholin-4-ylmthanone (GSK554418A), a Brain Penetrant 5-Azaindole $CB_2$ Agonist for the Treatment of Chronic Pain", *J. Med. Chem.* 2009, 59, 5785-5788.
International Search Report issued Sep. 13, 2011, in International application No. PCT/JP2011/067222 (w/English translation).
International Preliminary Report on Patentability, issued Sep. 13, 2011, in International application No. PCT/JP2011/067222.
Extended European Search Report issued Dec. 5, 2013 in Patent Application No. 11812552.5.

* cited by examiner

*Primary Examiner* — Rei-tsang Shiao
(74) *Attorney, Agent, or Firm* — Oblon, Spivak, McClelland, Maier & Neustadt, L.L.P.

(57) ABSTRACT

[Problem] To provide a compound useful as a novel agent which is excellent in preventing and/or treating cannabinoid receptor type 2-related diseases, based on agonist action on a cannabinoid receptor type 2
[Means for Solution] The present inventors conducted thorough investigation regarding compounds having agonist action on a cannabinoid receptor type 2. They confirmed that the fused ring pyridine compound of the present invention has excellent agonist action on the cannabinoid receptor type 2, thereby completing the present invention. The fused ring pyridine compound of the present invention has agonist action on the cannabinoid receptor type 2, and can be used as an agent for preventing and/or treating cannabinoid receptor type 2-related diseases, for example, inflammatory diseases and pain.

20 Claims, No Drawings

FUSED RING PYRIDINE COMPOUND

CROSS REFERENCES TO RELATED APPLICATIONS

This application is a Continuation-in-Part of International Patent Application No. PCT/JP2011/067222, filed on Jul. 28, 2011, and claims priority to Japanese Patent Application No. 2010-170338, filed on Jul. 29, 2010.

TECHNICAL FIELD

The present invention relates to a pharmaceutical composition, particularly, to a fused ring pyridine compound that is useful as an active ingredient of a pharmaceutical composition for preventing and/or treating cannabinoid receptor type 2-related diseases.

BACKGROUND ART

Cannabinoid is a general term for marijuana components contained in *cannabis*. So far, about 60 kinds or more of the components are known, which mainly include tetrahydrocannabinol, cannabinol, cannabidiol, and the like. Marijuana has been used for thousands of years for medicines or the like, induces psychological and neural reactions, and causes sensory confusion, euphoria, analgesic action, hallucination, and the like. Cannabinoids have various types of pharmacological actions and have been found to have immunosuppressive action, anti-inflammatory action, analgesic action, and the like in addition to the action on the central nervous system.

A cannabinoid is a seven transmembrane G-protein coupled receptor, and so far, two types including cannabinoid receptors type 1 (CB1) and type 2 (CB2) have been identified and screened (Nature, 1990, 346, 561-564; Nature, 1993, 365, 61-65). Human CB1 is constituted with 472 amino acids, and highly expressed in the pallidum, corpus striatum, substantia nigra, hippocampus, the cerebellar molecular layer, the cerebral cortex, and the like in the brain. CB1 is also expressed in the testes, the deferent duct, the uterus, the small intestine, blood vessels, and the like, in addition to the brain. CB2 is constituted with 360 amino acids and exhibits 44% homology with CB1. CB2 is highly expressed in the spleen, the tonsils, and lymph nodes and further in leukocytic cells such as macrophages, monocytes, B-lymphocytes, NK cells, eosionophills and the like. Recently, it has been reported that CB2 is also expressed in the brain (Science, 2005, 310, 329-332).

A CB2 agonist has been reported to exhibit central analgesic action (European Journal of Neuroscience, 2006, 23, 1530-1538) and peripheral analgesic action (Proceedings of the National Academy of Sciences, 2005, 102, 3093-3098). In addition, it has been reported that since CB2 is highly expressed in hematocytes and immunocytes, a CB2 agonist exhibits immunosuppressive action and anti-inflammatory action (British Journal of Pharmacology, 2003, 139, 775-786). The CB2 agonist has been reported to have an antipruritic action in skin diseases (Science, 2007, 316, 1494-1497), and is expected to be applied to atopic dermatitis and the like. Moreover, due to its anti-inflammatory action and immunosuppressive action, the CB2 agonist is expected to be effective for atherosclerosis (Nature, 2005, 434, 782-786), reflux esophagitis (European Journal of Pharmacology, 2007, 573, 206-213), hepatic disorder (British Journal of Pharmacology, 2008, 153, 286-289), and chronic liver diseases (Expert Opinion of Therapeutic Targets, 2007, 11, 403-409). Furthermore, it has been reported that CB2 is also expressed in osteoblasts and osteoclasts, and that a CB2 agonist has an action of increasing the activity of osteoblasts and inhibiting the activity of the osteoclasts, thereby having an action of inhibiting osteoclasia (Proceedings of the National Academy of Sciences, 2006, 103, 696-701).

As compounds having CB2 agonist action, for example, the compounds represented by the following Formula (A) (Patent Document 1), Formula (B) (Patent Document 2), Formula (C) (Patent Documents 3 and 4), Formula (D) (Non-Patent Document 1), and Formula (E) (Patent Document 5) have been reported respectively. However, none of the above documents includes the disclosure or implication about a compound of Formula (I) described later or a salt thereof according to the present invention,

[Chem. 1]

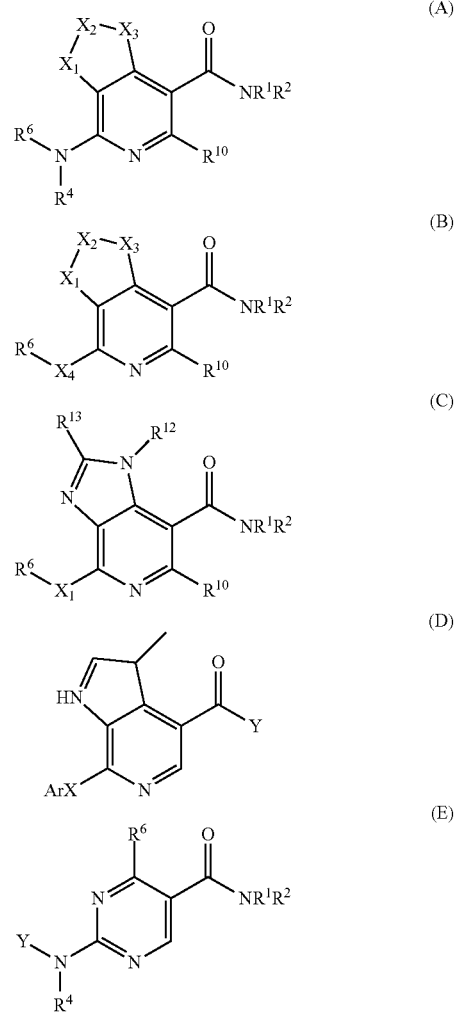

(in the Formulae (A) and (B), $X_1$ particularly represents $NR^{12}$; $X_2$ and $X_3$ represent a —$CR^{13}$=$CR^{11}$— group in combination, or $X_3$ represents $NR^{12}$; $X_1$ and $X_2$ represent a —$CR^{13}$=$CR^{11}$— group in combination, see the corresponding gazettes for detail, see the corresponding gazette for Formula (C), and see the corresponding gazette for Formula (D), in Formula (E), $R^6$ represents methyl, chloro, or $CH_xF_n$, see the corresponding gazette for detail).

RELATED ART

Patent Document

Patent Document 1: Pamphlet of International Publication WO 2005/121140
Patent Document 2: Pamphlet of International Publication WO 2007/017264
Patent Document 3: Pamphlet of International Publication WO 2007/017237
Patent Document 4: Pamphlet of International Publication WO 2008/116816
Patent Document 5: Pamphlet of International Publication WO 2004/018433

Non-Patent Document

Non-Patent Document 1: Journal of Medicinal Chemistry, 2009, Vol. 52, No. 19, pp 5785-5788

DISCLOSURE OF INVENTION

Problems to Be Solved by the Invention

The present invention provides a pharmaceutical composition, for example, a pharmaceutical composition having a CB2 agonist action, particularly, a pharmaceutical composition for preventing and/or treating CB2-related diseases and a compound useful as an active ingredient of the pharmaceutical composition.

Means for Solving the Problems

The present inventors conducted thorough research regarding a CB2 agonist. As a result, they found that a fused ring pyridine compound shown below has excellent CB2 agonist action and can be an agent for preventing and/or treating CB2-related diseases, thereby completing the present invention.

That is, the present invention relates to a compound of Formula (I) or a salt thereof, and to a pharmaceutical composition containing the compound or a salt thereof and an excipient,

[Chem. 2]

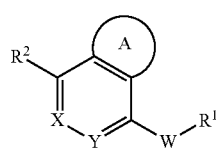

(I)

(in the formula,
X and Y represent CH, C-lower alkyl, or N, in which either X or Y represents N,
W represents —NH—, —N(lower alkyl)-, —O—, —S—, —S(O)—, or —S(O)$_2$—,
R$^1$ represents cycloalkyl which may be substituted, aryl which may be substituted, an aromatic heterocycle which may be substituted, or a non-aromatic heterocycle which may be substituted,
R$^2$ represents —Z—NR$^3$R$^4$ or —Z-cyclic amino which may be substituted,
A portion represents a group represented by Formula (II), (III), or (IV),

[Chem. 3]

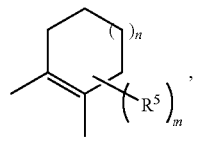

(II)

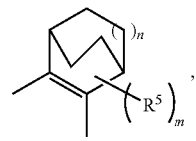

(III)

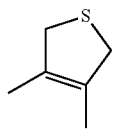

(IV)

R$^3$ represents H or lower alkyl,
R$^4$ represents lower alkyl substituted with one or more groups selected from the group consisting of —OH, —O-lower alkyl, halogen, cycloalkyl, cyano, —S-lower alkyl, —S(O)-lower alkyl, —S(O)$_2$-lower alkyl, and —O-halogeno-lower alkyl,
R$^5$'s are the same as or different from each other and represent lower alkyl or halogen,
Z's are the same as or different from each other and represent —C(O)—, —CH$_2$—, or —S(O)$_2$—,
m's are the same as or different from each other and represent an integer of 0 to 10, and
n's are the same as or different from each other and represent an integer of 0 to 2).

In addition, unless otherwise specified, if symbols in a chemical formula in the present specification are also used in another chemical formula, the same symbols have the same definition.

Moreover, the present invention relates to a pharmaceutical composition for preventing and/or treating CB2-related diseases that contains the compound of Formula (I) or a salt thereof. In addition, the pharmaceutical composition includes an agent for preventing and/or treating CB2-related diseases that contains the compound of Formula (I) or a salt thereof.

The present invention also relates to the use of the compound of Formula (I) or a salt thereof for manufacturing a pharmaceutical composition for preventing and/or treating CB2-related diseases, the use of the compound of Formula (I) or a salt thereof for preventing and/or treating CB2-related diseases, the compound of Formula (I) or a salt thereof for preventing and/or treating CB2-related diseases, and a method of preventing and/or treating CB2-related diseases that includes administering an effective amount of the compound of Formula (I) or a salt thereof to a subject. In addition, the "subject" refers to a human being or other mammals that require the prevention or treatment, and as another embodiment, the subject refers to a human being who requires the prevention or treatment.

Effects of the Invention

The compound of Formula (I) or a salt thereof has CB2 agonist action, and can be used as an agent for preventing and/or treating CB2-related diseases.

Examples of the CB2-related diseases include inflammatory diseases (for example, rheumatoid arthritis and arthritis deformans), pain (for example, acute pain, chronic pain, nociceptive pain, inflammatory pain, pain of rheumatoid arthropathy, and pain of arthrosis deformans), cancer and tumors (for example, cancer in the immune system, lung cancer, colorectal cancer, and leukemia), respiratory diseases (for example, respiratory distress syndrome, pulmonary tuberculosis, asthma, and chronic obstructive pulmonary disease), liver diseases, brain diseases, eye diseases (for example, ocular hypertension, cataracts, glaucoma, and retinal diseases), skin diseases (for example, pruritic dermatitis and mycosis on the skin surface), circulatory diseases (for example, angina pectoris, myocardial infarction, arteriosclerosis, hypertension, restenosis after coronary stenting, and thrombosis), allergic diseases (for example, anaphylaxis, allergic asthma, atopic asthma, and drug allergies), digestive diseases (for example, constipation, diarrhea, vomiting, peptic ulcer, irritable bowel syndrome, and ulcerative colitis), immunologic diseases (for example, immunological incompetence, psoriasis, rheumatoid arthritis, osteoporosis, sepsis, and systemic lupus erythematosus), neurogenic diseases (for example, neurodegenerative diseases, nausea, neuropathy, dementia, Parkinson's disease, schizophrenic disorder, obsessive-compulsive disorder, post-traumatic stress disorder, memory disorder, lack of appetite, anorexia, circadian dysrhythmia, sleep apnea, drug dependence, dyskinesia, convulsions, and paresthesia), osteogenesis, bone reconstruction, obesity, and the like.

EMBODIMENTS FOR CARRYING OUT THE INVENTION

Hereinafter, the present invention will be described in detail.

"Lower alkyl" refers to linear or branched alkyl having 1 to 6 carbon atoms (hereinafter, abbreviated to $C_{1-6}$), for example, methyl, ethyl, n-propyl, isopropyl, n-butyl, isobutyl, sec-butyl, tert-butyl, n-pentyl, n-hexyl and the like. As another embodiment, the lower alkyl is $C_{1-4}$ alkyl, and as still another embodiment, the lower alkyl is methyl, ethyl, or n-propyl.

"Lower alkylene" refers to linear or branched $C_{1-6}$ alkylene, for example, methylene, ethylene, trimethylene, tetramethylene, pentamethylene, hexamethylene, propylene, butylene, methyl methylene, ethyl ethylene, 1,1dimethylethylene, 2,2-dimethylethylene, 1,2-dimethylethylene, 1,1,2,2-tetramethylethylene, 1-methylbutylene and the like. As another embodiment, the lower alkylene is $C_{1-4}$ alkylene, and as still another embodiment, the lower alkylene is methylene, ethylene, trimethylene, tetramethylene, pentamethylene, or 1,2-dimethylethylene.

"Halogen" refers to F, Cl, Br, and I. As another embodiment, the halogen is F or Cl, and as still another embodiment, the halogen is F, and as another embodiment, the halogen is Cl.

"Halogeno-lower alkyl" refers to lower alkyl substituted with one or more halogen atoms. As another embodiment, the halogeno-lower alkyl is lower alkyl substituted with 1 to 5 halogen atoms, and as still another embodiment, the halogeno-lower alkyl is trifluoromethyl.

"Cycloalkyl" refers to a $C_{3-10}$ saturated hydrocarbon ring group. The cycloalkyl may have a bridge. Alternatively, a portion of bonds of the ring may be unsaturated or fused with a benzene ring. Examples of the cycloalkyl include cyclopropyl, cyclobutyl, cyclopentyl, cyclohexyl, cyclohexenyl, cycloheptyl, cyclooctyl, bicyclo[2.2.1]heptyl, bicyclo[2.2.2]octyl, bicyclo[3.2.1]octyl, adamantyl, indanyl, and the like.

As another embodiment, the cycloalkyl is cyclopentyl, cyclohexyl, cycloheptyl, cyclooctyl, bicyclo[2.2.1]heptyl, bicyclo[2.2.2]octyl, bicyclo[3.2.1]octyl, or adamantyl, and as still another embodiment, the cycloalkyl is $C_{3-8}$ cycloalkyl. As another embodiment, the cycloalkyl is $C_{5-8}$ cycloalkyl, as another embodiment, the cycloalkyl is cyclohexyl, and as another embodiment, the cycloalkyl is adamantyl.

"Aryl" refers to a monocyclic to tricyclic $C_{6-14}$ aromatic hydrocarbon ring group, for example, phenyl, naphthyl and the like. As another embodiment, the aryl is a monocyclic to bicyclic $C_{6-10}$ aromatic hydrocarbon ring group, and as still another embodiment, the aryl is a monocyclic $C_{6-8}$ aromatic hydrocarbon ring group. As another embodiment, the aryl is phenyl, and as still another embodiment, the aryl is naphthyl.

An "aromatic heterocycle" refers to a 5- to 6-membered aromatic heterocycle that contains one or more hetero atoms selected from O, N, and S as ring-constituting atoms. The aromatic heterocycle may be fused with a benzene ring or a thiophene ring. Examples of the aromatic heterocycle include pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isoxazolyl, thiadiazolyl, oxadiazolyl, thienyl, furyl, indolyl, isoindolyl, benzimidazolyl, indazolyl, quinolyl, isoquinolyl, quinazolinyl, quinoxalinyl, phthalazinyl, benzothiazolyl, benzisothiazolyl, benzothiadiazolyl, benzoxazolyl, benzisoxazolyl, benzofuranyl, benzothienyl, carbazolyl, dibenzo[b,d]furanyl, dibenzo[b,d]thienyl, thienopyridyl, thienopyrimidinyl, thienopyrazyl, and the like. As another embodiment, the aromatic heterocycle is a 5- to 6-membered monocyclic aromatic heterocycle, and as still another embodiment, the aromatic heterocycle is a 6-membered monocyclic aromatic heterocycle. As another embodiment, the aromatic heterocycle is pyridyl, pyrrolyl, pyrazinyl, pyrimidinyl, pyridazinyl, imidazolyl, or triazolyl, and as still another embodiment, the aromatic heterocycle is pyridyl.

A "non-aromatic heterocycle" refers to a 4- to 7-membered non-aromatic heterocycle that contains one or more hetero atoms selected from O, N, and S as ring-constituting atoms. In addition, a sulfur atom as a ring-constituting atom may be oxidized. Examples of the non-aromatic heterocycle include azetidinyl, pyrrolidinyl, piperidinyl, piperazinyl, azepanyl, diazepanyl, morpholinyl, thiomorpholinyl, 1,1-dioxidothiomorpholinyl, tetrahydropyridinyl, oxetanyl, tetrahydrofuranyl, tetrahydrothienyl, tetrahydropyranyl, dioxolanyl, dioxanyl, or tetrahydrothiopyranyl, and the like. As another embodiment, the non-aromatic heterocycle is a 5- to 6-membered monocyclic non-aromatic heterocycle, and as still another embodiment, the non-aromatic heterocycle is a 6-membered monocyclic non-aromatic heterocycle. As another embodiment, the non-aromatic heterocycle is piperidinyl, morpholinyl, thiomorpholinyl, 1,1-dioxidothiomorpholinyl, tetrahydrofuranyl, tetrahydropyranyl, or tetrahydrothiopyranyl, and as still another embodiment, the non-aromatic heterocycle is piperidinyl, morpholinyl, 1,1-dioxidothiomorpholinyl, or tetrahydropyranyl.

"Cyclic amino" refers to a group having a nitrogen atom among the above "non-aromatic heterocycles", and is a non-aromatic heterocycle having a bond on the nitrogen atom. Examples of the cyclic amino include azetidin-1-yl, pyrazolidin-1-yl, imidazolidin-1-yl, 1,4-diazepan-1-yl, 3-azabicyclo[3.1.1]hepto-3-yl, 2-azabicyclo[2.2.2]octo-2-yl, pyrrolidin-1-yl, piperidin-1-yl, azepan-1-yl, piperazin-1-yl, morpholin-4-yl, thiomorpholin-4-yl, 1-oxidothiomorpholin-4-yl, 1,1-dioxidothiomorpholin-4-yl, 1,3-thiadian-3-yl, 1-oxido-1,3-thiadian-3-yl, 1,1-dioxido-1,3-thiadian-3-yl, 1,4-oxaazepan-4-yl, and the like. As another embodiment, the cyclic amino is pyrrolidin-1-yl, piperidin-1-yl, azepan-1-yl, piperazin-1-yl, morpholin-4-yl, thiomorpholin-4-yl, 1,1-dioxidothiomorpholin-4-yl, or 1,4-oxaazepan-4-yl, and as still another embodiment, the cyclic amino is pyrrolidin-1-yl, piperidin-1-yl, morpholin-4-yl, 1,1-dioxidothiomorpholin-4-yl, or 1,4-oxaazepan-4-yl. As still another embodiment, the cyclic amino is 6-membered monocyclic cyclic amino. As another embodiment, the cyclic amino is piperidin-1-yl, morpholin-4-yl, or 1,1-dioxidothiomorpholin-4-yl.

In the present specification, the phrase "may be substituted" means that a group may be unsubstituted or have one to five substituents. As another embodiment, the phrase means that a group may be unsubstituted or have one to three substituents, and as still another embodiment, the phrase means that a group may be unsubstituted or have one substituent. As another embodiment, the phrase means that a group may be unsubstituted. In addition, when a group has a plurality of substituents, these substituents may be the same as or different from each other.

In Formula (I), as substituents acceptable in the "cycloalkyl which may be substituted", "aryl which may be substituted", "aromatic heterocycle which may be substituted", and "non-aromatic heterocycle which may be substituted" represented by $R^1$, and in the "cyclic amino which may be substituted" in the "—Z-cyclic amino which may be substituted" represented by $R^2$, generally used substituents can be used. Examples thereof include substituents of the following D group.

D group
(1) halogen,
(2) —OH, —O-lower alkyl, —O-halogeno-lower alkyl, and —SH,
(3) cyano and nitro,
(4) cycloalkyl, —O-cycloalkyl, and —C(O)-cycloalkyl which may be respectively substituted with one or more groups selected from the group consisting of lower alkyl, halogen, —OH, —O-lower alkyl, —O-halogeno-lower alkyl, and halogeno-lower alkyl,
(5) aryl, —O-aryl, and —C(O)-aryl which may be respectively substituted with one or more groups selected from the group consisting of lower alkyl, halogen, —OH, —O-lower alkyl, —O-halogeno-lower alkyl, and halogeno-lower alkyl,
(6) an aromatic heterocycle, an —O-aromatic heterocycle, and —C(O)-aromatic heterocycle which may be respectively substituted with one or more groups selected from the group consisting of lower alkyl, halogen, —OH, —O-lower alkyl, —O-halogeno-lower alkyl, and halogeno-lower alkyl,
(7) a non-aromatic heterocycle, an —O-non-aromatic heterocycle, and a —C(O)-non-aromatic heterocycle which may be respectively substituted with one or more groups selected from the group consisting of lower alkyl, halogen, —OH, —O-lower alkyl, —O-halogeno-lower alkyl, and halogeno-lower alkyl,
(8) —C(O)-lower alkyl, —C(O)O-lower alkyl, —NH—C(O)-lower alkyl, —NH-lower alkyl, —N(lower alkyl)$_2$, —C(O)—NH-lower alkyl, and —C(O)—N(lower alkyl)$_2$, in which lower alkyl moieties may be respectively substituted with one or more groups selected from the group consisting of halogen, —OH, —O-lower alkyl, and —O-halogeno-lower alkyl,
(9) —NH$_2$ and —C(O)—NH$_2$,
(10) —S-lower alkyl, —S(O)-lower alkyl, and —S(O)$_2$-lower alkyl, in which lower alkyl moieties may be respectively substituted with one or more groups selected from the group consisting of halogen, —OH, —O-lower alkyl, and —O-halogeno-lower alkyl, and
(11) lower alkyl and —O-lower alkyl which may be respectively substituted with one or more groups selected from the group consisting of the substituents described in the above sections (1) to (10).

As an embodiment, D group includes
(1) halogen,
(2) —OH, —O-lower alkyl, and —O-halogeno-lower alkyl,
(3) cyano and nitro,
(4) cycloalkyl and —O-cycloalkyl which may be respectively substituted with one or more groups selected from the group consisting of lower alkyl, halogen, —OH, —O-lower alkyl, —O-halogeno-lower alkyl, and halogeno-lower alkyl,
(5) aryl, —O-aryl, and —C(O)-aryl which may be respectively substituted with one or more groups selected from the group consisting of lower alkyl, halogen, —OH, —O-lower alkyl, —O-halogeno-lower alkyl, and halogeno-lower alkyl,
(6) —C(O)-lower alkyl and —C(O)O-lower alkyl in which a lower alkyl moiety may be respectively substituted with one or more groups selected from the group consisting of halogen, —OH, —O-lower alkyl, and —O-halogeno-lower alkyl,
(7) —S-lower alkyl, —S(O)-lower alkyl, and —S(O)$_2$-lower alkyl in which a lower alkyl moieties may be respectively substituted with one or more groups selected from the group consisting of halogen, —OH, —O-lower alkyl, and —O-halogeno-lower alkyl, and
(8) lower alkyl and —O-lower alkyl which may be respectively substituted with one or more groups selected from the group consisting of the substituents described in the above sections (1) to (7).

As another embodiment, D group includes
(1) halogen,
(2) —OH,
(3) cyano,
(4) —S-lower alkyl, —S(O)-lower alkyl, and —S(O)$_2$-lower alkyl, in which a lower alkyl moieties may be respectively substituted with one or more groups selected from the group consisting of halogen, —OH, —O-lower alkyl, and —O-halogeno-lower alkyl, and
(5) lower alkyl and —O-lower alkyl which may be respectively substituted with one or more groups selected from the group consisting of the substituents described in the above sections (1) to (4).

As another embodiment of substituents in the "cycloalkyl which may be substituted", "aromatic heterocycle which may be substituted", and "non-aromatic heterocycle which may be substituted" represented by $R^1$ in Formula (I), i) lower alkyl which may be substituted with one or more groups selected from the group consisting of halogen, OH, and —O-lower alkyl, ii) halogen, iii) nitro, and iv) —OH are exemplified. As still another embodiment, one or more groups selected from the group consisting of lower alkyl, halogen, and —OH are exemplified, and as another embodiment, one or more groups selected from methyl, F, Cl, and —OH are exemplified.

As another embodiment of the substituents acceptable in the "aryl which may be substituted" in Formula (I),
(1) lower alkyl or —O-lower alkyl which may be respectively substituted with one or more groups selected from the group consisting of halogen, —OH, —O-lower alkyl, and aryl,
(2) halogen,
(3) —OH,
(4) cyano,
(5) cycloalkyl or —O-cycloalkyl which may be respectively substituted with lower alkyl,
(6) aryl, —O-aryl, or —C(O)-aryl which may be respectively substituted with a group selected from the group consisting of lower alkyl, halogen, —OH, —O-lower alkyl, —O-(halogeno-lower alkyl), and halogeno-lower alkyl, (7) an aromatic heterocycle or an —O-aromatic heterocycle which may be respectively substituted with one or more groups selected from the group consisting of lower alkyl and halogen, (8) a non-aromatic heterocycle or an —O-non-aromatic heterocycle which may be respectively substituted with one or more groups selected from the group consisting of lower alkyl and halogen, (9) —C(O)-lower alkyl, —C(O)O-lower alkyl, —NH—C(O)-lower alkyl, or -lower alkylene-C(O)O-lower alkyl, in which a lower alkyl moieties may be respectively substituted with one or more groups selected from the group consisting of halogen and —OH,

(10) —$NH_2$, —NH-lower alkyl, or —N(lower alkyl)$_2$, and

(11) —S-lower alkyl, —S(O)-lower alkyl, or —S(O)$_2$-lower alkyl can be exemplified.

Some embodiments of the compound of Formula (I) or a salt thereof will be shown below.

(1) A compound or a salt thereof in which either X or Y represents CH or a salt thereof; as another embodiment, a compound in which X represents CH and Y represents N; as still another embodiment, a compound or a salt thereof in which X represents N and Y represents CH or a salt thereof;

(2) a compound or a salt thereof in which A portion is represented by Formula (II) or (III); as another embodiment, a compound or a salt thereof in which A portion is represented by Formula (II); as still another embodiment, a compound or a salt thereof in which A portion is represented by Formula (III);

(3) a compound or a salt thereof in which n in Formula (II) represents 0 or 1; as another embodiment, a compound or a salt thereof in which n in Formula (II) represents 1;

(4) a compound or a salt thereof in which n in Formula (III) represents 0 or 1; as another embodiment, a compound or a salt thereof in which n in Formula (III) represents 0; as still another embodiment, a compound or a salt thereof in which n in Formula (III) represents 1;

(5) a compound or a salt thereof in which W represents —NH—, —O—, —S—, or —S(O)$_2$—; as another embodiment, a compound or a salt thereof in which W represents —NH—, —O—, or —S—; as still another embodiment, a compound or a salt thereof in which W represents —NH—, —O—, or —S(O)$_2$—; as another embodiment, a compound or a salt thereof in which W represents —NH— or —O—; as another embodiment, a compound or a salt thereof in which W represents —NH— or —S—; as another embodiment, a compound or a salt thereof in which W represents —NH— or —S(O)$_2$—; as another embodiment, a compound or a salt thereof in which W represents —NH—; as another embodiment, a compound or a salt thereof in which W represents —O—; as another embodiment, a compound or a salt thereof in which W represents —S(O)$_2$—;

(6) a compound or a salt thereof in which $R^1$ represents cycloalkyl, aryl, an aromatic heterocycle, and a non-aromatic heterocycle which may be respectively substituted with one or more groups selected from D group; as another embodiment, a compound or a salt thereof in which $R^1$ represents i) cycloalkyl which may be substituted with one or more groups selected from the group consisting of lower alkyl, halogen, and —OH, ii) aryl which may be substituted with one or more groups selected from the group consisting of lower alkyl, halogen, halogeno-lower alkyl, —O-lower alkyl, —O-halogeno-lower alkyl, —S-lower alkyl, —S(O)-lower alkyl, —S(O)$_2$-lower alkyl, cyano, —C(O)-lower alkyl, —C(O)O-lower alkyl, —$NH_2$, —NH-lower alkyl, and —N(lower alkyl)$_2$, iii) an aromatic heterocycle which may be substituted with one or more groups selected from the group consisting of lower alkyl, halogen, and —OH, or iv) a non-aromatic heterocycle which may be substituted with one or more groups selected from the group consisting of lower alkyl, halogen, and —OH; as still another embodiment, a compound or a salt thereof in which $R^1$ represents i) cycloalkyl which may be substituted with one or more groups selected from the group consisting of lower alkyl, halogen and —OH, or ii) aryl which may be substituted with one or more groups selected from the group consisting of lower alkyl, halogen, halogeno-lower alkyl, —O-lower alkyl, —O-halogeno-lower alkyl, —S-lower alkyl, —S(O)-lower alkyl, —S(O)$_2$-lower alkyl, cyano, —C(O)-lower alkyl, —C(O)O-lower alkyl, —$NH_2$, —NH-lower alkyl, and —N(lower alkyl)$_2$; as another embodiment, a compound or a salt thereof in which $R^1$ represents i) cycloalkyl which may be substituted with one or more groups selected from the group consisting of lower alkyl, halogen, and —OH, or ii) aryl which may be substituted with one or more groups selected from the group consisting of lower alkyl, halogen, halogeno-lower alkyl, cyano, —S(O)$_2$-lower alkyl, and —O-halogeno-lower alkyl;

(7) a compound or a salt thereof in which $R^2$ represents —Z—$NR^3R^4$ or —Z-cyclic amino which may be substituted with one or more groups selected from the group consisting of D group; as another embodiment, a compound or a salt thereof in which $R^2$ represents —Z-cyclic amino which may be substituted with one or more groups selected from D group; as still another embodiment, a compound or a salt thereof in which $R^2$ represents a group represented by Formula (V), (VI) or (VII); as another embodiment, a compound or a salt thereof in which $R^2$ represents Formula (V) or (VI); as another embodiment, a compound or a salt thereof in which $R^2$ represents a group represented by Formula (V); as another embodiment a compound or a salt thereof in which $R^2$ represents a group represented by Formula (VI); and as another embodiment, a compound or a salt thereof in which $R^2$ represents a group represented by Formula (VII)

[Chem. 4]

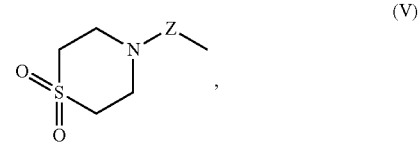
(V)

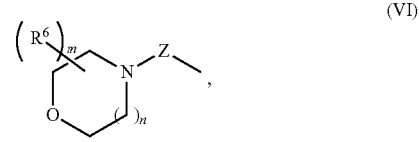
(VI)

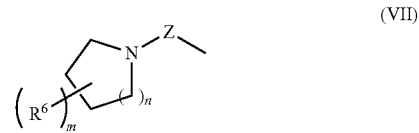
(VII)

(in the formula, $R^6$'s are the same as or different from each other and represent lower alkyl, which may be substituted with one or more groups selected from —OH, —O-lower alkyl, halogen, cycloalkyl, cyano, —S-lower alkyl, —S(O)-lower alkyl, —S(O)$_2$-lower alkyl, and —O-halogeno-lower alkyl, —OH, —O-lower alkyl, halogen, cycloalkyl, cyano, —O-lower alkylene-OH, —S-lower alkyl, —S(O)-lower alkyl, —S(O)$_2$-lower alkyl, or —O-halogeno-lower alkyl);

(8) a compound or a salt thereof in which $R^6$ in Formula (VI) represents -lower alkylene-OH; as another embodiment, a compound or a salt thereof in which $R^6$ in Formula (VI) represents $C_{1-4}$ alkylene-OH;

(9) a compound or a salt thereof in which $R^6$ in Formula (VII) represents halogen or —OH;

(10) a compound or a salt thereof in which m in $(R^5)$m in Formula (II) represents 0, or $R^5$ represents lower alkyl when m represents 1 or 2; as another embodiment, a compound or a salt thereof in which m in $(R^5)$m in Formula (II) represents 0;

(11) a compound or a salt thereof in which m in Formula (III) represents 0, or m represents 1 or 2 and $R^5$ represents lower alkyl; as another embodiment, a compound or a salt thereof in which m in Formula (III) represents 0;

(12) a compound or a salt thereof in which Z represents —C(O)— or —CH$_2$—; as another embodiment, a compound or a salt thereof in which Z represents —C(O)—; as still another embodiment, a compound or a salt thereof in which Z represents —CH$_2$—;

(13) a compound in which n in Formula (VI) represents 1 or 2 or a salt thereof, as another embodiment, a compound in which n in Formula (VI) represents 1 or a salt thereof;

(14) a compound or a salt thereof in which m in Formula (VI) represents 0 or 1; as another embodiment, a compound or a salt thereof in which m in Formula (VI) represents 0;

(15) a compound or a salt thereof in which n in Formula (VII) represents 1 or 2; as another embodiment, a compound or a salt thereof in which n in Formula (VII) represents 2;

(16) a compound or a salt thereof which is a combination of two or more embodiments described in the above sections (1) to (15)

As described in the above section (16), the present invention includes a compound or a salt thereof which is a combination of two or more embodiments described in the above sections (1) to (15). As specific examples thereof, the following embodiments are also exemplified.

(17) A compound or a salt thereof in which X and Y represent CH, C-lower alkyl, or N; in which either X or Y represents N, W represents —NH—, —N(lower alkyl)-, —O—, —S—, —S(O)— or —S(O)$_2$—

$R^1$ represents cycloalkyl which may be substituted, aryl which may be substituted, an aromatic heterocyclic group which may be substituted, or a non-aromatic heterocyclic group which may be substituted, $R^2$ represents —C(O)—NR$^3$R$^4$ or a group selected from Formulae (V), (VI), and (VII), A portion represents a group selected from Formulae (II), (III), and (IV), $R^3$ represents H or lower alkyl, $R^4$ represents -lower alkylene-OH, -lower alkylene-O-lower alkyl, or -lower alkylene-S(O)$_2$-lower alkyl, $R^5$'s are the same as or different from each other and represent lower alkyl or halogen, $R^6$'s are the same as or different from each other and represent lower alkyl, halogen, —OH, or lower alkylene-OH, Z's are the same as or different from each other and represent —C(O)—, —CH$_2$—, or —S(O)$_2$— m represents an integer of 0 to 4, and n represents an integer of 0 to 2.

(18) a compound or a salt thereof in which $R^1$ represents cycloalkyl, aryl, an aromatic heterocycle, or a non-aromatic heterocycle which may be respectively substituted with one or more substituents selected from D group, $R^2$ represents —Z—NR$^3$R$^4$ or —Z-cyclic amino which may be substituted with one or more substituents selected from D group,

(19) the compound or a salt thereof according to section (18) in which $R^2$ represents a group represented by Formula (V), (VI), or (VII), $R^6$'s are the same as or different from each other and represent lower alkyl which may be substituted with one or more substituents selected from —OH, —O-lower alkyl, halogen, cycloalkyl, cyano, —S-lower alkyl, —S(O)-lower alkyl, —S(O)$_2$-lower alkyl, and —O-halogeno-lower alkyl, —OH, —O-lower alkyl, halogen, cycloalkyl, cyano, —O-lower alkylene-OH, —S-lower alkyl, —S(O)-lower alkyl, —S(O)$_2$-lower alkyl, or —O-halogeno-lower alkyl,

(20) the compound or a salt thereof according to section (19) in which $R^2$ represents a group represented by Formula (V) or (VI), Z represents —C(O)—, W represents —NH or —O—, and A portion represents a group represented by Formula (II) or (III),

(21) the compound or a salt thereof according to section (20) in which X represents CH, Y represents N, $R^1$ represents i) cycloalkyl which may be substituted with one or more groups selected from the group consisting of lower alkyl, halogen, and OH, or ii) aryl which may be substituted with one or more groups selected from the group consisting of lower alkyl, halogen, halogeno-lower alkyl, and —O-halogeno-lower alkyl, A portion represents a group represented by Formula (II) in which n represents 0 or 1 and m represents 0, n in Formula (VI) represents 1 or 2, and m in Formula (VI) represents 0,

(22) the compound or a salt thereof according to section (21) in which n in Formula (II) represents 0, n in Formula (VI) represents 1, $R^1$ represents phenyl which may be substituted with one or more groups selected from the group consisting of halogen, —O-halogeno-lower alkyl, and halogeno-lower alkyl,

(23) the compound or a salt thereof according to section (20) in which X represents CH, Y represents N, $R^1$ represents i) cycloalkyl which may be substituted with one or more groups selected from the group consisting of lower alkyl, halogen, and OH, ii) aryl which may be substituted with one or more groups selected from the group consisting of lower alkyl, halogen, halogeno-lower alkyl, —O-lower alkyl, and —O— halogeno-lower alkyl, or iii) a non-aromatic heterocycle which may be substituted with one or more groups selected from the group consisting of lower alkyl, halogen, and —OH, A portion represents a group represented by Formula (III) in which, n represents 0 or 1 and m represents 0, n in Formula (VI) represents 1 or 2, and m in Formula (VI) represents 0,

(24) the compound or a salt thereof according to section (23) in which $R^1$ represents phenyl which may be substituted with one or more groups selected from the group consisting of halogen, —O-halogeno-lower alkyl, and halogeno-lower alkyl, $R^2$ represents a group represented by Formula (V), and W represents —NH—,

(25) the compound or a salt thereof according to section (20) in which X represents N, Y represents CH, $R^1$ represents i) cycloalkyl which may be substituted with one or more groups selected from the group consisting of lower alkyl, halogen, and —OH, or ii) aryl which may be substituted with one or more groups selected from the group consisting of lower alkyl, halogen, halogeno-lower alkyl, and —O-halogeno-lower alkyl, A portion represents a group represented by Formula (II) in which n represents 1 and m represents 0, n in Formula (VI) represents 1, and m in Formula (VI) represents 0,

(26) the compound or a salt thereof according to section (25) in which $R^1$ represents phenyl which may be substituted with one or more groups selected from the group consisting of halogen and halogeno-lower alkyl, Z represents —C(O)—, $R^2$ represents Formula (V),

(27) the compound or a salt thereof according to section (20) in which X represents N, Y represents CH, $R^1$ represents i) cycloalkyl which may be substituted with one or more groups selected from the group consisting of lower alkyl, halogen, and OH, or ii) aryl which may be substituted with one or more groups selected from the group consisting of lower alkyl, halogen, halogeno-lower alkyl, —O-lower alkyl, —O-halogeno-lower alkyl, —S-lower alkyl, —S(O)-lower alkyl, —S(O)$_2$-lower alkyl, cyano, —C(O)-lower alkyl, —C(O)O-lower alkyl, NH$_2$, —NH-lower alkyl, and —N(lower alkyl)$_2$, A portion represents a group represented by Formula (III) in which n represents 0 or 1, and m represents 0, n in Formula (VI) represents 1, $R^6$ in Formula (VI) represents -lower alkylene-OH, and m in Formula (VI) represents 0 or 1,

(28) the compound or a salt thereof according to section (27) in which n in Formula (III) represents 1, $R^1$ represents phenyl which may be substituted with one or more groups selected from the group consisting of lower alkyl, halogen, and —O-halogeno-lower alkyl, and $R^2$ represents Formula (V), Examples of specific compounds included in the compound of Formula (I) or a salt thereof include the following:

{1-[(3-chlorophenyl)amino]-5,6,7,8-tetrahydroisoquinolin-4-yl}(1,1-dioxidothiomorpholin-4-yl)methanone, {4-[(3-chlorophenyl)amino]-5,6,7,8-tetrahydroisoquinolin-1-yl}(1,1-dioxidothiomorpholoin-4-yl)methanone, morpholin-4-yl(1-{[3-(trifluoromethoxy)phenyl]amino}-5,6,7,8-tetrahydroisoquinolin-4-yl)methanone, (1,1-dioxidothiomorpholin-4-yl){4-[3-(trifluoromethyl)phenoxy]-5,6,7,8-tetrahydroisoquinolin-1-yl}methanone, (1,1-dioxidothiomorpholin-4-yl)(4-{[3-(trifluoromethyl)phenyl]amino}-5,6,7,8-tetrahydroisoquinolin-1-yl)methanone, (1,1-dioxidothiomorpholin-4-yl){1-[3-(trifluoromethyl)phenoxy]-5,6,7,8-tetrahydroisoquinolin-4-yl}methanone, {4-[(3-chlorophenyl)amino]-5,6,7,8-tetrahydro-5,8-ethanoisoquinolin-1-yl}(1,1-dioxidothiomorpholin-4-yl)methanone, {1-[(3-chlorophenyl)amino]-5,6,7,8-tetrahydro-5,8-ethanoisoquinolin-4-yl}(1,1-dioxidothiomorpholin-4-yl)methanone, (1,1-dioxidothiomorpholin-4-yl)(1-{[3-(trifluoromethyl)phenyl]amino}-5,6,7,8-tetrahydro-5,8-ethanoisoquinolin-4-yl)methanone, (1,1-dioxidothiomorpholin-4-yl)(4-{[3-(trifluoromethoxy)phenyl]amino}-5,6,7,8-tetrahydro-5,8-ethanoisoquinolin-1-yl)methanone, {4-[(3,4-difluorophenyl)amino]-5,6,7,8-tetrahydro-5,8-ethanoisoquinolin-1-yl}(1,1-dioxidothiomorpholin-4-yl)methanone, {1-[(3-chloro-4-fluorophenyl)amino]-5,6,7,8-tetrahydro-5,8-methanoisoquinolin-4-yl}(1,1-dioxidothiomorpholin-4-yl)methanone, (1,1-dioxidothiomorpholin-4-yl)(1-{[3-(trifluoromethoxy)phenyl]amino}-5,6,7,8-tetrahydro-5,8-methanoisoquinolin-4-yl)methanone, (1,1-dioxidothiomorpholin-4-yl)(1-{[4-fluoro-3-(trifluoromethyl)phenyl]amino}-5,6,7,8-tetrahydro-5,8-methanoisoquinolin-4-yl)methanone, {1-[(3-chlorophenyl)amino]-5,6,7,8-tetrahydro-5,8-methanoisoquinolin-4-yl}(1,1-dioxidothiomorpholin-4-yl)methanone, {1-[(3,4-difluorophenyl)amino]-5,6,7,8-tetrahydro-5,8-ethanoisoquinolin-4-yl}(1,1-dioxidothiomorpholin-4-yl)methanone, (1,1-dioxidothiomorpholin-4-yl){4-[(2-fluoro-3-methylphenyl)amino]-5,6,7,8-tetrahydro-5,8-ethanoisoquinolin-1-yl}methanone, (1,1-dioxidothiomorpholin-4-yl){4-[(2-fluoro-5-methylphenyl)amino]-5,6,7,8-tetrahydro-5,8-ethanoisoquinolin-1-yl}methanone, {4-[(3-chloro-4-methylphenyl)amino]-5,6,7,8-tetrahydro-5,8-ethanoisoquinolin-1-yl}(1,1-dioxidothiomorpholin-4-yl)methanone, {1-[(3-chloro-5-fluorophenyl)amino]-5,6,7,8-tetrahydro-5,8-ethanoisoquinolin-4-yl}(1,1-dioxidothiomorpholin-4-yl)methanone, and a salt of these.

The compound of Formula (I) has tautomers or geometric isomers depending on the type of substituents. In the present specification, the compound of the Formula (I) is described in only one form of an isomer in some cases. However, the present invention includes other isomers, separated isomers, or a mixture of these.

In addition, the compound of Formula (I) may have asymmetric carbon atoms or axis chirality in some cases, and there may be optical isomers based on this case. The present invention also includes separated optical isomers of the compound of Formula (I) or a mixture of these.

Moreover, the present invention includes pharmaceutically acceptable prodrugs of the compound represented by Formula (I). The pharmaceutically acceptable prodrugs refer to compounds having a group that can be converted into an amino group, a hydroxyl group, a carboxyl group, or the like by solvolysis or under physiological conditions. Examples of groups that form the prodrugs include the groups disclosed in Prog. Med., 5, 2157-2161 (1985) or in "Pharmaceutical Research and Development", (Hirokawa Publishing Company, 1990), Vol. 7, Drug Design 163-198.

The salt of the compound of Formula (I) refers to a pharmaceutically acceptable salt of the compound of Formula (I), and the salt forms an acid addition salt or a salt with a base in some cases depending on the type of substituents. Specific examples of the salt include acid addition salts with an inorganic acid such as hydrochloric acid, hydrobromic acid, hydriodic acid, sulfuric acid, nitric acid, or phosphoric acid or with an organic acid such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, or glutamic acid, salts with an inorganic base such as sodium, potassium, magnesium, calcium, or aluminum, or with an organic base such as methylamine, ethylamine, ethanolamine, lysine, or ornithine, salts with various amino acids and amino acid derivatives such as acetylleucine, ammonium salts, and the like.

The present invention also includes various hydrates or solvates and polymorphic substances of the compound of Formula (I) and a salt thereof. In addition, the present invention includes compounds labeled with various radioisotopes or non-radioactive isotopes.

(Preparation Process)

The compound of Formula (I) or a salt thereof can be prepared by applying various known synthesis processes, by using characteristics based on the basic structure thereof or the type of substituents. In this regard, depending on the type of functional groups, it is in some cases effective to substitute the functional group in advance with an appropriate protective group (group that can be easily converted into the functional group) during the period from the stage of a starting material to the stage of an intermediate, in terms of the technique of preparation. Examples of the protective group include the protective groups disclosed in Wuts (P. G. M. Wuts) and Greene (T. W. Greene), "Greene's Protective Groups in Organic Synthesis (4th edition, 2006)", and the like. The protective group may be used by being appropriately selected according to the reaction conditions thereof. In this method, the protective group is introduced to cause a reaction, and then the protective group is optionally removed, whereby a desired compound can be obtained.

In addition, a prodrug of the compound of Formula (I) can be prepared by introducing a specific group during the period from the stage of a starting material to the stage of an intermediate just like the above protective group, or by further causing a reaction by using the obtained compound of Formula (I). The reaction can be performed by applying methods known to a person skilled in the art, such as esterification, amidation, and dehydration.

Hereinafter, a typical preparation process of the compound of Formula (I) will be described. Each preparation process can be performed with reference to the reference document included in the corresponding description. Moreover, each preparation process of the invention is not limited to the following examples.

(Preparation Process 1)

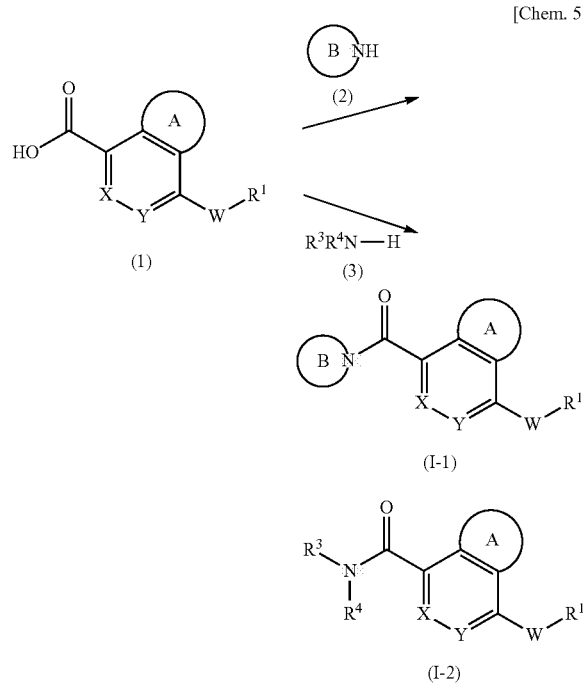

(In the formula, B represents a cyclic amino group which may be substituted, W represents —NH—, —N(lower alkyl)-, —O—, —S—, or —S(O)$_2$—)

The compound of Formula (I-1) or the compound of Formula (I-2) can be obtained by an amidation reaction between a compound (1) and the corresponding cyclic amino compound (2) or chain amino compound (3) which may be substituted.

For example, in this reaction, both the compound (1) and the corresponding cyclic amino compound (2) or chain amino compound (3) which may be substituted are used in an equivalent amount, or one of the compounds is used in an excess amount. A mixture of these compounds is stirred generally for 0.1 hours to 5 days under conditions ranging from cooling to heating, preferably at −20° C. to 100° C., in a solvent inactive to the reaction in the presence of a condensing agent. Though not particularly limited, examples of the solvent used herein include aromatic hydrocarbons such as benzene, toluene, xylene and the like, halogenated hydrocarbons such as dichloromethane, 1,2-dichloroethane, chloroform and the like, ethers such as diethylether, tetrahydrofuran, dioxane, dimethoxyethane and the like, N,N-dimethylformamide, N,N-dimethylimidazolidinone, dimethylsulfoxide, ethyl acetate, acetonitrile, ethanol, water, and a mixture of these. Examples of the condensing agent include, but are not limited to, 1-[bis(dimethylamino)methylene]-1H-1,2,3-triazolo[4,5-b]pyridin-1-ium3-oxide hexafluorophosphate (HATU), 1-(3-dimethylaminopropyl)-3-ethylcarbodiimide (WSC), dicyclohexylcarbodiimide (DCC), 1,1'-carbonyldiimidazole (CDI), diphenyl phosphate azide, and phosphorus oxychloride, and the like. It is preferable to use an additive (for example, 1-hydroxybenzotriazole (HOBt)) in some cases for the reaction. Sometimes, it is advantageous to perform the reaction in the presence of an organic base such as triethylamine, N,N-diisopropylethylamine, N-methylmorpholine or the like, or an inorganic base such as potassium carbonate, sodium carbonate, potassium hydroxide or the like, in terms of causing the reaction to proceed smoothly.

In addition, it is also possible to use a method of converting a carboxyl group moiety of a carboxylic acid derivative (1) into a reactive derivative and then reacting this with the cyclic amino compound (2) or chain amino compound (3) which may be substituted. Examples of the reactive derivative of carboxylic acid include acid halides obtained when the carboxylic acid reacts with a halogenating agent such as phosphorus oxychloride, thionyl chloride or the like, mixed acid anhydrides obtained when the carboxylic acid reacts with isobutyl chloroformate or the like, and active esters obtained when the carboxylic acid is fused with 1-hydroxybenzotriazole or the like. The reaction between these reactive derivatives and the compound (2) or (3) can be performed in a solvent inactive to the reaction, such as halogenated hydrocarbons, aromatic hydrocarbons, or ethers, under conditions ranging from cooling to heating preferably at −20° C. to 60° C.

[Document]

S. R. Sandler and W. Karo, "Organic Functional Group Preparations", 2nd edition, Vol. 1, Academic Press Inc., 1991

The Chemical Society of Japan., "Jikken Kagaku Koza (Courses in Experimental Chemistry) (5th edition)", Vol. 16, (2005) (MARUZEN Co., Ltd.)

(Preparation Process 2)

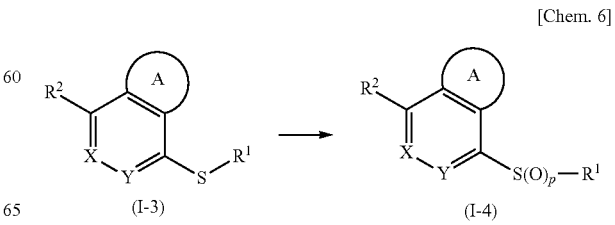

(In the formula, p represents 1 or 2)

The compound of Formula (I-4) can be obtained by an oxidation reaction of the compound of Formula (I-3) in which W represents —S—, among the compounds of Formula (I-1) or the compounds of Formula (I-2) obtained by the Preparation process 1.

For example, the compound (I-3) may be treated with an oxidant which is used in an equivalent amount to the compound or used in an excess amount compared to the compound generally for 0.1 hours to 3 days in a solvent inactive to the reaction, under conditions ranging from cooling to heating preferably at −20° C. to 80° C. Examples of the solvent used herein include, but are not limited to, ethers such as diethylether, tetrahydrofuran, dioxane, dimethoxyethane and the like, halogenated hydrocarbons such as dichloroethane, 1,2-dichloroethane, chloroform and the like, aromatic hydrocarbons such as benzene, toluene, xylene and the like, N,N-dimethylformamide, dimethyl sulfoxide, and ethyl acetate, water, and a mixture of these. As the oxidant, for example, m-chloroperbenzoic acid, sodium periodate, and the like are suitably used.

[Documents]

B. M. Trost, "Comprehensive Organic Synthesis", Vol. 7, 1991

M. Hudlicky, "Oxidation in Organic Chemistry (ACS Monograph: 186)", ACS, 1990

The Chemical Society of Japan., "Jikken Kagaku Koza (Courses in Experimental Chemistry) ($5^{th}$ edition)", Vol. 17, (2005) (MARUZEN Co., Ltd.)

(Preparation Process 3)

[Chem. 7]

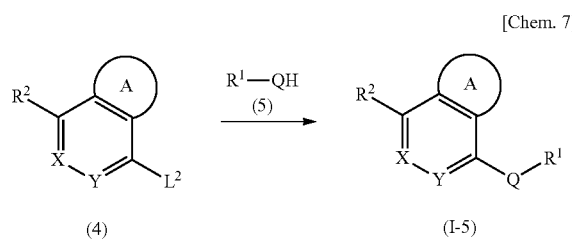

(In the formula, $L^1$ represents an elimination group, and Q represents —NH— or —O—)

The compound of Formula (I-5) can be obtained by a reaction between a compound (4) and a compound (5). Herein, examples of the elimination group include halogen, methanesulfonyloxy, a p-toluenesulfonyloxy group, and the like.

In the reaction, both the compound (4) and compound (5) are used in an equivalent amount, or one of the compounds is used in an excess amount. A mixture of these is stirred generally for 0.1 hours to 5 days in a solvent inactive to the reaction in the presence of a base and a palladium catalyst, under conditions ranging from cooling to heating under reflux preferably at 0° C. to 100° C. Though not particularly limited, examples of the solvent used herein include aromatic hydrocarbons such as benzene, toluene, xylene and the like, ethers such as diethylether, tetrahydrofuran, dioxane, dimethoxyethane and the like, halogenated hydrocarbons such as dichloromethane, 1,2-dichloroethane, chloroform and the like, N,N-dimethylformamide, dimethylsulfoxide, ethyl acetate, acetonitrile, and a mixture of these. Sometimes, it is advantageous to perform the reaction in the presence of an organic base such as triethylamine, N,N-diisopropylethylamine, N-methylmorpholine or the like, or an inorganic base such as potassium carbonate, sodium carbonate, potassium hydroxide, sodium tert-butoxide, potassium tert-butoxide or the like, in terms of causing the reaction to proceed smoothly. Examples of the palladium catalyst include tris(dibenzylideneacetone)dipalladium and the like. In addition, it is advantageous in some cases to perform the reaction in the presence of 2,2'-bis(diphenylphosphino)-1,1'binaphthyl or the like as a separate ligand, in terms of causing the reaction to proceed smoothly.

Moreover, in the present process, when Q represents —O—, both the compound (5) and a base are used in an equivalent amount, or one of them is used in an excess amount. A mixture of these is stirred generally for 0.1 hours to 5 days in a solvent inactive to the reaction under conditions ranging from cooling to heating under reflux, and then the compound (4) is added thereto, followed by stirring with heating under reflux from room temperature, whereby a compound (I-5) can be obtained. Examples of the base used herein include sodium hydride.

It is also possible to employ a method in which both the compound (4) and the compound (5) are used in an equivalent amount, or one of them is used in an excess amount, a mixture of these is heated in a solvent inactive to the reaction to prepare the compound (I-5). In this case, it is advantageous in some cases to perform the reaction under acidic conditions, for example, in the presence of a 4 M hydrogen chloride/dioxane solution, in terms of causing the reaction to proceed smoothly.

(Preparation Process 4)

[Chem. 8]

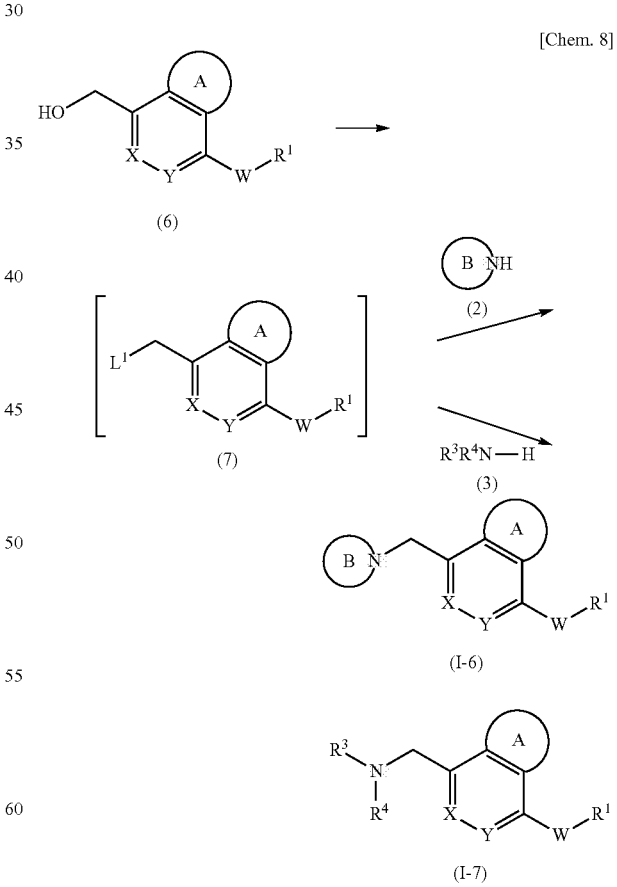

The compound of Formula (I-6) or (I-7) can be obtained by converting a hydroxyl group of a compound (6) into an elimination group and then reacting the elimination group with the corresponding cyclic amino compound (2) or chain amino compound (3) which may be substituted.

The reaction can be performed by converting a hydroxyl group of the compound (6) into, for example, halogen such as chloro, bromo, iodo or the like, or a sulfonyloxy such as methanesulfonyloxy, ethanesulfonyloxy, benzenesulfonyloxy, 4-methylbenzenesulfonyloxy, trifluoromethanesulfonyloxy or the like, or trifluoromethoxy group and stirring the resultant generally for 0.1 hours to 5 days in the presence of an appropriate base, in a solvent inactive to the reaction or without using a solvent, under conditions ranging from cooling to heating preferably at room temperature or under heating. Thereafter, both the compound (7) of which a hydroxyl group has been converted into an elimination group and the cyclic amino compound (2) or chain amino compound (3) which may be substituted are used in an equivalent amount, or one of the compounds is used in an excess amount, and the compounds are stirred generally for 0.1 hours to 5 days in the presence of a base, in a solvent inactive to the reaction under conditions ranging from cooling to heating under reflux. Though not particularly limited, examples of the solvent used herein include aromatic hydrocarbons such as benzene, toluene, xylene and the like, ethers such as diethylether, tetrahydrofuran, dioxane, dimethoxyethane and the like, halogenated hydrocarbons such as dichloromethane, 1,2-dichloroethane, chloroform and the like, N,N-dimethylformamide, dimethylsulfoxide, ethyl acetate, acetonitrile, and a mixture of these. Examples of the base include organic bases such as triethylamine, diisopropylethylamine, 1,8-diazabicyclo[5.4.0]-7-undecene, n-butyllithium and the like, and inorganic bases such as sodium carbonate, potassium carbonate, sodium hydride, potassium tert-butoxide and the like. Sometimes, it is advantageous to perform the reaction in the presence of a phase-transfer catalyst such as tetra-n-butylammonium chloride.

[Document]

S. R. Sandler and W. Karo, "Organic Functional Group Preparations", 2$^{nd}$ edition, Vol. 1, Academic Press Inc., 1991

The Chemical Society of Japan., "Jikken Kagaku Koza (Courses in Experimental Chemistry) (5$^{th}$ edition)", Vol. 14, (2005) (MARUZEN Co., Ltd.)

(Starting Material Synthesis 1)

[Chem. 9]

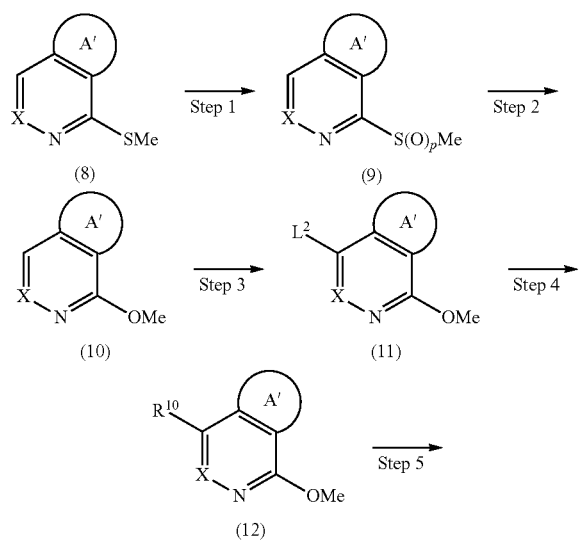

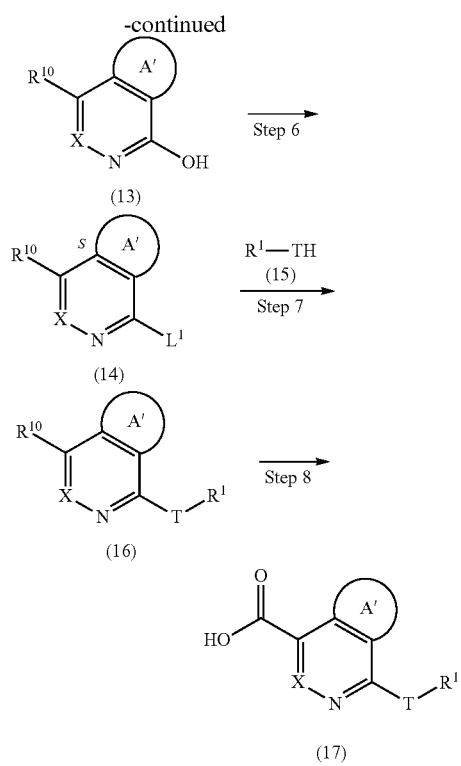

(In the formula, the A' portion represents Formula (II) or (III), T represents NH, —O—, or —S—, $L^2$ represents halogen, and $R^{10}$ represents cyano or —C(O)O-lower alkyl)

This preparation process is a method of preparing a compound (17) in which A portion is represented by Formula (II) or (III), among the compounds (1) as a starting compound of the Preparation process 1.

(Step 1)

This step is a step of obtaining a compound (9) by oxidizing the compound (8) that is prepared by the method described in Tetrahedron, 1992, 48(36), 7663-7678, or by a method based on the above method.

This reaction can be performed by the same method as in Preparation process 2.

(Step 2)

This step is a step of obtaining a compound (10) by introducing a methoxy group into the compound (9).

In this reaction, a base is added to a mixture of the compound (9) and methanol, and the resultant is stirred generally for 0.1 hours to 3 days under conditions ranging from cooling to heating. Examples of the base used herein include sodium methoxide.

(Step 3)

This step is a step of obtaining a compound (11) by halogenating the compound (10).

In this reaction, both the compound (10) and a halogenating agent are used in an equivalent amount, or one of them is used in an excess amount. The compound and the agent are stirred generally for 0.1 hours to 5 days in a solvent inactive to the reaction under conditions ranging from cooling to heating under reflux, whereby the reaction can be performed. Though not particularly limited, examples of the solvent used herein include halogenated hydrocarbons such as dichloromethane, 1,2-dichloroethane, chloroform and the like. In addition, as the halogenating agent, N-bromosuccinimide, N-chlorosuccinimide, and the like can be used.

(Step 4)

This step is a step of obtaining a compound (12) by cyanidation or esterification of the compound (11).

In this reaction, both the compound (11) and a predetermined cyano compound are used in an equivalent amount, or one of the compounds is used in an excess amount. A mixture of these is stirred generally for 0.1 hours to 5 days in a solvent inactive to the reaction, in the presence of a palladium catalyst under heating under reflux from room temperature, whereby the reaction can be performed. Though not particularly limited, examples of the solvent used herein include aromatic hydrocarbons such as benzene, toluene, xylene and the like, ethers such as diethylether, tetrahydrofuran, dioxane, dimethoxyethane and the like, halogenated hydrocarbons such as dichloromethane, 1,2-dichloroethane, chloroform and the like, N,N-dimethylformamide, dimethylsulfoxide, N-methylpyrrolidone, and a mixture of these. Examples of the cyano compound include zinc cyanide, sodium cyanide, potassium cyanide, and the like. Examples of the palladium catalyst include tris(dibenzylideneacetone)dipalladium and the like. Also, it is advantageous in some cases to perform the reaction in the presence of 1,1-bis(diphenylphosphino)ferrocene as an additional ligand, in terms of causing the reaction to proceed smoothly. Moreover, sometimes, it is advantageous to perform the reaction in the presence of metal powder, for example, zinc powder, in terms of causing the reaction to proceed smoothly.

In addition, instead of cyanidation, carbon monoxide may be inserted into the compound (11), and the compound subsequently reacted with alcohol in the reaction system, whereby the compound (12) as an ester derivative can be prepared.

In this reaction both the compound (11) and carbon monoxide are used in an equivalent amount, or one of them is used in an excess amount. The compound and the carbon monoxide are stirred generally for 0.1 hours to 5 days in the presence of a palladium catalyst and a base, in the following solvent under conditions ranging from cooling to heating under reflux, whereby the reaction can be performed. Though not particularly limited, examples of the solvent used herein include N,N-dimethylformamide and the like, alcohols such as methanol ethanol and the like, and a mixture of these. Moreover, as the palladium catalyst, for example, palladium acetate is used. In addition, as the base, triethylamine is used for example. Moreover, it is advantageous in some cases to perform the reaction in the presence of a ligand, for example, diphenylphosphinoferrocene, in terms of causing the reaction to proceed smoothly.

(Step 5)

This step is a step of obtaining a compound (13) by demethylation of the compound (12).

In this reaction, both the compound (12) and, for example, trimethylsilyl chloride are used in an equivalent amount, or one of them is used in an excess amount. A mixture of these is stirred generally for 0.1 hours to 5 days in a solvent inactive to the reaction under heating under reflux from room temperature, whereby the reaction can be performed. Though not particularly limited, examples of the solvent used herein include acetonitrile and the like. In addition, it is in some cases advantageous to perform the reaction in the presence of potassium iodide, sodium iodide or the like, in terms of causing the reaction to proceed smoothly.

Moreover, instead of trimethylsilyl chloride, concentrated hydrochloric acid or the like can be used. In this case, as a solvent, for example, dioxane, water, and a mixture of these can be used.

(Step 6)

This step is a step of obtaining a compound (14) by converting a hydroxyl group of the compound (13) into a predetermined elimination group.

In this reaction, a hydroxyl group of the compound (13) is stirred generally for 0.1 hours to 5 days in the presence of a halogenating agent or the like and an appropriate base, in a solvent inactive to the reaction or without using a solvent, under conditions ranging from cooling to heating, preferably under heating from room temperature, whereby a hydroxyl group of the compound can be converted into halogen such as chloro, bromo, iodo or the like, or a sulfonyloxy group such as methanesulfonyloxy, ethanesulfonyloxy, benzenesulfonyloxy, 4-methylbenzenesulfonyloxy, or trifluoromethanesulfonyloxy or the like, or trifluoromethoxy group.

(Step 7)

This step is a step of obtaining a compound (16) by a reaction between the compound (14) and the compound (15).

This reaction can be performed by the method described in Preparation process 3.

In addition, when T represents —S—, both the compound (14) and $R^1$—SH— are used in an equivalent amount, or one of them is used in an excess amount. A mixture of these is stirred generally for 0.1 hours to 5 days in a solvent inactive to the reaction, in the presence of a palladium catalyst under heating under reflux from room temperature, whereby the reaction is performed. Though not particularly limited, examples of the solvent used herein include dioxane and the like. As the palladium catalyst, for example, palladium acetate is suitably used. Moreover, it is in some cases advantageous to perform the reaction in the presence of a ligand, for example, bis[2-(diphenylphosphino)phenyl]ether, in terms of causing the reaction to proceed smoothly.

(Step 8)

This step is a step of obtaining a compound (17) by causing hydrolysis of the compound (16).

In this reaction, when $R^{10}$ in the compound represents cyano, the compound is stirred generally for 0.1 hours to 5 days in the following solvent under heating under reflux from room temperature, preferably under heating under reflux, under acidic or basic conditions. Examples of the solvent used herein include ethers such as diethylether, tetrahydrofuran, dioxane, dimethoxyethane and the like, alcohols such as methanol ethanol and the like, water, and a mixture of these. Examples of an acid used when the reaction is performed under acidic conditions include hydrochloric acid, sulfuric acid, and the like. Examples of a base used when the reaction is performed under basic conditions include an aqueous sodium hydroxide solution, an aqueous potassium hydroxide solution, and the like.

In a case of a compound in which $R^{10}$ represents $CO_2R^{11}$, the reaction can be performed with reference to Greene and Wuts, "Protective Groups in Organic Synthesis", $3^{rd}$ edition, John Wiley & Sons Inc, 1999.

(Starting Material Synthesis 2)

[Chem. 10]

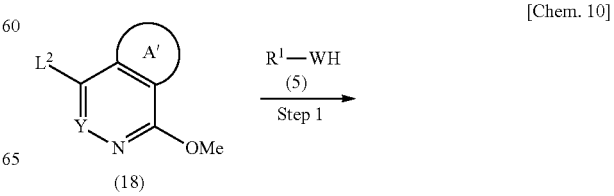

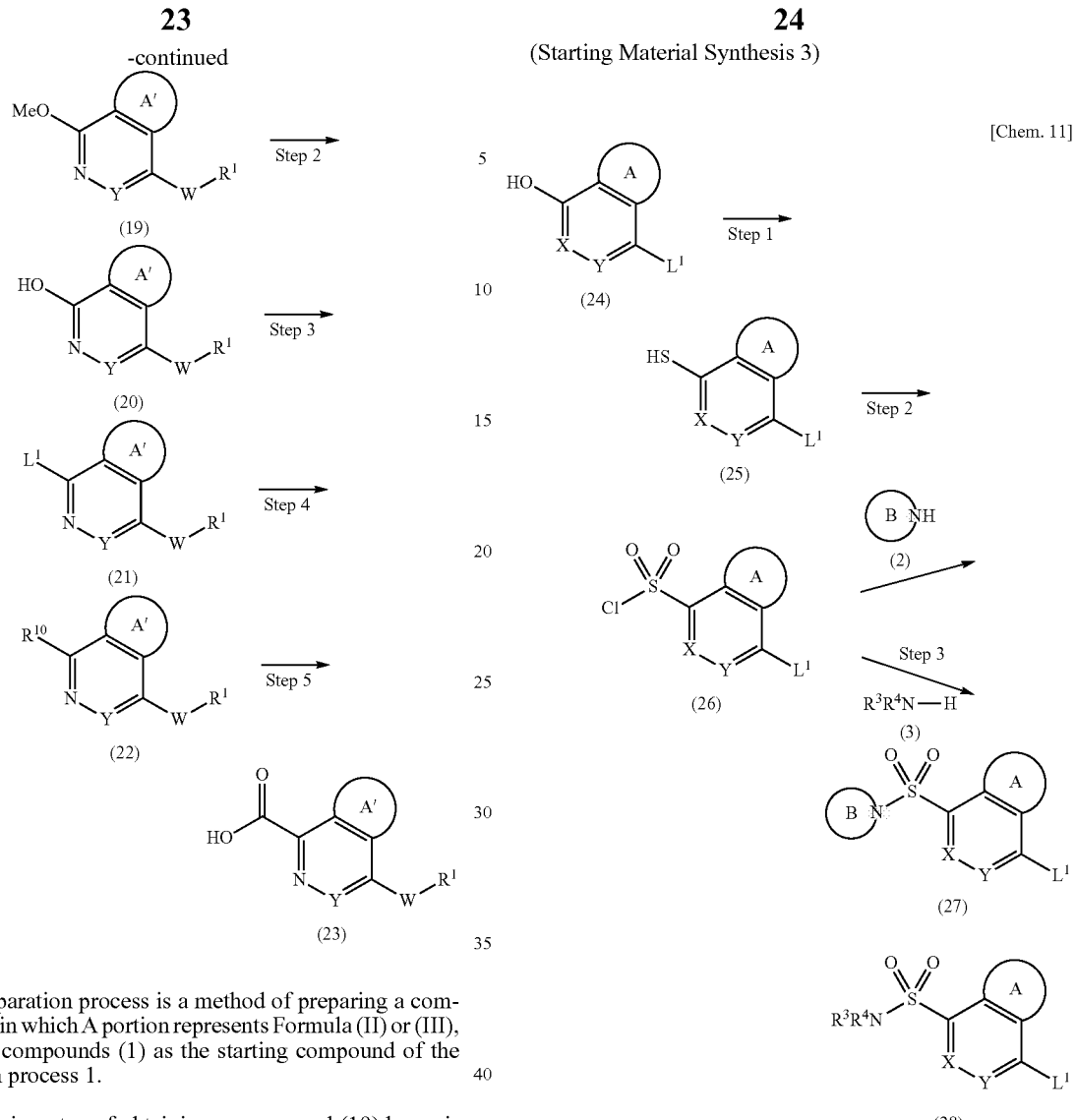

(Starting Material Synthesis 3)

[Chem. 11]

This preparation process is a method of preparing a compound (23) in which A portion represents Formula (II) or (III), among the compounds (1) as the starting compound of the Preparation process 1.

(Step 1)

This step is a step of obtaining a compound (19) by amination of the compound (18).

The reaction conditions are the same as in Preparation process 3.

(Step 2)

This step is a step of obtaining a compound (20) by demethylation of the compound (19).

The reaction conditions are the same as in Step 5 of Starting material synthesis 1.

(Step 3)

This step is a step of obtaining a compound (21) by converting a hydroxyl group of the compound (20) into a predetermined elimination group.

The reaction conditions are the same as in Step 6 of Starting material synthesis 1.

(Step 4)

This step is a step of obtaining a compound (22) by cyanidation or esterification of an elimination group $L^1$ of the compound (21).

The reaction conditions are the same as in Step 4 of Starting material synthesis 1.

(Step 5)

This step is a step of obtaining a compound (23) by hydrolysis of the compound (22).

The reaction conditions are the same as in Step 8 of Starting material synthesis 1.

This preparation process is a method of preparing a compound (27) and a compound (28) in which —Z— represented by $R^2$ represents —S(O)$_2$—, among the compounds (4) as a starting compound of Preparation process 3.

(Step 1)

This step is a step of obtaining a compound (25) by converting a hydroxyl group of the compound (24) into a thiol group.

In this reaction, the compound (24) is treated with Lawesson's reagent which is used in an equivalent amount to the compound or used in an excess amount compared to the compound, generally for 0.1 hours to 3 days in a solvent inactive to the reaction under conditions ranging from cooling to heating. Though not particularly limited, examples of the solvent used herein include aromatic hydrocarbons such as benzene, toluene, xylene and the like.

(Step 2)

This step is a step of obtaining a compound (26) by converting a thiol group of the compound (25) into sulfonyl chloride.

In this reaction, the compound (25) is treated with an oxidant which is used in an equivalent amount to the compound or used in an excess amount compared to the compound, generally for 0.1 hours to 3 days in a solvent inactive to the reaction under conditions ranging from cooling to heating, under acidic conditions. Though not particularly limited, examples of the solvent used herein include halogenated hydrocarbons such as dichloromethane, 1,2-dichloroethane, chloroform and the like, water, and a mixture of these. As the oxidant, for example, sodium hypochlorite is used. To create acidic conditions, for example, concentrated hydrochloric acid is used.

(Step 3)

This step is a step of obtaining a compound (27) or a compound (28) by amidation of the compound (26).

This reaction can be performed by the same method as in Preparation process 1.

(Starting Material Synthesis 4)

[Chem. 12]

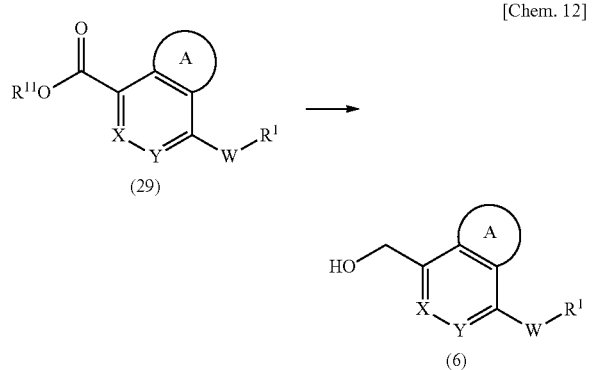

(In the formula, $R^{11}$ represents lower alkyl)

This preparation process is a method of preparing the compound (6) as a starting compound of Preparation process 4.

The compound (6) can be prepared by reducing an ester group of a compound (29).

In this reaction, the compound (29) is treated with a reductant which is used in an equivalent amount to the compound or used in an excess amount compared to the compound, generally for 0.1 hours to 3 days in a solvent inactive to the reaction, under conditions ranging from cooling to heating, preferably at −20° C. to 80° C. Though not particularly limited, examples of the solvent used herein include ethers such as diethylether, tetrahydrofuran, dioxane, dimethoxyethane and the like, alcohols such as methanol, ethanol, 2-propanol and the like, aromatic hydrocarbons such as benzene, toluene, xylene and the like, N,N-dimethylformamide, dimethylsulfoxide, ethyl acetate, and a mixture of these. As the reductant, a hydride reductant such as sodium borohydride, diisobutyl aluminum hydride, or the like, metal reductants such as sodium, zinc, iron or the like, and other reductants disclosed in the following documents are suitably used. In addition, it is advantageous in some cases to perform the reaction in the presence of an additive, for example, calcium chloride, in terms of causing the reaction to proceed smoothly.

[Documents]

M. Hudlicky, "Reductions in Organic Chemistry, $2^{nd}$ ed (ACS Monograph: 188), ACS, 1996

R. C. Larock, "Comprehensive Organic Transformations", $2^{nd}$ edition, VCH Publishers, Inc. 1999

T. J. Donohoe, "Oxidation and Reduction in Organic Synthesis (Oxford Chemistry Primers 6), Oxford Science Publications, 2000

The Chemical Society of Japan., "Jikken Kagaku Koza (Courses in Experimental Chemistry) ($5^{th}$ edition)", Vol. 14, (2005) (MARUZEN Co., Ltd.)

The pharmacological activity of the compound of Formula (I) was confirmed by the following tests.

Test Example 1

Test on Inhibition of Human CB2-Mediated Cyclic AMP (cAMP) Production

This test was performed using CHO cells caused to express human CB2 ("Molecular Pharmacology", 1995, Vol. 48, pp 443-450).

A human CB2-expressing CHO cell ($2.5 \times 10^3$/mL) suspension and an assay medium supplemented with a test substance and forskolin (final concentration of 0.5 μM) were mixed together in equal amounts, followed by incubation for 30 minutes at room temperature, and then a 0.6% Triton X-100 solution was added thereto, thereby obtaining a cell lysate. A cAMP concentration in the cell lysate was measured using a cAMP kit (manufactured by Cisbio International). The assay medium was obtained by supplementing α-MEM manufactured by Invitrogen with 0.02% CHAPS, 1 mM isobutylmethylxanthine, and 0.5 mg/mL bovine serum albumin. The cAMP concentration in a forskolin-free cell suspension was regarded as 0% of increase in cAMP, and the cAMP concentration in a forskolin-added cell suspension was regarded as a 100% increase in cAMP, thereby allowing calculation of the inhibition rate of intracellular cAMP increase in 30 nM test substance.

Results obtained from several typical compounds are shown in Table 1. In the table, Ex represents the example number of a test compound described later, and Inh represents inhibition rate of cAMP increase.

TABLE 1

| Ex | Inh(%) |
| --- | --- |
| 10 | 73 |
| 11 | 77 |
| 16 | 87 |
| 30 | 82 |
| 33 | 81 |
| 36 | 82 |
| 38 | 77 |
| 52 | 96 |
| 59 | 93 |
| 94-1 | 97 |
| 98 | 96 |
| 101 | 99 |
| 112 | 103 |
| 117-2 | 100 |
| 119-2 | 91 |
| 120-2 | 105 |
| 125 | 100 |
| 129 | 95 |
| 133-2 | 90 |
| 138 | 97 |
| 164 | 119 |
| 165 | 111 |
| 167 | 115 |
| 179 | 100 |

Test Example 2

Effect of Inhibition of Hind Paw Weight Distribution in Adjuvant-Induced Arthritis Rat For this test, female Lewis rats (7- to 8-weeks-old) were used. 50 μL of killed *Mycobacterium tuberculosis* H37 Ra (manufactured by DIFCO MICROBIOLOGY) suspended in liquid paraffin at a concentration of 10 mg/mL was subcutaneously administered to the right hind footpad. On the next day, the test substance was administered orally, and after some time, the load on the left and right hind paws was measured using an Incapacitance Tester (manufactured by Linton Instruments), thereby calculating a difference in the load between left and right. The load difference of a Vehicle-administered group was regarded as an inhibition rate of 0%, and the load difference of a Normal group was regarded as an inhibition rate of 100%, thereby allowing calculation of the inhibition rate of the test substance.

Results obtained from several typical compounds are shown in Table 2. In the table, Ex represents an example number of a test compound described later, and values in the parenthesis indicates a dose.

TABLE 2

| Ex | Inhibition rate (%) |
| --- | --- |
| 10 | 30 (0.1 mg/kg) |
| 16 | 29 (0.1 mg/kg) |
| 30 | 17 (0.1 mg/kg) |
| 36 | 49 (0.1 mg/kg) |
| 119-2 | 49 (0.3 mg/kg) |
| 120-2 | 34 (0.3 mg/kg) |
| 133-2 | 39 (0.3 mg/kg) |
| 138 | 54 (0.3 mg/kg) |

As shown in the above test, several typical compounds have excellent CB2 agonist action, and this shows that the compounds can be used for preventing and/or treating the following CB2-related diseases.

Inflammatory diseases, for example, diseases such as dermatitis, contact dermatitis, allergic dermatitis, atopic dermatitis, dermatitis such as lacquer poisoning and cosmetics rash, allergic rhinitis, seasonal allergic rhinitis, chronic bronchitis, bronchitis, pneumonia, sudden interstitial pneumonia, reflux esophagitis, gastritis, atopic gastritis, pancreatitis, myocarditis, pericarditis, endocarditis, hepatitis, inflammatory bowel diseases, colitis, intractable bowel diseases, ulcerative colitis, inflammatory enteritis, localized ileitis, nephritis, glomerulonephritis, nephritic syndrome, angiitis, allergic granulomatous angiitis, ulcerative angiitis, vasculitis, rheumatoid spondylitis, arthritis, osteoarthritis, psoriatic arthritis, gouty arthritis, juvenile arthritis, reactive arthritis, undifferentiated spondylarthritis, retinitis, uveitis, chorioditis of the uveal tract, conjunctivitis, allergic conjunctivitis, keratoconjunctivitis, infective conjunctivitis, periarteritis nodosa, thyroiditis, polymyositis, ulitis, pyrexia, tendinitis, bursitis, cystitis, ankylosing spondylitis, encephalitis, meningitis, malignant meningitis, bacterial encephalomeningitis, cytomegalovirus meningitis, neuritis, sunburn, burns, rheumatic fever, vulvar vestibulitis, stomatitis, acute vaginitis, balanitis, balanoposthitis, chronic inflammation of the mucous membrane, dermatomyositis, Hashimoto's thyroiditis, and chronic inflammatory diseases (pain accompanied by rheumatoid arthritis, arthrosis deformans, rheumatoid spondylitis, gouty arthritis, juvenile arthritis, and multiple sclerosis).

Pain, for example, rheumatoid arthritis pain, arthrosis deformans pain, chronic pain, inflammatory chronic pain, acute pain, acute peripheral pain, lower back pain, chronic lower back pain, back pain, headache, migraine, toothache, inflammatory pain, nociceptive pain, neurogenic pain, neuropathic pain, myalgia, fibromyalgia, visceralgia, pelvic pain, neuralgia, sciatic neuralgia, postherpetic neuralgia, diabetic pain, HIV-related pain, cancer pain, central trigeminal neuralgia, neurogenic lower back pain, fibromuscular and skeletal pain, psychogenic pain, dysmenorrhea, paralgesia, hyperpathia, hypalgia, toothache, neck pain, pain accompanied by virus infection, pain accompanied by influenza virus infection, functional abdominal pain (non-ulcerative gastrointestinal disturbance, non-cardiac pain, irritable bowel syndrome, and the like), pain accompanied by myocardial ischemia, pain resulting from trauma and toxin, allodynia, and stroke-induced pain, and diseases such as sprain and muscle strain.

Cancer and tumors, for example, diseases such as cancer in the immune system, lung cancer, colorectal cancer, malignant brain tumor, skin cancer, uterine cancer, breast cancer, prostate cancer, leukemia, benign cutaneous neoplasm, cancerous tumor, papilloma, small cell lung cancer, glioblastoma, medulloepithelioma, medulloblastoma, neuroblastoma, embryonal tumor, astrocytoma, astroblastoma, ependymoma, oligodendroglioma, plexus tumor, neuroepithelioma, epiphyseal tumor, ependymoblastoma, neuroectodermal tumor, sarcomatosis, malignant melanoma, schwannoma, lymphoma, neuroglioma, thyroidal epithelioma, neuroblastoma, cutaneous T-cell lymphoma, neuroglioma, tumors, pineal tumor, and malignant myeloma.

Respiratory diseases, for example, diseases such as respiratory distress syndrome, acute respiratory distress syndrome, pulmonary tuberculosis, coughing diseases, bronchial asthma, cough resulting from enhanced hypersensitivity of the respiratory tract (bronchitis, upper respiratory infection, asthma, obstructive pulmonary disease, and the like), cold syndrome, antitussive effect, hypersensitivity of the respiratory tract, tuberculosis lesion, asthma (inflammatory cellular infiltration in the respiratory tract, enhanced hypersensitivity of the respiratory tract, bronchoconstriction, mucus hypersecretion, and the like), chronic obstructive pulmonary disease, emphysema, pulmonary fibrosis, idiopathic pulmonary fibrosis, cough, reversible respiratory tract obstruction, adult respiratory disease syndrome, pigeon fancier's disease, farmer's lung, bronchopulmonary dysplasia, respiratory tract disorder, and pneumatosis.

Liver diseases, for example, diseases such as hepatic fibrosis, hepatic infarction, and chronic hepatic cirrhosis.

Brain diseases, for example, diseases such as brain injury, cerebral infraction, stroke, an agent for treating brain tumors, cerebral ischemia, acute cerebral ischemia, and cerebrovascular ischemia.

Eye diseases, for example, diseases such as ocular hypertension, cataracts, glaucoma, retinal detachment, retinosis, retinal diseases, eyeball disorder, and keratohelcosis.

Skin diseases, for example, diseases such as pruritus, pachyderma, senile xeroderma, and scleroderma.

Circulatory diseases, for example, diseases such as angina pectoris, unstable angina, myocardial infarction, heart failure, multiple sclerosis, arteriosclerosis, atherosclerosis, arrhythmia, hypertension syndrome, ischemic heart disease, cardiac crisis, cardiac ischemia, cardioplegia, peripheral vasodilation, hypertension, hypotension, restenosis after coronary stenting, thrombosis, vascular diseases, and symptoms of cardiovascular diseases accompanied by vascular remodeling.

Allergic diseases, for example, diseases such as anaphylaxis, allergy of the digestive tract, allergic gastrointestinal diseases, allergic asthma, atopic asthma, allergic bronchopulmonary aspergillosis, pollen allergy, and drug allergies.

Digestive diseases, for example, diseases such as constipation, diarrhea, secretory diarrhea, vomiting (cancer chemotherapy-induced vomiting), nausea, particularly, nausea accompanied by chemotherapy, nausea accompanied by AIDS wasting syndrome, gastroesophageal reflux disease, peptic ulcer, irritable bowel syndrome, functional gastrointestinal disturbance, inflammatory intestinal disease, and ulcerative colitis.

Urogenital diseases, for example, diseases such as difficult menstruation.

Immunological diseases, for example, diseases such as immunological incompetence, immunoregulation, autoimmune diseases, T-cell lymphoma, psoriasis, psoriasis vulgaris, rheumatoid arthritis, osteoporosis, sepsis, septic shock, systemic lupus erythematosus, autoimmune hemolytic anemia, and AIDS.

Complication accompanied by transplantation, for examples, diseases such as rejection after organ transplantation and graft-versus-host disease.

Neurogenic diseases, for examples, diseases such as neurodegenerative diseases, depression, manic depression, nausea, vertigo, phantom limb, nerve disorder, peripheral nerve disorder, nerve injury, traumatic neurosis, dementia, senile dementia, dementia, senile dementia, Alzheimer's disease, psychosis, schizophrenia, Pick's disease, Huntington's chorea, chorea, Parkinson's disease, Creutzfeldt-Jakob disease, motor nerve diseases, dementia resulting from multiple cerebral infarction, anoxia, avitaminosis, memory disorder accompanied by aging, schizophrenic disorder, depression, anxiety, panic disorder, agoraphobia, social phobia, obsessive-compulsive disorder, post traumatic stress disorder, memory disorder, amnesia, appestat, lack of appetite, anorexia, bulimia nervosa, functional disorder, circadian dysrhythmia, sleep disturbance, dyssomnia, insomnia, hypersomnia, sleep apnea, drug dependence, heartburn, dysphagia, pelvic hypersensitivity, neurodegeneration (accompanied by stroke, cardiac arrest, traumatic brain disorder, and myelopathy), dyskinesia, convulsions, muscle cramp, tremor, paresthesia, and hyperesthesia.

Other diseases such as Guillain-Barre syndrome, Paget's disease, chronic infirmity, aversion, myasthenia gravis, diabetes, type I diabetes mellitus, ischemic condition, spontaneous pneumothorax, neurodegenerative syndrome, hives, Sjogren's syndrome, spinal cord injury, traumatic cartilage injury, epilepsy, transient cerebral ischemic attack, opportunistic infections (HIV and the like), lichen planus, pemphigus, bullous epidermolysis, hypertrophic scar, keloids, arthrosis, cardiac ischemia disorder, infarction, serum sickness, renal ischemia, aphthous ulcer, Crohn's disease, celiac disease, aplastic anemia, Hodgkin's disease, nephrotic syndrome, endotoxic shock, hypotensive shock, for fertility reduction, Tourette syndrome, for memory inhibition, eczema, sarcoidosis, adult respiratory distress syndrome, coronary artery disease, melanoma, Graves' disease, Goodpasture syndrome, amylosis, diseases affecting the plasma cell line, delayed or immediate hypersensitivity, parasitic, viral, or bacterial infection, spinal injury, dizziness, obesity, connective tissue diseases, diseases affecting the lymphatic hematopoietic system, amyotrophic lateral sclerosis, complicated muscle cramp, complicated cachexia syndrome, and bacterial meningism.

The pharmaceutical composition containing one or two or more kinds of the compound of Formula (I) or a salt thereof as an active ingredient can be prepared using excipients generally used in the related art, that is, using excipients or carriers for medications, by methods generally used.

The composition can be administered in any forms such as oral administration by using a tablet, a pill, a capsule, granules, powder, or liquid, and parenteral administration by using a preparation for injection such as intra-articular injection, intravenous injection, and intramuscular injection, a suppository, eye drops, an eye ointment, a transdermal liquid, an ointment, a transdermal patch, a transmucosal liquid, a transmucosal patch, or an inhalation.

As a solid composition for oral administration, a tablet, powder, granules, and the like are used. In such a solid composition, one or two or more kinds of active ingredients are mixed with at least one kind of inactive excipient. The composition may contain inactive additives, for example, a lubricant, a disintegrating agent, a stabilizer, and a dissolution adjuvant according to common methods. The tablet or pill may optionally be coated with sugar or with film of a gastric or enteric material.

A liquid composition for oral administration includes a pharmaceutically acceptable opalizer, solution, suspension, syrup, elixir, or the like, and contains a generally used inactive diluent, for example, purified water or ethanol. The liquid composition may contain an auxiliary agent such as a solubilizer, a moisturizer, or a suspension, a sweetener, a flavor, an aromatic, and a preservative, in addition to the inactive diluent.

The injection preparation for parenteral administration contains a sterile aqueous or non-aqueous solvent, a suspension, or an opalizer. Examples of the aqueous solvent include distilled water for injection and physiological saline. Examples of the non-aqueous solvent include alcohols such as ethanol. These compositions may further contain a tonicity agent, a preservative, a moisturizer, an emulsifier, a dispersant, a stabilizer, or a solubilizer. These are sterilized by, for example, filtering in which they are filtered through a bacteria retentive filter, by being mixed with a germicide, or by irradiation. Moreover, these can be used by being prepared as a sterile solid composition and dissolved or suspended in sterile water or a sterile vehicle for injection before use.

Examples of agents for external use include an ointment, a plaster, a cream, a jelly, a cataplasm, a spray, a lotion, eye drops, an eye ointment, and the like. The agent for external use contains generally used substrates of ointments and lotions, an aqueous or non-aqueous liquid formulation, a suspension, an emulsion, and the like.

Transmucosal agents such as an inhalation and a transnasal agent are used in the form of a liquid or a semisolid, and can be prepared according to methods known in the related art. For example, a known excipient, a pH adjustor, a preservative, a surfactant, a lubricant, a stabilizer, a thickener or the like may be appropriately added thereto. For administration, appropriate devices for inhalation or insufflation can be used. For example, by using a known device such as a metered dose inhaler or an atomizer, the compound can be administered alone or administered as powder of a formulated mixture or as a solution or suspension which is a combination of the compound with a pharmaceutically acceptable carrier. A dry powder inhaler and the like may be for single administration or multiple administration, and dry powder or powder-containing capsules can be used. Alternatively, the compound may be administered in the form of a pressurized aerosol spray using an appropriate ejection agent, for example, a suitable gas such as a chlorofluoroalkane, hydrofluoroalkane, or carbon dioxide.

Generally, in the case of oral administration, an appropriate daily dose is about 0.001 mg/kg to 100 mg/kg in terms of body weight, preferably 0.1 mg/kg to 30 mg/kg, and more preferably 0.1 mg/kg to 10 mg/kg, which is administered once or two to four times in separate doses. In the case of intravenous administration, an appropriate daily dose is about 0.0001 mg/kg to 10 mg/kg in terms of body weight, which is administered once or plural times a day in separate doses. In addition, the transmucosal agent is administered once a day or plural times a day in separate doses, in a dose of about 0.001 mg/kg to 100 mg/kg in terms of body weight. The dose is appropriately determined case by case in consideration of the symptoms, age, gender, and the like.

The pharmaceutical composition of the present invention contains one or more kinds of the compound of Formula (I) and a salt thereof as an active ingredient, in an amount of 0.01% by weight to 100% by weight, and 0.01% by weight to 50% by weight as an embodiment, even though the amount varies with the route of administration, dosage forms, site of administration, and the type of excipient or additive.

The compound of Formula (I) can be used concurrently with an agent for treating or preventing various diseases considered to be diseases for which the compound of Formula (I) is effective. In concurrent use, the compound and the agent may be administered simultaneously, administered sequentially one at a time, or administered at a desired time interval. The preparation for simultaneous administration may be made into an individual preparation or a pharmaceutical composition that contains various agents for treating or preventing diseases considered to be diseases for which the compound of the Formula (I) is effective and the compound of Formula (I).

EXAMPLES

Hereinafter, the preparation process of the compound of Formula (I) will be described in detail based on examples, but the present invention is not limited to the compound described in the following examples. In addition, the preparation process of starting compounds will be shown respectively in preparation examples. The preparation process of the compound of Formula (I) is not limited to the preparation processes of the specific examples shown below. The compound of Formula (I) can be prepared by combining those preparation processes, or by a method that is clearly known to a person skilled in the art.

In preparation examples, examples, and tables described later, the following abbreviation will be used in some cases.

PEx: a preparation example number (when preparation example numbers are, for example, 39-1 and 39-2, this indicates that these are compounds in the relationship of enantiomers), Ex: an example number (when example numbers are, for example, 5-1 and 5-2, this indicates that these are compounds in the relationship of enantiomers), Str: chemical structural formula, PSyn: preparation method (indicating that the corresponding compound is prepared by the same preparation process as the compound marked with a preparation example number described in the column), Syn: preparation method (indicating that the corresponding compound is prepared by the same preparation process as the compound marked with an example number described in the column), Data: physicochemical data, NMR1: δ (ppm) of a characteristic peak in $^1$H-NMR in DMSO-$d_6$, NMR2: δ (ppm) of a characteristic peak in 1H-NMR in CDCl$_3$, ESI+: a value of m/z in mass spectrometry (ionization ESI, (M+H)$^+$unless otherwise specified), ESI−: indicating a value of m/z (ionization ESI, (M−H)$^-$ unless otherwise specified). In addition, a compound having a symbol of * in the structure thereof represents a single enantiomer. [M] in preparation example and example indicates [mol/L]. [α]D indicates optical rotation, and c indicates a concentration at the time when the optical rotation is measured. Moreover, Temp in the table indicates an extrapolation starting temperature (° C.) in Differential Scanning calorimetry (DSC).

Preparation Example 1

An N,N-dimethylacetamide (25 mL) suspension containing 4-bromo-1-methoxy-5,6,7,8-tetrahydroisoquinoline (2.13 g), zinc powder (115 mg), zinc cyanide (2.07 g), tris(dibenzylideneacetone)dipalladium (0) (201 mg), and 1,1'-bis(diphenylphosphino)ferrocene (244 mg) was stirred for 2 hours at 120° C. in a nitrogen atmosphere, followed by cooling to room temperature. Thereafter, ethyl acetate was added thereto, the insoluble material was removed by filtration with celite, and the resultant was washed with ethyl acetate. The filtrate was washed with diluted aqueous ammonia, water, and saturated brine and dried over anhydrous magnesium sulfate, followed by filtration. The obtained filtrate was concentrated, and the residue was purified by silica gel column chromatography (hexane-ethyl acetate), thereby obtaining 1-methoxy-5,6,7,8-tetrahydroisoquinoline-4-carbonitrile (992 mg) as pale brown powder.

Preparation Example 2

Trimethylsilyl chloride (0.564 mL) was added to an acetonitrile (10 mL) suspension containing 1-methoxy-5,6,7,8-tetrahydroisoquinoline-4-carbonitrile (420 mg) and potassium iodide (741 mg), and the resultant was stirred for 4 hours at 70° C. followed by cooling to room temperature. Thereafter, water was added thereto followed by extraction with ethyl acetate. The organic layer was washed with water and saturated brine and dried over anhydrous magnesium sulfate, followed by filtration. The obtained filtrate was concentrated, and the residue was suspended in chloroform. The insoluble solids were collected by filtration, thereby obtaining 1-oxo-1,2,5,6,7,8-hexahydroisoquinoline-4-carbonitrile (74 mg) as pale yellow powder. The filtrate was concentrated, and the residue was suspended in ethyl acetate. The insoluble solids were collected by filtration, thereby obtaining 1-oxo-1,2,5,6,7,8-hexahydroisoquinoline-4-carbonitrile (201 mg) as red powder. The filtrate was concentrated, and the residue was purified by silica gel column chromatography (chloroform-methanol), thereby obtaining 1-oxo-1,2,5,6,7,8-hexahydroisoquinoline-4-carbonitrile (15 mg) as pale brown powder.

Preparation Example 3

A mixture of 1-oxo-1,2,5,6,7,8-hexahydroisoquinoline-4-carbonitrile (290 mg) and phosphorus oxychloride (8.23 g) was heated under reflux for 3 hours. The reaction mixture was concentrated and water was added to the residue followed by extraction with ethyl acetate. The organic layer was washed with water and saturated brine and dried over anhydrous magnesium sulfate, followed by filtration. The obtained filtrate was concentrated, thereby obtaining 1-chloro-5,6,7,8-tetrahydroisoquinoline-4-carbonitrile (320 mg) as yellow solids.

Preparation Example 4

A mixture of 1-chloro-5,6,7,8-tetrahydroisoquinoline-4-carbonitrile (315 mg), 3-chloroaniline (1 g), and N-methylpyrrolidone (5 mL) was stirred for 4 hours at 180° C. followed by cooling to room temperature. Thereafter, water was added thereto followed by extraction with ethyl acetate. The organic layer was washed with water and saturated brine and dried over anhydrous magnesium sulfate, followed by filtration. The obtained filtrate was concentrated, and the residue was purified by silica gel column chromatography (hexane-ethyl acetate), thereby obtaining 1-[(3-chlorophenyl)amino]-5,6,7,8-tetrahydroisoquinoline-4-carbonitrile (225 mg) as pale brown powder.

Preparation Example 5

A mixture of 1-[(3-chlorophenyl)amino]-5,6,7,8-tetrahydroisoquinoline-4-carbonitrile (125 mg) and 50% sulfuric acid aqueous solution (4 mL) was heated under reflux for 7 hours followed by cooling to room temperature. Thereafter, water and chloroform were added thereto, followed by stirring for 10 minutes at room temperature. The insoluble material was collected by filtration and washed with water and chloroform, thereby obtaining 1-[(3-chlorophenyl)amino]-5,6,7,8-tetrahydroisoquinoline-4-carboxylic acid (59.3 mg) as pale brown solids. The aqueous layer of the filtrate was separated, and an aqueous sodium hydroxide solution was added thereto to adjust pH to 3 to 4 followed by extraction with chloroform/methanol (20:1), drying over anhydrous magnesium sulfate, and filtration. The obtained filtrate was concentrated, and a small amount of chloroform was added thereto. The insoluble solids were collected by filtration and washed with diisopropyl ether, thereby obtaining 1-[(3-chlorophenyl)amino]]-5,6,7,8-tetrahydroisoquinoline-4-carboxylic acid (39.4 mg) as pale brown solids. The filtrate was concentrated, and the residue was purified by silica gel column chromatography (chloroform-methanol), thereby obtaining 1-[(3-chlorophenyl)amino]]-5,6,7,8-tetrahydroisoquinoline-4-carboxylic acid (3 mg) as pale brown powder.

Preparation Example 6

Palladium acetate (76.8 mg), diphenylphosphinoferrocene (189 mg), and triethylamine (3 mL) were added to a mixture of 4-bromo-5,6,7,8-tetrahydroisoquinolin-1(2H)-one (1.56 g), ethanol (15.6 mL), and N,N-dimethylformamide (31.2 mL), and the resultant was stirred for 48 hours at 100° C. in a carbon monoxide atmosphere. Water was added to the reaction mixture, and the insoluble material was removed by filtration followed by extraction with ethyl acetate. The organic layer was washed with water and saturated brine and dried over anhydrous sodium sulfate, followed by filtration. The obtained filtrate was concentrated, and the residue was purified by silica gel column chromatography (chloroform-ethyl acetate), thereby obtaining ethyl 1-oxo-1,2,5,6,7,8-hexahydroisoquinoline-4-carboxylate (964 mg) as brown solids.

Preparation Example 7

A mixture of ethyl 1-oxo-1,2,5,6,7,8-hexahydroisoquinoline-4-carboxylate (531 mg) and phosphorus oxychloride (7.1 mL) was stirred for 2 hours at 100° C. The reaction solution was concentrated under reduced pressure, ice and an aqueous sodium hydrogen carbonate solution were added to the residue followed by extraction with ethyl acetate. The organic layer was washed with saturated brine and dried over anhydrous sodium sulfate, followed by filtration. The obtained filtrate was concentrated, thereby obtaining ethyl 1-chloro-5,6,7,8-tetrahydroisoquinoline-4-carboxylate (574 mg) as brown solids.

Preparation Example 8

3-(Trifluoromethyl)phenol (340 µL) was added to a mixture of 60% sodium hydride (120 mg) and N,N-dimethylformamide (10 mL) under ice cooling followed by stirring for 30 minutes at room temperature. Thereafter, ethyl 1-chloro-5,6,7,8-tetrahydroisoquinoline-4-carboxylate (565 mg) was added thereto followed by stirring for 120 hours at 80° C. Water was added to the reaction mixture under ice cooling followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining ethyl 1-[(3-trifluoromethyl)phenoxy]-5,6,7,8-tetrahydroisoquinoline-4-carboxylate (193 mg) as brown solids.

Preparation Example 9

Methyl 2-oxocyclopentane carboxylate (3.41 g) and sodium methoxide (1.77 g) were added to an ethanol (40 mL) suspension containing 3-amino-3-iminopropanamide hydrochloride (3.00 g) followed by heating under reflux for 4.5 hours. The reaction solution was concentrated under reduced pressure, and water was added thereto followed by neutralization with acetic acid. The precipitate was collected by filtration and washed with ethanol, thereby obtaining 3-amino-1-hydroxy-6,7-dihydro-5H-cyclopenta[c]pyridine-4-carboxamide (1.66 g) as colorless solids.

Preparation Example 10

A mixture of 3-amino-1-hydroxy-6,7-dihydro-5H-cyclopenta[c]pyridine-4-carboxamide (1.65 g) and phosphorus oxychloride (8 mL) was heated under reflux for 3 hours. The reaction solution was concentrated under reduced pressure, and the residue was added to ice water followed by neutralization with sodium carbonate and extraction with chloroform. The organic layer was concentrated under reduced pressure, and then the residue was purified by silica gel column chromatography (chloroform:methanol=10:1), thereby obtaining 3-amino-1-chloro-6,7-dihydro-5H-cyclopenta[c]pyridine-4-carbonitrile (725 mg) as pale yellow solids.

Preparation Example 11

Copper powder (39 mg) was added to a mixture of N-amyl nitrite (1.2 mL) and tetrahydrofuran (10 mL) at room temperature, and a mixture of 3-amino-1-chloro-6,7-dihydro-5H-cyclopenta[c]pyridine-4-carbonitrile (598 mg), tetrahydrofuran (15 mL), and N,N-dimethylformamide (15 mL) was further added dropwise thereto. 15 minutes later, the resultant was heated up to 80° C. and stirred for 4 hours at the same temperature. Water was added thereto followed by extraction with ethyl acetate. The organic layer was washed with saturated brine and dried over anhydrous magnesium sulfate, followed by filtration. The obtained filtrate was concentrated, and the residue was purified by silica gel column chromatography (hexane-ethyl acetate=3:1), thereby obtaining 1-chloro-6,7-dihydro-5H-cyclopenta[c]pyridine-4-carbonitrile (394 mg) as white solids.

Preparation Example 12

A mixture of 1-chloro-6,7-dihydro-5H-cyclopenta[c]pyridine-4-carbonitrile (452 mg), 3-chloroaniline (1.45 g), and 1-methyl-2-pyrrolidone (7 mL) was stirred for 4 hours at 180° C. Water was added to the reaction mixture, followed by stirring for an hour. Thereafter, the precipitated solids were collected by filtration and washed with water and subsequently with a mixture of hexane:ethyl acetate (4:1), followed by drying under reduced pressure, thereby obtaining 1-[(3-chlorophenyl)amino]-6,7-dihydro-5H-cyclopenta[c]pyridine-4-carbonitrile (633 mg) as pale brown solids.

Preparation Example 13

A mixture of 1-[(3-chlorophenyl)amino]-6,7-dihydro-5H-cyclopenta[c]pyridine-4-carbonitrile (633 mg), sulfuric acid (6 mL), and water (6 mL) was stirred for 10 hours at 120° C. After the reaction mixture was left to cool, ice water was added thereto followed by neutralization with an aqueous sodium hydroxide solution and stirring for an hour at room temperature. The precipitated solids were collected by filtration and washed with water and subsequently with a mixture of hexane:ethyl acetate (3:1), followed by drying under reduced pressure, thereby obtaining 1-[(3-chlorophenyl)amino]-6,7-dihyrdo-5H-cyclopenta[c]pyridine-4-carboxylic acid (618 mg) as pale grey solids.

Preparation Example 14

A mixture of 1-(methylsulfanyl)-5,6,7,8-tetrahydro-5,8-methanoisoquinoline (280 mg) and chloroform (5 mL) was added dropwise to a mixture of 3-chloroperbenzoic acid (340 mg) and chloroform (10 mL) under ice cooling. The reaction mixture was stirred for 2 hours at room temperature, and then a saturated aqueous sodium carbonate solution was added thereto. The aqueous layer was extracted with chloroform, and the organic layer was washed with water. The organic layer was dried over anhydrous magnesium sulfate, followed by filtration and concentration, thereby obtaining 1-(methylsulfinyl)-5,6,7,8-tetrahydro-5,8-methanoisoquinoline (303 mg) as pale yellow oil.

Preparation Example 15

28% Sodium methoxide (4 mL) was added to a mixture of 1-(methylsulfinyl)-5,6,7,8-tetrahydro-5,8-methanoisoquinoline (303 mg) and methanol (2 mL), and the resultant was heated under reflux for 15 hours. The reaction mixture was concentrated, and the residue was purified by silica gel column chromatography (hexane-ethyl acetate), thereby obtaining 1-methoxy-5,6,7,8-tetrahydro-5,8-methanoisoquinoline (256 mg) as pale yellow oil.

Preparation Example 16

N-bromosuccinimide (286 mg) was added to a mixture of 1-methoxy-5,6,7,8-tetrahydro-5,8-methanoisoquinoline (256 mg) and chloroform (4 mL), and the resultant was stirred for 36 hours at room temperature. The reaction mixture was concentrated, and the residue was purified by silica gel column chromatography (hexane-ethyl acetate), thereby obtaining 4-bromo-1-methoxy-5,6,7,8-tetrahydro-5,8-methanoisoquinoline (286 mg) as colorless oil.

Preparation Example 17

Palladium acetate (13 mg), diphenylphosphinoferrocene (31 mg), and triethylamine (470 μL) were added to a mixture of 4-bromo-1-methoxy-5,6,7,8-tetrahydro-5,8-methanoisoquinoline (286 mg), ethanol (3 mL), and N,N-dimethylformamide (6 mL), and the resultant was stirred for 15 hours at 100° C. in a carbon monoxide atmosphere. Water was added to the reaction mixture followed by extraction with ethyl acetate. The organic layer was washed with water and saturated brine and dried over anhydrous magnesium sulfate, followed by filtration. The obtained filtrate was concentrated, and the residue was purified by silica gel column chromatography (hexane-ethyl acetate), thereby obtaining ethyl 1-methoxy-5,6,7,8-tetrahydro-5,8-methanoisoquinoline-4-carboxylate (140 mg) as colorless oil.

Preparation Example 18

Sodium iodide (96 mg) and trimethylsilyl chloride (81 μL) were added to a mixture of ethyl 1-methoxy-5,6,7,8-tetrahydro-5,8-methaisoquinoline-4-carboxylate (140 mg) and acetonitrile (4 mL) followed by stirring for 4 hours at room temperature and for 15 hours at 50° C. Water was added to the reaction mixture followed by extraction with ethyl acetate. The organic layer was washed with water and saturated brine and dried over anhydrous magnesium sulfate, followed by filtration. The obtained filtrate was concentrated, thereby obtaining ethyl 1-oxo-1,2,5,6,7,8-hexahydro-5,8-methanoisoquinoline-4-carboxylate (134 mg) as brown solids.

Preparation Example 19

A mixture of ethyl 1-oxo-1,2,5,6,7,8-hexahydro-5,8-methaisoquinoline-4-carboxylate (2.04 g) and phosphorus oxychloride (12 mL) was stirred for an hour at 100° C. The reaction solution was concentrated under reduced pressure, an aqueous sodium hydrogen carbonate solution was added to the residue followed by extraction with ethyl acetate. The organic layer was washed with saturated brine and dried over anhydrous sodium sulfate, followed by filtration. The obtained filtrate was concentrated, thereby obtaining ethyl 1-chloro-5,6,7,8-tetrahydro-5,8-methanoisoquinoline-4-carboxylate (1.75 g) as brown solids.

Preparation Example 20

A mixture of ethyl 1-chloro-5,6,7,8-tetrahydro-5,8-methanoisoquinoline-4-carboxylate (674 mg), 3-(trifluoromethyl)aniline (1 mL), and 1-methyl-2-pyrrolidone (3.4 mL) was stirred for 12 hours at 180° C. Water was added to the reaction mixture followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining ethyl 1-{[3-(trifluoromethyl)phenyl]amino}-5,6,7,8-tetrahydro-5,8-methanoisoquinoline-4-carboxylate (1.0 g) as yellow solids.

Preparation Example 21

A mixture of ethyl 1-chloro-5,6,7,8-tetrahydro-5,8-methanisoquinoline-4-carboxylate (700 mg), 3-chloro-4-fluoroaniline (486 mg), a 4 M hydrogen chloride/dioxane solution (139 μL), and N-methylpyrrolidone (3.5 mL) was stirred for 48 hours at 120° C. Water was added to the reaction mixture followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining ethyl 1-[(3-chloro-4-fluorophenyl)amino]-5,6,7,8-tetrahydro-5,8-methanoisoquinoline-4-carboxylate (878 mg) as white solids.

Preparation Example 22

A 1 M aqueous sodium hydroxide solution (6 mL) was added to a mixture of ethyl 1-{[3-(trifluoromethyl)phenyl]amino}-5,6,7,8-tetrahydro-5,8-methanoisoquinoline-4-carboxylate (1.0 g), ethanol (5 mL), and tetrahydrofuran (5 mL), and the resultant was stirred for 16 hours at room temperature. The reaction solution was concentrated under reduced pressure, water was added to the residue, and the resultant was washed with ether. 1 M hydrochloric acid was added to the aqueous layer until the pH became 1 followed by extraction with chloroform. The organic layer was washed with saturated brine and dried over anhydrous sodium sulfate, followed by filtration. The obtained filtrate was concentrated, and the residue was washed with hexane-ethyl acetate (4:1), thereby obtaining 1-{[3-(trifluoromethyl)phenyl]amino}-5,6,7,8-tetrahydro-5,8-methanoisoquinoline-4-carboxylic acid (659 mg) as yellow solids.

Preparation Example 23

Bicyclo[2.2.2]octa-2-ene (25 g) was added to a mixture of 3-(methylsulfanyl)-1,2,4-triazine (16.6 g) and toluene (16.6 mL) followed by stirring for 18 hours at 180° C. in a sealed tube. The obtained reaction mixture was purified by silica gel column chromatography (hexane-ethyl acetate), thereby obtaining 1-(methylsulfanyl)-5,6,7,8-tetrahydro-5,8-ethanoisoquinoline (10.4 g) as pale yellow oil.

Preparation Example 24

Sodium periodate (12 g) was added to a mixture of 1-(methylsulfanyl)-5,6,7,8-tetrahydro-5,8-ethanoisoquinoline (10.4 g), tetrahydrofuran (40 mL), methanol (40 mL), and water (40 mL) under ice cooling followed by stirring for 15 hours at 50° C. After the insoluble material was separated by filtration, the organic solvent was evaporated under reduced pressure, and the remaining aqueous layer was extracted with ethyl acetate. The organic layer was washed with water and saturated brine and dried over anhydrous magnesium sulfate, followed by filtration. The obtained filtrate was concentrated, thereby obtaining 1-(methylsulfinyl)-5,6,7,8-tetrahydro-5,8-ethanoisoquinoline (8.05 g) as pale yellow oil.

Preparation Example 25

2,2'-Bis(diphenylphosphino)-1,1'-binaphthyl (205 mg), sodium tert-butoxide (794 mg), and tris(dibenzylideneacetone)dipalladium (76 mg) were added to a mixture of 4-bromo-1-methoxy-5,6,7,8-tetrahydroisoquinoline (1 g), 3-chloroaniline (518 µL), and toluene (15 mL) followed by stirring for 16 hours at 100° C. in an argon atmosphere. Saturated brine was added to the reaction solution, the insoluble material was separated by filtration, and then the filtrate was extracted with ethyl acetate. The organic layer was dried over anhydrous sodium sulfate, followed by filtration. The obtained filtrate was concentrated, and the residue was purified by silica gel column chromatography (hexane-ethyl acetate), thereby obtaining N-(3-chlorophenyl)-1-methoxy-5,6,7,8-tetrahydroisoquinoline-4-amine (1.02 g) as reddish brown oil.

Preparation Example 26

Potassium iodide (1.76 g) and trimethylsilyl chloride (1.34 mL) were added to a mixture of N-(3-chlorophenyl)-1-methoxy-5,6,7,8-tetrahydroisoquinoline-4-amine (1.02 g) and acetonitrile (10 mL) followed by stirring for 18 hours at 70° C. Water was added to the reaction solution, and the resulting solids were collected by filtration and washed with ethyl acetate. Thereafter, the resultant was dried under reduced pressure, thereby obtaining 4-[(3-chlorophenyl)amino]-5,6,7,8-tetrahydroisoquinolin-1(2H)-one as white solids. The filtrate was concentrated, and the residue was purified by silica gel column chromatography (methanol-chloroform) and mixed with the solids obtained previously, thereby obtaining 4-[(3-chlorophenyl)amino]-5,67,8-tetrahydroisoquinolin-1(2H)-one (792 mg) as white solids.

Preparation Example 27

A mixture of 4-[(3-chlorophenyl)amino]-5,6,7,8-tetrahydroisoquinolin-1(2H)-one (792 mg) and phosphorus oxychloride (3 mL) was stirred for 20 hours at 120° C. After the reaction solution was concentrated, water was added to the residue followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining 1-chloro-N-(3-chlorophenyl)-5,6,7,8-tetrahydroisoquinoline-4-amine (187 mg) as yellow oil.

Preparation Example 28

Zinc cyanide (150 mg), diphenylphosphinoferrocene (18 mg), and tris(dibenzylideneacetone)dipalladium (15 mg) were added to a mixture of 1-chloro-N-(3-chlorophenyl)-5,6,7,8-tetrahydroisoquinoline-4-amine (187 mg) and N-methylpyrrolidone (3 mL) followed by stirring for 18 hours at 120° C. in an argon atmosphere. Water was added to the reaction solution, the insoluble material was separated by filtration, and then the filtrate was extracted with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining 4-[(3-chlorophenyl)amino]-5,6,7,8-tetrahydroisoquinoline-1-carbonitrile (99 mg) as pale yellow solids.

Preparation Example 29

An aqueous sodium hydroxide solution (15 wt %, 3 mL) was added to a mixture of 4-[(3-chlorophenyl)amino]-5,6,7,8-tetrahydroisoquinoline-1-carbonitrile (98 mg) and ethanol (2 mL), and the resultant was stirred for 2 days at 80° C. The reaction solution was cooled to 0° C., and 1 M hydrochloric acid was added thereto until the pH became 3. The resulting solids were collected by filtration, washed with water, and then dried under reduced pressure, thereby obtaining 4-[(3-chlorophenyl)amino]-5,6,7,8-tetrahydroisoquinoline-1-carboxylic acid (80 mg) as pale yellow solids.

Preparation Example 30

Cesium carbonate (2.02 g), N,N-dimethylglycine (160 mg), and copper iodide (98 mg) were added to a mixture of 4-bromo-1-methoxy-5,6,7,8-tetrahydroisoquinoline (500 mg), 3-(trifluoromethyl)phenol (369 µL), and dioxane (7.5 mL), and the resultant was stirred for 3 days at 100° C. in an argon atmosphere. Water was added to the reaction solution followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining 1-methoxy-4-[3-(trifluoromethyl)phenoxy]-5,6,7,8-tetrahydroisoquinoline (278 mg) as pale yellow oil.

Preparation Example 31

In an argon atmosphere, a mixture of 3-chlorobenzene thiol (480 μL) and dioxane (2 mL) was added to a mixture of 4-bromo-1-methoxy-5,6,7,8-tetrahydroisoquinoline (1 g), sodium tert-butoxide (595 mg), bis[2-(diphenylphosphino)phenyl]ether (133 mg), palladium acetate (46 mg), and dioxane (8 mL) at room temperature followed by stirring for 24 hours at 100° C. Water was added to the reaction solution followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining 4-[3-(chlorophenyl)sulfanyl]-1-methoxy-5,6,7,8-tetrahydroisoquinoline (628 mg) as colorless oil.

Preparation Example 32

Lawesson's reagent (620 mg) was added to a mixture of 4-bromo-5,6,7,8-tetrahydroisoquinolin-1(2H)-one (500 mg) and toluene (20 mL) followed by stirring for 4 hours at 130° C. in an argon atmosphere. After the reaction solution was concentrated, the residue was purified by silica gel column chromatography (hexane-ethyl acetate) and further washed with ethyl acetate-hexane (1:1), thereby obtaining 4-bromo-5,6,7,8-tetrahydroisoquinoline-1(2H)-thione (314 mg) as yellow solids.

Preparation Example 33

A 10% aqueous sodium hypochlorite solution (2 mL) was added dropwise to a mixture of 4-bromo-5,6,7,8-tetrahydroisoquinoline-1(2H)-thione (150 mg), dichloromethane (2 mL), water (2 mL), and concentrated hydrochloric acid (600 μL) over 5 minutes under ice cooling and vigorous stirring followed by stirring for another 45 minutes. The reaction solution was extracted with dichloromethane, and the organic layer was washed with saturated brine and dried over anhydrous sodium sulfate, followed by filtration. The obtained filtrate was concentrated, thereby obtaining a crude product of 4-bromo-5,6,7,8-tetrahydroisoquinoline-1-sulfonyl chloride. A mixture of the obtained crude product of 4-bromo-5,6,7,8-tetrahydroisoquinoline-1-sulfonyl chloride and dichloromethane (2 mL) was added dropwise to a mixture of morpholine (80 μL), triethylamine (257 μL), and dichloromethane (2 mL) under ice cooling followed by stirring for 18 hours at room temperature. A saturated aqueous sodium hydrogen carbonate solution was added to the reaction solution followed by extraction with chloroform. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining 4-bromo-1-(morpholin-4-ylsulfonyl)-5,6,7,8-tetrahydroisoquinoline (131 mg) as white solids.

Preparation Example 34

2,2'-Bis(diphenylphosphino)-1,1'-binaphthyl (126 mg), sodium tert-butoxide (486 mg), and tris(dibenzylideneacetone)dipalladium (46 mg) were added to a mixture of 4-bromo-1-methoxy-5,6,7,8-tetrahydro-5,8-methanoisoquinoline (642 mg), 3-(trifluoromethoxy)aniline (388 μL), and toluene (10 mL) followed by stirring for 16 hours at 100° C. in an argon atmosphere. Saturated brine was added to the reaction solution, the insoluble material was separated by filtration, and the filtrate was extracted with ethyl acetate. The organic layer was dried over anhydrous sodium sulfate, followed by filtration. The obtained filtrate was concentrated, and the residue was purified by silica gel column chromatography (hexane-ethyl acetate), thereby obtaining 1-methoxy-N-[3-(trifluoromethoxy)phenyl]-5,6,7,8-tetrahydro-5,8-methanoisoquinoline-4-amine (839 mg) as reddish brown oil.

Preparation Example 35

Sodium iodide (896 mg) and trimethylsilyl chloride (756 μL) were added to a mixture of 1-methoxy-N-[3-(trifluoromethoxy)phenyl]-5,6,7,8-tetrahydro-5,8-methanoisoquinoline-4-amine (838 mg) and acetonitrile (10 mL), and the resultant was stirred overnight at 60° C. An aqueous sodium hydrogen carbonate solution was added to the reaction solution followed by extraction with ethyl acetate. The organic layer was washed with saturated brine and dried over anhydrous sodium sulfate, followed by filtration. The obtained filtrate was concentrated, and the residue was purified by silica gel column chromatography (methanol-chloroform), thereby obtaining 4-{[3-(trifluoromethoxy)phenyl]amino}-5,6,7,8-tetrahydro-5,8-methanoisoquinolin-1(2H)-one (613 mg) as white solids.

Preparation Example 36

Trifluoromethanesulfonic anhydride (337 μL) was added to a mixture of 4-{[3-(trifluoromethoxy)phenyl]amino}-5,6,7,8-tetrahydro-5,8-methanoisoquinolin-1(2H)-one (613 mg), pyridine (2 mL), and dichloromethane (6 mL) under ice cooling followed by stirring for an hour. The reaction solution was concentrated, and ethyl acetate and a saturated aqueous sodium hydrogen carbonate solution were added to the residue followed by extraction with ethyl acetate. The organic layer was washed with saturated brine and dried over anhydrous sodium sulfate, followed by filtration. Toluene was added to the obtained filtrate, and the filtrate was concentrated. This operation was repeated three times, thereby obtaining 4-{[3-(trifluoromethoxy)phenyl]amino}-5,6,7,8-tetrahydro-5,8-methanoisoquinolin-1-yl trifluoromethanesulfonate (850 mg) as brown oil.

Preparation Example 37

Palladium acetate (20 mg), diphenylphosphinoferrocene (50 mg), and triethylamine (759 μL) were added to a mixture of 4-{[3-(trifluoromethoxy)phenyl]amino}-5,6,7,8-tetrahydro-5,8-methanoisoquinolin-1-yl trifluoromethanesulfonate (850 mg), ethanol (4 mL), and N,N-dimethylformamide (8 mL) followed by stirring for 14 hours at 100° C. in a carbon monoxide atmosphere. Water was added to the reaction mixture followed by extraction with ethyl acetate. The organic layer was washed with water and saturated brine and dried over anhydrous sodium sulfate, followed by filtration. The obtained filtrate was concentrated, and the residue was purified by silica gel column chromatography (hexane-ethyl acetate), thereby obtaining ethyl 4-{[3-(trifluoromethoxy)phenyl]amino}-5,6,7,8-tetrahydro-5,8-methanoisoquinoline-1-carboxylate (665 mg) as white solids.

Preparation Example 38

An aqueous sodium hydroxide solution (15 wt %, 3 mL) was added to a mixture of ethyl 4-{[3-(trifluoromethoxy)

phenyl]amino}-5,6,7,8-tetrahydro-5,8-methanoisoquinoline-1-carboxylate (660 mg) and ethanol (8 mL) followed by stirring for 3 hours at 60° C. After ethanol in the reaction solution was evaporated, the remaining aqueous solution was cooled to 0° C., and 1 M hydrochloric acid was added thereto until the pH became 3. After sodium chloride was added thereto to saturate the solution followed by extraction with a mixture of methanol-chloroform (1:10). The organic layer was dried over anhydrous sodium sulfate, followed by filtration and concentration, thereby obtaining 4-{[3-(trifluoromethoxy)phenyl]amino}-5,6,7,8-tetrahydro-5,8-methanoisoquinoline-1-carboxylic acid (605 mg) as pale yellow solids.

Preparation Example 39

Concentrated hydrochloric acid (3 mL) was added to a mixture of 1-methoxy-N-(3-methoxyphenyl)-5,6,7,8-tetrahydro-5,8-methanoisoquinoline-4-amine (526 mg), dioxane (1 mL), and water (1 mL) followed by stirring for 36 hours at 100° C. An aqueous sodium hydroxide solution (15 wt %) was added to the reaction solution until the pH became 9, and the resulting solids were collected by filtration and washed with water and ethyl acetate, thereby obtaining 4-[(3-methoxyphenyl)amino]-5,6,7,8-tetrahydro-5,8-methanoisoquinolin-1(2H)-one (291 mg) as white solids.

Preparation Example 40

A mixture of ethyl 1-oxo-1,2,5,6,7,8-hexahydro-5,8-methanoisoquinoline-4-carboxylate (171 mg) and phosphorus oxychloride (1.3 mL) was stirred for 3 hours at 110° C. The reaction solution was concentrated under reduced pressure, toluene (10 mL) was added to the residue, and azeotropic operation was repeated three times. An aqueous sodium hydrogen carbonate solution was added to the residue followed by extraction with ethyl acetate. The organic layer was washed with saturated brine and dried over anhydrous sodium sulfate, followed by filtration and concentration. 3-Chloroaniline (77 µL) and N-methylpyrrolidone (1.5 mL) were added to the obtained yellow oil followed by stirring for 7 hours at 180° C. Water was added to the reaction mixture followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining ethyl 1-{[3-chlorophenyl]amino}-5,6,7,8-tetrahydro-5,8-methanoisoquinoline-4-carboxylate (262 mg) as pale yellow solids.

Preparation Example 41

2,2'-Bis(diphenylphosphino)-1,1'-binaphthyl (118 mg), sodium tert-butoxide (459 mg), and tris(dibenzylideneacetone)dipalladium (43 mg) were added to a mixture of 4-bromo-1-methoxy-5,6,7,8-tetrahydro-5,8-methanoisoquinoline (599 mg), 3-(trifluoromethyl)aniline (330 µL), and toluene (2 mL) followed by stirring for 30 minutes at 150° C. by being irradiated with microwaves in an argon atmosphere. Saturated brine was added to the reaction solution, the insoluble material was separated by filtration, and then the filtrated was extracted with ethyl acetate. The organic layer was dried over anhydrous sodium sulfate, followed by filtration. The obtained filtrate was concentrated, and the residue was purified by silica gel column chromatography (hexane-ethyl acetate), thereby obtaining 1-methoxy-N-[3-(trifluoromethyl)phenyl]-5,6,7,8-tetrahydro-5,8-methanoisoquinoline-4-amine (818 mg) as yellow oil.

Preparation Example 42

1,3-Bis(2,6-diisopropylphenyl)-1H-imidazol-3-ium hydrochloride (459 mg), palladium (II) acetate (133 mg), and sodium tert-butoxide (809 mg) were added to a mixture of 4-bromo-1-methoxy-5,6,7,8-tetrahydro-5,8-ethanoisoquinoline (1.5 g), 3-aminoadamantan-1-yl-acetate (1.40 g), and toluene (10 mL) followed by stirring for 30 minutes at 150° C. by being irradiated with microwaves in an argon atmosphere. Saturated brine was added to the reaction solution, the insoluble material was separated by filtration, and then the filtrate was extracted with ethyl acetate. The organic layer was dried over anhydrous sodium sulfate, followed by filtration. The obtained filtrate was concentrated, and the residue was purified by silica gel column chromatography (hexane-ethyl acetate), thereby obtaining 3-[(1-methoxy-5,6,7,8-tetrahydro-5,8-ethanoisoquinolin-4-yl)amino]adamantan-1-yl acetate (776 mg) as a brown foam.

Preparation Example 43

Sodium borohydride (43.6 mg) was added to a mixture of ethyl 4-[(3,5-difluoroadamantan-1-yl)amino]-5,6,7,8-tetrahydroisoquinoline-1-carboxylate (150 mg), calcium chloride (128 mg), and ethanol (3 mL) under ice cooling, and the resultant was stirred for 3 days at room temperature. Water was added to the reaction mixture followed by extraction with ethyl acetate. The organic layer was washed with saturated brine and dried over anhydrous sodium sulfate, followed by filtration. The obtained filtrate was concentrated, thereby obtaining {4-[(3,5-difluoroadamantan-1-yl)amino]-5,6,7,8-tetrahydroisoquinolin-1-yl}methanol (133 mg) as white solids.

Preparation Example 44

A mixture of ethyl 1-chloro-5,6,7,8-tetrahydroisoquinoline-4-carboxylate (455 mg), 3-(trifluoromethoxy)aniline (1.0 g), and 1-methyl-2-pyrrolidone (2 mL) was stirred for an hour at 180° C. by being irradiated with microwaves. Water was added to the reaction mixture followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining ethyl 1-{[3-(trifluoromethoxy)phenyl]amino}-5,6,7,8-tetrahydroisoquinoline-4-carboxylate (269 mg) as white solids.

Preparation Example 45

Trifluoromethanesulfonic anhydride (750 µL) was added to a mixture of ethyl 1-oxo-1,2,5,6,7,8-hexahydroisoquinoline-4-carboxylate (800 mg), triethylamine (1.5 mL), and dichloromethane (16 mL) under ice cooling followed by stirring for an hour. A saturated aqueous sodium hydrogen carbonate solution was added to the reaction solution followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining ethyl 1-{[(trifluoromethyl)sulfonyl]oxy}-5,6,7,8-tetrahydroisoquinoline-4-carboxylate (1.06 g) as yellow oil.

Preparation Example 46

A mixture of ethyl 1-{[(trifluoromethyl)sulfonyl]oxy}-5,6,7,8-tetrahydroisoquinoline-4-carboxylate (1.01 g), 3,3-dimethylcyclohexylamine hydrochloride (702 mg), diisopropylethylamine (1.5 mL), molecular sieves 4A (5.05 g), and N-methylpyrrolidone (15 mL) was stirred for 5.5 hours at 180° C. Ethyl acetate was added to the reaction mixture, the insoluble material was separated by filtration, and then the filtrate was washed with water. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining ethyl 1-[(3,3-dimethylcyclohexyl)amino]-5,6,7,8-tetrahydroisoquinoline-4-carboxylate (915 mg) as pale yellow oil.

Preparation Example 47

Trifluoromethanesulfonic anhydride (640 µL) was added to a mixture of ethyl 1-oxo-1,2,5,6,7,8-hexahydro-5,8-methanoisoquinoline-4-carboxylate (740 mg), triethylamine (1.3 mL), and dichloromethane (15 mL) under ice cooling followed by stirring for 1.5 hours. A saturated aqueous sodium hydrogen carbonate solution was added to the reaction solution followed by extraction with ethyl acetate. The organic layer was washed with saturated brine and dried over anhydrous sodium sulfate, followed by filtration and concentration. 3-Aminoadamantan-1-ol (796 mg), diisopropylethylamine (1.63 mL), molecular sieves A4 (5 g), and N-methylpyrrolidone (5 mL) were added to the obtained brown oil followed by stirring for 16 hours at 180° C. Ethyl acetate was added to the reaction mixture, the insoluble material was separated by filtration, and then the filtrate was washed with water. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining ethyl 1-[(3-hydroxyadamantan-1-yl)amino]-5,6,7,8,-tetrahydro-5,8-methanoisoquinoline-4-carboxylate (393 mg) as pale yellow oil.

Preparation Example 48

4-Chloro-5,6,7,8-tetrahydro-5,8-ethanophthalazine-1-carbonitrile (730 mg) was suspended in 1,4-dioxane (12 mL), 3-chloroaniline (1.27 g) and a 4 M hydrogen chloride/dioxane solution (0.83 mL) was added thereto followed by reaction for an hour at 150° C. by being irradiated with microwaves. After the reaction solution was cooled, ethyl acetate and an aqueous sodium hydrogen chloride solution were added thereto to perform liquid separation. The organic layer was washed with saturated brine and then dried over anhydrous magnesium sulfate, followed by filtration, and the solvent was evaporated under reduced pressure. The residue was purified by silica gel column chromatography (hexane-ethyl acetate), thereby obtaining 4-[(3-chlorophenyl)amino]-5,6,7,8-tetrahydro-5,8-ethanophthalazine-1-carbonitrile (550 mg) as pale brown powder.

Preparation Example 49

A mixture of 4-[(3-chlorophenyl)amino]-5,6,7,8-tetrahydro-5,8-ethanophthalazine-1-carbonitrile (649 mg), 1,4-dioxane (3 mL), and a 5 M aqueous sodium hydroxide solution (2.1 mL) was heated under reflux for 8 hours followed by cooling to room temperature. Ethyl acetate and water were added thereto, and the pH thereof was adjusted to 2 by using 6 M hydrochloric acid, followed by liquid separation. The organic layer was washed with water and saturated brine and then dried over anhydrous magnesium sulfate, followed by filtration. Thereafter, the solvent was evaporated under reduced pressure. The residue was purified by silica gel column chromatography (hexane-ethyl acetate), thereby obtaining 4-[(3-chlorophenyl)amino]-5,6,7,8-tetrahydro-5,8-ethanophthalazine-1-carboxylic acid (140 mg) as pale brown powder.

Preparation Example 50

A mixture of ethyl 1-methoxy-5,6,7,8-tetrahydro-5,8-methanoisoquinoline-4-carboxylate (2.75 g), ethanol (25 mL), and an aqueous sodium hydroxide solution (15 wt %, 17 mL) was stirred for 16 hours at room temperature. The reaction solution was concentrated under reduced pressure, the residue was dissolved in water, and 1 M hydrochloric acid was added thereto until the pH became 1. The resulting solids were collected by filtration and dried, thereby obtaining 1-methoxy-5,6,7,8-tetrahydro-5,8-methanoisoquinoline-4-carboxylic acid (2.35 g) as white solids.

Preparation Example 51

A mixture of 1-methoxy-5,6,7,8-tetrahydro-5,8-methanoisoquinoline-4-carboxylic acid (2.49 g), (1R,2S,5R)-2-isopropyl-5-methylcyclohexanol (1.95 g), N-[3-(dimethylamino)propyl]-N'-ethylcarbodiimide hydrochloride (2.61 g), N,N-dimethylaminopyridine (1.66 g), and dichloromethane (25 mL) was stirred for 6 hours at room temperature. Water was added to the reaction solution, and extraction was performed with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining (1R,2S,5R)-2-isopropyl-5-methylcyclohexyl 1-methoxy-5,6,7,8-tetrahydro-5,8-methanoisoquinoline-4-carboxylate (3.9 g) as colorless oil. The (1R,2S,5R)-2-isopropyl-5-methylcyclohexyl 1-methoxy-5,6,7,8-tetrahydro-5,8-methanoisoquinoline-4-carboxylate (4.22 g) as a diastereomer mixture was purified by silica gel column chromatography (hexane-toluene), thereby obtaining a low-polarity diastereomer (1.53 g) of (1R,2S,5R)-2-isopropyl-5-methylcyclohexyl-1-methoxy-5,6,7,8-tetrahydro-5,8-methanoisoquinoline-4-carboxylate as colorless oil.

Preparation Example 52

Sodium iodide (784 mg) and trimethylsilyl chloride (635 µL) were added to a mixture of the low-polarity diastereomer (1.53 g) of (1R,2S,5R)-2-isopropyl-5-methylcyclohexyl 1-methoxy-5,6,7,8-tetrahydro-5,8-methanoisoquinoline-4-carboxylate and acetonitrile (30 mL) followed by stirring for an hour at 100° C. and cooling to room temperature. Thereafter, water was added thereto followed by extraction with ethyl acetate. The organic layer was washed with water and saturated brine and dried over anhydrous sodium sulfate, followed by filtration. The obtained filtrate was concentrated, thereby obtaining (1R,2S,5R)-2-isopropyl-5-methylcyclohexyl 1-oxo-1,2,5,6,7,8-hexahydro-5,8-methanoisoquinoline-4-carboxylate (1.41 g) as brown solids.

Preparation Example 53

A mixture of (1R,2S,5R)-2-isopropyl-5-methylcyclohexyl 1-oxo-1,2,5,6,7,8-hexahydro-5,8-methanoisoquinoline-4-carboxylate (1.4 g) and phosphorus oxychloride (9 mL) was stirred for 1.5 hours at 100° C. The reaction solution was concentrated under reduced pressure, an aqueous sodium hydrogen carbonate solution was added to the residue followed by extraction with ethyl acetate. The organic layer was washed with saturated brine and dried over anhydrous sodium sulfate, followed by filtration. The obtained filtrate was concentrated, thereby obtaining (1R,2S,5R)-2-isopropyl-5-methylcyclohexyl 1-chloro-5,6,7,8-tetrahydro-5,8-methanoisoquinoline-4-carboxylate (1.47 g) as brown solids.

Preparation Example 54

A mixture of (1R,2S,5R)-2-isopropyl-5-methylcyclohexyl 1-chloro-5,6,7,8-tetrahydro-5,8-methanoisoquinoline-4-carboxylate (755 mg), 3-chloroaniline (660 µL), and 1-methyl-2-pyrrolidone (4 mL) was stirred for 12 hours at 180° C. Water was added to the reaction mixture followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining (1R,2S,5R)-2-isopropyl-5-methylcyclohexyl 1-[(3-chlorophenyl)amino]-5,6,7,8-tetrahydro-5,8-methanoisoquinoline-4-carboxylate (899 mg) as yellow solids.

Preparation Example 55

A mixture of (1R,2S,5R)-2-isopropyl-5-methylcyclohexyl 1-[(3-chlorophenyl)amino]-5,6,7,8-tetrahydro-5,8-methanoisoquinoline-4-carboxylate (890 mg), ethanol (6 mL), tetrahydrofuran (6 mL), and an aqueous sodium hydroxide solution (15 wt %, 4 mL) was stirred for 5 days at 60° C. The reaction solution was concentrated under reduced pressure, water was added to the residue followed by washing with a mixture of ether and hexane. 1 M hydrochloric acid was added to the aqueous layer until the pH became 1 followed by extraction with chloroform. The organic layer was washed with saturated brine and dried over anhydrous sodium sulfate, followed by filtration and concentration, thereby obtaining 1-[(3-chlorophenyl)amino]-5,6,7,8-tetrahydro-5,8-methanoisoquinoline-4-carboxylic acid (584 mg) as pale yellow solids.

Preparation Example 56

Sodium iodide (1.87 g) and 57% hydriodic acid (3.3 mL) were added to 1,4-dichloro-5,6,7,8-tetrahydro-5,8-ethanophthalazine (1.15 g), and the resultant was reacted for 40 minutes at 120° C. by using a microwave reactor. After being cooled, the reaction solution was suspended in a 10% aqueous sodium thiosulfate solution together with ethyl acetate, and the insoluble material was separated by filtration with celite. Liquid separation was performed and the organic layer was washed with saturated brine and then dried over anhydrous magnesium sulfate, followed by filtration. The solvent was evaporated under reduced pressure, and the residue was purified by silica gel column chromatography (hexane-ethyl acetate), thereby obtaining 1-chloro-4-iodo-5,6,7,8-tetrahydro-5,8-ethanophthalazine (1.37 g) as yellow powder.

Preparation Example 57

Copper (I) cyanide (754 mg) was added to a mixture of 1-chloro-4-iodo-5,6,7,8-tetrahydro-5,8-ethanophthalazine (1.35 g) and acetonitrile (13 mL) followed by stirring for 40 minutes at 160° C. by using a microwave reactor and cooling to room temperature. Thereafter, ethyl acetate and water were added thereto to dissolve the target substance, and the insoluble material was separated by filtration with celite. The organic layer was washed with saturated brine and then dried over anhydrous magnesium sulfate, followed by filtration. Thereafter, the solvent was evaporated under reduced pressure, and the residue was purified by silica gel column chromatography (eluent: hexane-ethyl acetate), thereby obtaining 4-chloro-5,6,7,8-tetrahydro-5,8-ethanophthalazine-1-carbonitrile (750 mg) as pale yellow powder.

Preparation Example 58

From 4-bromo-1-methoxy-5,6,7,8-tetrahydro-5,8-methanoisoquinoline prepared in Preparation example 16, necessary components were fractionated by a fraction collector (column: CHIRALPAK AD-H, size: 10 cm I. D.×25 cm L, mobile phase: 100% methanol, flow rate: 142 mL/min, measurement wavelength: 280 nm, temperature: 25° C.), based on the detection chromatogram of a UV detector. The fractions were concentrated under reduced pressure and dried in vacuum respectively, thereby obtaining a first peak (Preparation example 58-1) and a second peak (Preparation example 58-2) respectively as a single enantiomer.

Example 1

Morpholine (23 mg), N-[(dimethylamino)(3H-[1,2,3]triazolo[4,5-b]pyridin-3-yloxy)methylene]-N-methylmethanaminium hexafluorophosphate (136 mg), and N-ethyl-N-isopropylpropan-2-amine (51 mg) were added to a mixture of 1-[(3-chlorophenyl)amino]-5,6,7,8-tetrahydroisoquinoline-4-carboxylic acid (54 mg) and N,N-dimethylformamide (2 mL) followed by stirring for 15 hours at 30° C. Thereafter, water was added thereto followed by extraction with ethyl acetate. The organic layer was washed with water and saturated brine and dried over anhydrous magnesium sulfate, followed by filtration. The obtained filtrate was concentrated, and the residue was purified by silica gel column chromatography (hexane-ethyl acetate). The obtained solids were dissolved in chloroform, and diisopropylether was added thereto under stirring. The resulting solids were collected by filtration, washed with diisopropylether, and dried, thereby obtaining N-(3-chlorophenyl)-4-(morpholin-4-ylcarbonyl)-5,6,7,8-tetrahydroisoquinoline-1-amine (45.3 mg) as white powder.

Example 2

2,2'-Bis(diphenylphosphino)-1,1'-binaphthyl (9 mg), sodium tert-butoxide (35 mg), and tris(dibenzylideneacetone)dipalladium (3 mg) were added to a mixture of 4-bromo-1-(morpholin-4-ylsulfonyl)-5,6,7,8-tetrahydroisoquinoline (65 mg), 3-chloroaniline (23 µL), and toluene (3 mL) followed by stirring for 16 hours at 100° C. in an argon atmosphere. Saturated brine was added to the reaction solution, the insoluble material was separated by filtration, and then the filtrate was extracted with ethyl acetate. The organic layer was dried over anhydrous sodium sulfate, followed by filtration. The obtained filtrate was concentrated, and the residue was purified by silica gel column chromatography (hexane-ethyl acetate) and then washed with diisopropylether, thereby obtaining N-(3-chlorophenyl)-1-(morpholin-4-ylsulfonyl)-5,6,7,8-tetrahydroisoquinoline-4-amine (23 mg) as white solids.

Example 3

3-Chloroperbenzoic acid (102 mg) was added to a mixture of {4-[(3-chlorophenyl)sulfanyl]-5,6,7,8-tetrahydroisoquinolin-1-yl}(4,4-difluoropiperidin-1-yl)methanone (84 mg) and dichloromethane (3 mL) under ice cooling followed by stirring for 4 hours. A saturated aqueous sodium hydrogen carbonate solution was added to the reaction solution followed by extraction with chloroform. The organic layer was washed with saturated brine and dried over anhydrous sodium sulfate, followed by filtration. The obtained filtrate was concentrated, and the residue was purified by silica gel column chromatography (hexane-ethyl acetate) and then recrystallized from ethyl acetate-diisopropylether, thereby obtaining {4-[(3-chlorophenyl)sulfonyl]-5,6,7,8-tetrahydroisoquinolin-1-yl}(4,4-difluoropiperidin-1-yl)methanone (69 mg) as white solids.

Example 4

Morpholine (19 mg), N-[(dimethylamino)(3H-[1,2,3]triazolo[4,5-b]pyridin-3-yloxy)methylene]-N-methylmethanaminium hexafluorophosphate (113 mg), and N-ethyl-N-isopropylpropan-2-amine (48 mg) were added to a mixture of 1-(cyclooctylamino)-5,6,7,8-tetrahydroisoquinoline-4-carboxylic acid (45 mg) and N,N-dimethylformamide (1 mL) followed by stirring for 15 hours at room temperature. Thereafter, water was added thereto followed by extraction with ethyl acetate. The organic layer was washed with water and saturated brine and dried over anhydrous magnesium sulfate, followed by filtration. The obtained filtrate was concentrated, and the residue was purified by silica gel column chromatography (hexane-ethyl acetate). The obtained solids were dissolved in ethanol (2 mL), and a 4 M hydrogen chloride/dioxane solution (1 mL) was added thereto followed by heating for 30 minutes at 70° C. Thereafter, the solvent was evaporated under reduced pressure. The residue was dissolved in a mixed solution including ethyl acetate and methanol, and diisopropylether was added thereto under stirring. The resulting solids were collected by filtration, washed with diisopropylether, and dried, thereby obtaining [1-(cyclooctylamino)-5,6,7,8-tetrahydroisoquinolin-4-yl](morpholin-4-yl)methanone monohydrochloride (31 mg) as white powder.

Example 5

{4-[(3-Chloro-4-fluorophenyl)amino]-5,6,7,8-tetrahydro-5,8-methanoisoquinolin-1-yl}(1,1-dioxidothiomorpholin-4-yl)methanone (120 mg) as a racemic mixture was separated by CHIRALPAK AD-H (0.46 cmφ×25 cm L, hexane-ethanol-diethylamine), thereby obtaining a low-polarity enantiomer and a high-polarity enantiomer. The obtained two components were respectively dissolved in methanol (1 mL), a 4 M hydrogen chloride/ethyl acetate solution (0.1 mL) was added thereto, and then the solvent was evaporated under reduced pressure. The residue was stirred in ethyl acetate-ethanol, and the resulting solids were collected by filtration, thereby respectively obtaining a low-polarity enantiomer (54 mg, Example No. 5-1) and a high-polarity enantiomer (53 mg, Example No. 5-2) of {4-[(3-chloro-4-fluorophenyl)amino]-5,6,7,8-tetrahydro-5,8-methaisoquinolin-1-yl}(1,1-dioxidothiomorpholin-4-yl)methanone monohydrochloride, as white solids.

Example 6

N,N-diisopropylethylamine (71 mg) was added to a mixture of 4-[(3-chlorophenyl)amino]-5,6,7,8-tetrahydro-5,8-ethanophthalazine-1-carboxylic acid (120 mg), morpholine (38 mg), 2-(1H-7-azabenzotriazol-1-yl)-1,1,3,3-tetramethyluronium hexafluorophosphate Methanaminium (166 mg), and N,N-dimethylimidazolidinone (5 mL) at room temperature followed by stirring for 16 hours at 100° C. in a nitrogen atmosphere and cooling to room temperature. Thereafter, ethyl acetate and water were added thereto to perform liquid separation. The organic layer was washed with water and saturated brine and then dried over anhydrous magnesium sulfate, followed by filtration, and then the solvent was evaporated under reduced pressure. The residue was purified by silica gel column chromatography (hexane-ethyl acetate), thereby obtaining {4-[(3-chlorophenyl)amino]-5,6,7,8-tetrahydro-5,8-ethanophthalazin-1-yl}(morpholin-4-yl)methanone (15 mg) as pale brown powder.

Example 7

N-[(dimethylamino)(3H-[1,2,3]triazolo[4,5-b]pyridin-3-yloxy)methylene]-N-methylmethanaminium hexafluorophosphate (397 mg) was added to a mixture of 4-[(3,4-difluorophenyl)amino]-5,6,7,8-tetrahydro-5,8-methanoisoquinoline-1-carboxylic acid (300 mg), thiomorpholine dioxide (167 mg), diisopropylethylamine (405 µL), and N,N-dimethylformamide (12 mL) under ice cooling followed by stirring for 15 hours at room temperature. Water was added to the reaction solution, and extraction was performed with ethyl acetate. The organic layer was washed with water and saturated brine and dried over anhydrous magnesium sulfate, followed by filtration. The obtained filtrate was concentrated, and the residue was purified by silica gel column chromatography (eluent: hexane-ethyl acetate). The obtained racemic mixture was separated by CHIRALPAK AD-H (0.46 cmφ×25 cm L, hexane-ethanol-diethylamine), thereby obtaining a low-polarity enantiomer and a high-polarity enantiomer. The obtained two components were respectively dissolved in methanol (1 mL), a 4 M hydrogen chloride/ethyl acetate solution (0.1 mL) was added thereto, and then the solvent was evaporated under reduced pressure. The residue was stirred in ethyl acetate-ethanol, and the resulting solids were collected by filtration, thereby respectively obtaining a low-polarity enantiomer (107 mg, Example No. 7-1) and a high-polarity enantiomer (156 mg, Example No. 7-2) of {4-[(3,4-difluorophenyl)amino]-5,6,7,8-tetrahydro-5,8-methanoisoquinolin-1-yl}(1,1-dioxidothiomorpholin-4-yl)methanone monohydrochloride, as white solids.

Example 8

An aqueous sodium hydroxide solution (15 wt %, 3 mL) was added to a mixture of ethyl 1-[(3-acetoxyadamantan-1-yl)amino]-5,6,7,8-tetrahydroisoquinoline-4-carboxylate (250 mg), ethanol (3 mL), and tetrahydrofuran (2 mL), and the resultant was stirred for 24 hours at room temperature and for 24 hours at 40° C. The reaction solution was concentrated under reduced pressure, water was added to the residue, and the residue was washed with ether. 1 M hydrochloric acid was added to the aqueous layer until the pH became 1 followed by extraction with ethyl acetate. The organic layer was washed with saturated brine and dried over anhydrous sodium sulfate, followed by filtration. The obtained filtrate was concentrated. N,N-dimethylformamide (4.3 mL), thiomorpholine dioxide (127 mg), 1H-benzotriazol-1-ol (101 mg), and N-[3-(dimethylamino)propyl]-N'-ethylcarbodiimide hydrochloride (144 mg) were added to the obtained yellow solids, and the resultant was stirred for 16 hours at room temperature. Water was added to the reaction solution, and extraction was performed with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate). The obtained solids were dissolved in ethyl acetate (2 mL), and a 4 M hydrogen chloride/dioxane solution (0.2 mL) was added thereto. The resultant was stirred for an hour at room temperature, and then the solvent was evaporated under reduced pressure. The residue was suspended in a mixed solution including ethyl acetate and hexane, solids were collected by filtration and dried, thereby obtaining (1,1-dioxidothiomorpholin-4-yl){1-[(3-hydroxyadamantan-1-yl)amino]-5,6,7,8-tetrahydroisoquinolin-4-yl}methanone monohydrochloride (66 mg) as pale yellow powder.

Example 9

Methanesulfonyl chloride (22 μL) was added to a mixture of {4-[(3,5-difluoroadamantan-1-yl)amino]-5,6,7,8-tetrahydroisoquinolin-1-yl}methanol (67 mg), triethylamine (80 μL), and ethyl acetate (3 mL) under ice cooling followed by stirring for an hour. A saturated aqueous sodium hydrogen carbonate solution was added to the reaction mixture followed by extraction with ethyl acetate. The organic layer was washed with saturated brine and dried over anhydrous sodium sulfate, followed by filtration. The residue was dissolved in N,N-dimethylformamide (3 mL), potassium carbonate (80 mg) and thiomorpholine dioxide (52 mg) were added thereto at room temperature followed by stirring overnight. Water was added to the reaction mixture followed by extraction with ethyl acetate. The organic layer was washed with saturated brine and dried over anhydrous sodium sulfate, followed by filtration. The obtained filtrate was concentrated, and the residue was purified by silica gel column chromatography (hexane-ethyl acetate), thereby obtaining N-(3,5-difluoroadamantan-1-yl)-1-[(1,1-dioxidothiomorpholin-4-yl)methyl]-5,6,7,8-tetrahydroisoquinolin-4-amine (3.5 mg) as white solids.

The compounds shown in the following tables were prepared in the same manner as in preparation examples and examples described above.

In addition, the compounds of the present invention that are obtained by the method described in the above examples or by the similar method can also be obtained as crystals as desired, through a crystallization step known to a person skilled in the related art. For example, the compound of Ex. 120-2 described in the following Table 70 was obtained as white crystals (63 mg) by a method in which the white solids (75 mg) obtained by the same method as in Example 4 were suspended in a mixture (2 mL) including acetone and water (20:1), and the resultant was stirred for 48 hours at room temperature, collected by filtration, washed with acetone, and then dried for 12 hours at room temperature under reduced pressure.

The compounds of Example Nos. 10, 16, 30, 36, 52, 98, 101, 112, 117-2, 119-2, 125, 127, 133-2, 138, 164, 165, 167, and 179 shown in the following tables were obtained as crystals through the same crystallization step as described above. For these crystals, an extrapolation starting temperature was measured by the following measurement method by using Differential Scanning calorimetry (DSC).

Differential Scanning Calorimetry (DSC)

The crystals (3 mg) were filled into a dedicated sample pan made of aluminum, the change in calories caused between the sample and a reference (empty sample pan made of aluminum) was consecutively measured in a nitrogen atmosphere (50 mL/min) at a temperature rise rate of 10° C./min, within a measurement range of room temperature to 300° C., and the results were recorded. In addition, handling of the instrument including data processing was based on the method and the order instructed in the respective instruments (instruments: Hi-Res DSC 2910 and DSC Q20 manufactured by TA Instruments).

The chemical structural formula, preparation method, and physicochemical data of the compounds of preparation examples are shown in the following Tables 3 to 61. In addition, the following Tables 62 to 89 show the chemical structural formula of the compounds of examples, and Tables 90 to 108 show the preparation methods and physicochemical data of the compounds of examples.

TABLE 3

| PEx | PSyn | Str | Data |
|-----|------|-----|------|
| 1 | 1 | [structure] | ESI+Na: 211 |
| 2 | 2 | [structure] | ESI+ Na: 197 |
| 3 | 3 | [structure] | NMR1: 1.72-1.85 (4 H, m), 2.71(2 H, t, J = 5.8 Hz), 2.89(2 H, t, J = 5.8 Hz), 8.66(1 H, s) |
| 4 | 4 | [structure] | ESI+: 284 |
| 5 | 5 | [structure] | ESI−: 301 |

TABLE 3-continued

| PEx | PSyn | Str | Data |
|---|---|---|---|
| 6 | 6 | (ethyl 1-oxo-1,2,5,6,7,8-hexahydroisoquinoline-4-carboxylate) | ESI+: 222 |
| 7 | 7 | (ethyl 1-chloro-5,6,7,8-tetrahydroisoquinoline-4-carboxylate) | ESI+: 240 |

TABLE 4

| PEx | PSyn | Str | Data |
|---|---|---|---|
| 8 | 8 | (ethyl 1-(3-(trifluoromethyl)phenoxy)-5,6,7,8-tetrahydroisoquinoline-4-carboxylate) | ESI+: 366 |
| 9 | 9 | (3-amino-1-hydroxy-6,7-dihydro-5H-cyclopenta[c]pyridine-4-carboxamide) | ESI+: 194 |
| 10 | 10 | (3-amino-4-cyano-1-hydroxy-6,7-dihydro-5H-cyclopenta[c]pyridine) | ESI+: 194/196 |
| 11 | 11 | (1-chloro-6,7-dihydro-5H-cyclopenta[c]pyridine-4-carbonitrile) | ESI+: 179/181 |
| 12 | 12 | (1-((3-chlorophenyl)amino)-6,7-dihydro-5H-cyclopenta[c]pyridine-4-carbonitrile) | ESI+: 270/272 |

TABLE 4-continued

| PEx | PSyn | Str | Data |
|---|---|---|---|
| 13 | 13 | (1-((3-chlorophenyl)amino)-6,7-dihydro-5H-cyclopenta[c]pyridine-4-carboxylic acid) | ESI+: 289/291 |
| 14 | 14 | (1-(methylsulfinyl) bridged bicyclic pyridine) | ESI+: 208 |

TABLE 5

| PEx | PSyn | Str | Data |
|---|---|---|---|
| 15 | 15 | (1-methoxy bridged bicyclic isoquinoline) | ESI+: 176 |
| 16 | 16 | (4-bromo-1-methoxy bridged bicyclic isoquinoline) | ESI+: 254/256 |
| 17 | 17 | (ethyl 1-methoxy bridged bicyclic isoquinoline-4-carboxylate) | ESI+: 248 |
| 18 | 18 | (ethyl 1-oxo bridged bicyclic isoquinoline-4-carboxylate) | ESI+: 234 |
| 19 | 19 | (ethyl 1-chloro bridged bicyclic isoquinoline-4-carboxylate) | ESI+: 252 |
| 20 | 20 | (ethyl 1-((3-(trifluoromethyl)phenyl)amino) bridged bicyclic isoquinoline-4-carboxylate) | ESI+: 377 |

TABLE 5-continued

| PEx | PSyn | Str | Data |
|---|---|---|---|
| 21 | 21 | | ESI+: 327 |

TABLE 6

| PEx | PSyn | Str | Data |
|---|---|---|---|
| 22 | 22 | | ESI+: 349 |
| 23 | 23 | | ESI+: 206 |
| 24 | 24 | | ESI+: 222 |
| 25 | 25 | | ESI+: 289 |
| 26 | 26 | | ESI+: 275 |
| 27 | 27 | | ESI+: 293 |

TABLE 6-continued

| PEx | PSyn | Str | Data |
|---|---|---|---|
| 28 | 28 | | ESI+: 284 |

TABLE 7

| PEx | PSyn | Str | Data |
|---|---|---|---|
| 29 | 29 | | ESI+: 303 |
| 30 | 30 | | ESI+: 324 |
| 31 | 31 | | ESI+: 306 |
| 32 | 32 | | ESI+: 244 |
| 33 | 33 | | ESI+: 361 |
| 34 | 34 | | ESI+: 351 |
| 35 | 35 | | ESI+: 337 |

TABLE 8
| PEx | PSyn | Str | Data |
|---|---|---|---|
| 36 | 36 | 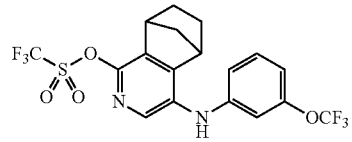 [SMILES: O=S(=O)(Oc1ncc(Nc2cccc(OC(F)(F)F)c2)c2c1C1CCC2C1)C(F)(F)F] | ESI+: 469 |
| 37 | 37 | 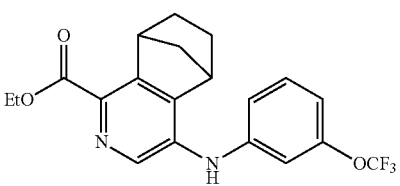 [SMILES: O=C(O)c1ncc(Nc2cccc(OC(F)(F)F)c2)c2c1C1CCC2C1] | ESI+: 393 |
| 38 | 38 | 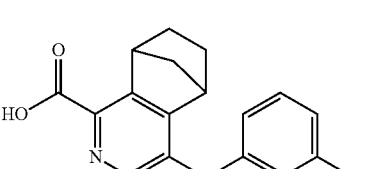 | ESI+: 365 |
| 39-1 | 39 | 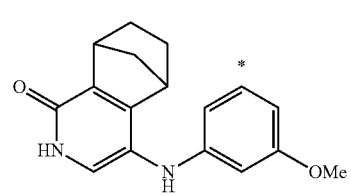 [SMILES: COc1cccc(Nc2c[nH]c(=O)c3c2C2CCC3C2)c1] | ESI+: 283 |
| 39-2 | 39 | 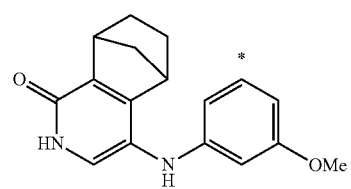 [SMILES: COc1cccc(Nc2c[nH]c(=O)c3c2C2CCC3C2)c1] | ESI+: 283 |
| 40 | 40 | 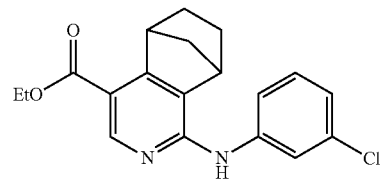 | ESI+: 343 |
| 41 | 41 | 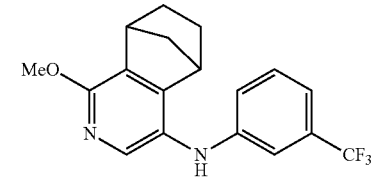 [SMILES: COc1ncc(Nc2cccc(C(F)(F)F)c2)c2c1C1CCC2C1] | ESI+: 335 |
TABLE 9
| PEx | PSyn | Str | Data |
|---|---|---|---|
| 42 | 42 | 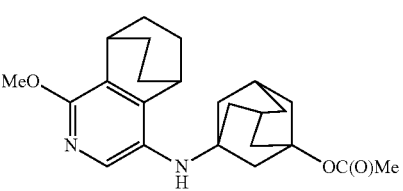 | ESI+: 397 |
| 43 | 43 | 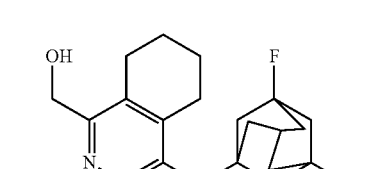 | ESI+: 349 |
| 44 | 44 | 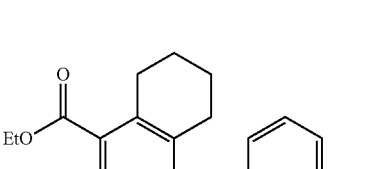 | ESI+: 381 |
| 45 | 45 | 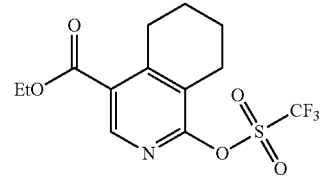 [SMILES: CCOC(=O)c1cnc(OS(=O)(=O)C(F)(F)F)c2c1CCCC2] | ESI+: 354 |
| 46 | 46 | 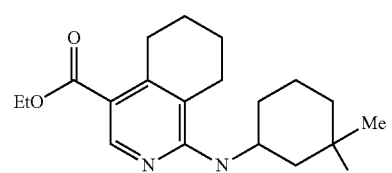 | ESI+: 331 |
| 47 | 47 | 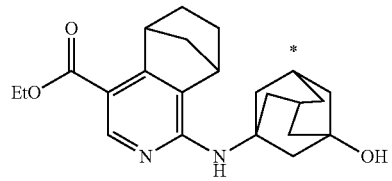 [SMILES: CCOC(=O)c1cnc(NC23CC4CC(CC(O)(C4)C2)C3)c2c1C1CCC2C1] | ESI+: 383 |
| 48 | 48 | 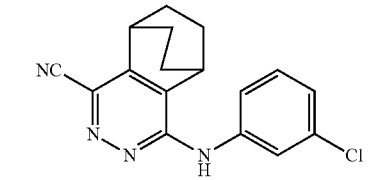 [SMILES: N#Cc1nnc(Nc2cccc(Cl)c2)c2c1C1CCC2CC1] | ESI+: 311 |

TABLE 10

| PEx | PSyn | Str | Data |
|---|---|---|---|
| 49 | 49 | | ESI+: 329 |
| 50 | 50 | | ESI+: 220 |
| 51 | 51 | | ESI+: 358 |
| 52 | 52 | | ESI+: 344 |
| 53 | 53 | | ESI+: 362 |
| 54 | 54 | | ESI+: 453 |

TABLE 11

| PEx | PSyn | Str | Data |
|---|---|---|---|
| 55-1 | 55 | (structure) | ESI+: 315 |
| 55-2 | 22 | (structure) | ESI+: 315 |
| 56 | 56 | (structure) | ESI+: 320 |
| 57 | 57 | (structure) | ESI+: 220 |
| 58-1 | 58 | (structure) | ESI+: 254/256 [a]D: −25.8 (c = 1.415, EtOH) |
| 58-2 | 58 | (structure) | ESI+: 254/256 [a]D: +26.1 (c = 1.265, EtOH) |
| 59-1 | 37 | (structure) | ESI+: 327 |

TABLE 12

| PEx | PSyn | Str | Data |
|---|---|---|---|
| 59-2 | 37 | (structure) | ESI+: 327 |
| 60-1 | 37 | (structure) | ESI+: 339 |
| 60-2 | 37 | (structure) | ESI+: 339 |
| 61-1 | 37 | (structure) | ESI+: 425 |
| 61-2 | 37 | (structure) | ESI+: 425 |
| 62-1 | 40 | (structure) | ESI+: 393 |

TABLE 13

| PEx | PSyn | Str | Data |
|---|---|---|---|
| 62-2 | 20 | ethyl ester of pyridine fused bicyclic amine with 3-(trifluoromethoxy)phenyl NH | NMR2: 1.15-1.27 (2 H, m), 1.40 (3 H, t, J = 7.0 Hz), 1.57(1 H, d, J = 9.0 Hz), 1.77(1 H, d, J = 9.0 Hz), 1.92-2.07 (2 H, m), 3.35(1 H, s), 4.23(1 H, s), 4.37 (2 H, q, J = 7.0 Hz), 6.46(1 H, s), 6.87 (1 H, d, J = 7.4 Hz), 7.31(1 H, dd, J = 7.4, 8.2 Hz), 7.46(1 H, d, J = 8.2 Hz), 7.71 (1 H, s), 8.72(1 H, s) |
| 63-1 | 40 | ethyl ester with 3-chloro-4-fluorophenyl NH | ESI+: 361 |
| 63-2 | 20 | ethyl ester with 3-chloro-4-fluorophenyl NH | NMR2: 1.15-1.25 (2 H, m), 1.40 (3 H, t, J = 7.1 Hz), 1.56(1 H, d, J = 9.1 Hz), 1.75(1 H, d, J = 9.1 Hz), 1.91-2.07 (2 H, m), 3.31 (1 H, s), 4.22(1 H, s), 4.36(2 H, q, J = 7.1 Hz), 6.32(1 H, s), 7.09(1 H, m), 7.39 (1 H, m), 7.81(1 H, dd, J = 2.6, 6.5 Hz), 8.68(1 H, s) |
| 64-1 | 40 | ethyl ester with 3,4-difluorophenyl NH | ESI+: 345 |

TABLE 14

| PEx | PSyn | Str | Data | PEx | PSyn | Str | Data |
|---|---|---|---|---|---|---|---|
| 64-2 | 20 | ethyl ester with 3,4-difluorophenyl NH | ESI+: 345 | 65-2 | 20 | ethyl ester with 4-fluoro-3-CF3-phenyl NH | ESI+: 395 |
| 65-1 | 40 | ethyl ester with 4-fluoro-3-CF3-phenyl NH | ESI+: 395 | 66-1 | 40 | ethyl ester with 3-methylphenyl NH | ESI+: 323 |

TABLE 14-continued

| PEx | PSyn | Str | Data |
|---|---|---|---|
| 66-2 | 20 | | ESI+: 323 |
| 67-1 | 40 | | ESI+: 339 |
| 67-2 | 20 | | ESI+: 339 |

TABLE 15

| PEx | PSyn | Str | Data |
|---|---|---|---|
| 68-1 | 41 | | ESI+: 285 |
| 68-2 | 41 | | ESI+: 285 |
| 69-1 | 41 | | ESI+: 297 |
| 69-2 | 41 | | ESI+: 297 |

TABLE 15-continued

| PEx | PSyn | Str | Data |
|---|---|---|---|
| 70-1 | 42 | | ESI+: 383 |
| 70-2 | 42 | | ESI+: 383 |
| 71-1 | 42 | | ESI+: 403 |

TABLE 16

| PEx | PSyn | Str | Data |
|---|---|---|---|
| 71-2 | 36 | | ESI+: 403 |
| 72-1 | 36 | | ESI+: 415 |
| 72-2 | 36 | | ESI+: 415 |
| 73-1 | 36 | | ESI+: 501 |
| 73-2 | 36 | | ESI+: 501 |

TABLE 16-continued

| PEx | PSyn | Str | Data |
|---|---|---|---|
| 74-1 | 22 | (carboxylic acid, bicyclic isoquinoline core, NH-phenyl-3-OCF₃) | ESI+: 365 |
| 74-2 | 22 | (carboxylic acid, bicyclic isoquinoline core, NH-phenyl-3-OCF₃) | ESI+: 365 |

TABLE 17

| PEx | PSyn | Str | Data |
|---|---|---|---|
| 75-1 | 22 | (carboxylic acid, bicyclic isoquinoline core, NH-phenyl-4-F-3-Cl) | ESI+: 333 |
| 75-2 | 22 | (carboxylic acid, bicyclic isoquinoline core, NH-phenyl-4-F-3-Cl) | ESI+: 333 |
| 76-1 | 22 | (carboxylic acid, bicyclic isoquinoline core, NH-phenyl-4-F-3-CF₃) | ESI+: 367 |
| 76-2 | 22 | (carboxylic acid, bicyclic isoquinoline core, NH-phenyl-4-F-3-CF₃) | ESI+: 367 |
| 77-1 | 22 | (carboxylic acid, bicyclic isoquinoline core, NH-phenyl-3,4-diF) | ESI+: 317 |

TABLE 17-continued

| PEx | PSyn | Str | Data |
|---|---|---|---|
| 77-2 | 22 | (carboxylic acid, bicyclic isoquinoline core, NH-phenyl-3,4-diF) | ESI+: 317 |
| 78-1 | 22 | (carboxylic acid, bicyclic isoquinoline core, NH-phenyl-3-Me) | ESI+: 295 |

TABLE 18

| PEx | PSyn | Str | Data |
|---|---|---|---|
| 78-2 | 22 | (carboxylic acid, bicyclic isoquinoline core, NH-phenyl-3-Me) | ESI+: 295 |
| 79-1 | 22 | (carboxylic acid, bicyclic isoquinoline core, NH-phenyl-3-OMe) | NMR1: 1.21-1.42 (3H, m), 1.70-1.90 (3H, m), 3.64(1 H, s), 3.78(3 H, s), 4.29(1 H, s), 6.57(1 H, d, J = 8.1 Hz), 7.20(1 H, dd, J = 8.1, 8.1 Hz), 7.37(1 H, d, J = 8.1 Hz), 7.44(1 H,s), 8.57(1 H,s), 8.59(1 H,s), 12.58(1 H, brs). |
| 79-2 | 22 | (carboxylic acid, bicyclic isoquinoline core, NH-phenyl-3-OMe) | ESI+: 311 |
| 80-1 | 38 | (carboxylic acid, bicyclic isoquinoline core, NH-phenyl-3-F) | ESI+: 299 |
| 80-2 | 38 | (carboxylic acid, bicyclic isoquinoline core, NH-phenyl-3-F) | ESI+: 299 |

TABLE 18-continued

| PEx | PSyn | Str | Data |
|---|---|---|---|
| 81-1 | 38 | | ESI+: 311 |

TABLE 19

| PEx | PSyn | Str | Data |
|---|---|---|---|
| 81-2 | 38 | | ESI+: 311 |
| 82-1 | 38 | | ESI+: 355 |
| 82-2 | 38 | | ESI+: 355 |
| 83-1 | 35 | | ESI+: 271 |
| 83-2 | 35 | | ESI+: 271 |
| 84-1 | 35 | | ESI+: 369 |

TABLE 19-continued

| PEx | PSyn | Str | Data |
|---|---|---|---|
| 84-2 | 35 | | ESI+: 369 |

TABLE 20

| PEx | PSyn | Str | Data |
|---|---|---|---|
| 85 | 37 | | ESI+: 391 |
| 86 | 37 | | ESI+: 315 |
| 87 | 37 | | ESI+: 332 |
| 88 | 37 | | ESI+: 366 |
| 89 | 37 | | ESI+: 348 |
| 90 | 37 | | ESI+: 365 |

TABLE 20-continued
| PEx | PSyn | Str | Data |
|---|---|---|---|
| 91 | 37 | | ESI+: 381 |
TABLE 21
| PEx | PSyn | Str | Data |
|---|---|---|---|
| 92 | 37 | | ESI+: 343 |
| 93 | 37 | | ESI+: 361/363 |
| 94 | 37 | | ESI+: 395 |
| 95 | 37 | | ESI+: 377 |
| 96 | 37 | | ESI+: 403 |
| 97 | 37 | | ESI+: 387 |
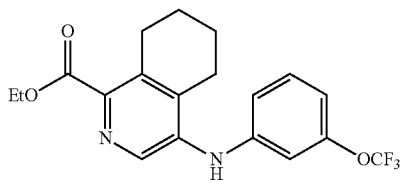
TABLE 21-continued
| PEx | PSyn | Str | Data |
|---|---|---|---|
| 98 | 37 | | ESI+: 323 |
TABLE 22
| PEx | PSyn | Str | Data |
|---|---|---|---|
| 99 | 37 | | ESI+: 357 |
| 100 | 37 | | ESI+: 334 |
| 101 | 37 | | ESI+: 391 |
| 102 | 37 | | ESI+: 407 |
| 103 | 37 | | ESI+: 359 |
| 104 | 37 | | ESI+: 341 |
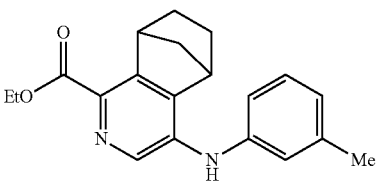 [SMILES: CCOC(=O)c1ncc(Nc2cccc(C)c2)c2c1C1CCC2C1]

TABLE 22-continued

| PEx | PSyn | Str | Data |
|---|---|---|---|
| 105 | 37 | (ethyl ester isoquinoline-adamantane-NH-3-methylphenyl) | ESI+: 337 |

TABLE 23

| PEx | PSyn | Str | Data |
|---|---|---|---|
| 106 | 37 | (ethyl ester isoquinoline-adamantane-NH-3,5-difluoroadamantyl) | ESI+: 417 |
| 107 | 37 | (ethyl ester isoquinoline-adamantane-NH-4-fluoro-3-CF3-phenyl) | ESI+: 409 |
| 108 | 37 | (ethyl ester isoquinoline-adamantane-NH-3-OMe-phenyl) | ESI+: 353 |
| 109 | 37 | (ethyl ester isoquinoline-adamantane-NH-3,4-difluorophenyl) | ESI+: 345 |
| 110 | 37 | (ethyl ester isoquinoline-adamantane-NH-2,4-difluorophenyl) | ESI+: 345 |
| 111 | 37 | (ethyl ester isoquinoline-adamantane-NH-adamantyl-OC(O)Me) | ESI+: 439 |

TABLE 23-continued

| PEx | PSyn | Str | Data |
|---|---|---|---|
| 112 | 25 | (ethyl ester tetrahydroisoquinoline-NH-3,5-difluoroadamantyl) | ESI+: 391 |

TABLE 24

| PEx | PSyn | Str | Data |
|---|---|---|---|
| 113 | 25 | (ethyl ester tetrahydroisoquinoline-NH-norbornyl) | ESI+: 315 |
| 114 | 25 | (MeO-tetrahydroisoquinoline-NH-5-chloropyridin-3-yl) | ESI+: 290 |
| 115 | 25 | (MeO-tetrahydroisoquinoline-NH-3-CF3-phenyl) | ESI+: 323 |
| 116 | 25 | (MeO-tetrahydroisoquinoline-NH-3-OCF3-phenyl) | ESI+: 339 |
| 117 | 34 | (MeO-bicyclic-NH-3-chlorophenyl) | ESI+: 301 |
| 118 | 34 | (MeO-bicyclic-NH-4-fluoro-3-chlorophenyl) | ESI+: 319/321 |

TABLE 24-continued
| PEx | PSyn | Str | Data |
|---|---|---|---|
| 119 | 34 | | ESI+: 361 |
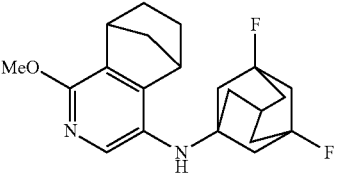 [SMILES: COc1ncc(NC23CC4CC(F)(CC(F)(C4)C2)C3)c2c1C1CCC2C1]
TABLE 25
| PEx | PSyn | Str | Data |
|---|---|---|---|
| 120 | 40 | | ESI+: 341 |
| 121 | 40 | | ESI+: 391 |
| 122 | 40 | | ESI+: 337 |
| 123 | 41 | | ESI+: 353 |
| 124 | 41 | | ESI+: 292 |
| 125 | 41 | | ESI+: 345 |
TABLE 25-continued
| PEx | PSyn | Str | Data |
|---|---|---|---|
| 126 | 41 | | ESI+: 281 |
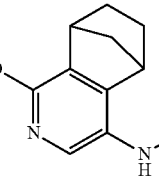
TABLE 26
| PEx | PSyn | Str | Data |
|---|---|---|---|
| 127 | 41 | | ESI+: 315 |
| 128 | 41 | | ESI+: 333/335 |
| 129 | 41 | | ESI+: 349 |
| 130 | 41 | | ESI+: 317 |
| 131 | 41 | | ESI+: 299 |
| 132 | 41 | | ESI+: 295 |

TABLE 26-continued

| PEx | PSyn | Str | Data |
|---|---|---|---|
| 133 | 41 | (structure) | ESI+: 365 |

TABLE 27

| PEx | PSyn | Str | Data |
|---|---|---|---|
| 134 | 41 | (structure) | ESI+: 375 |
| 135 | 41 | (structure) | ESI+: 367 |
| 136 | 41 | (structure) | ESI+: 303 |
| 137 | 41 | (structure) | ESI+: 303 |
| 138 | 42 | (structure) | ESI+: 273 |
| 139 | 41 | (structure) | ESI+: 311 |

TABLE 27-continued

| PEx | PSyn | Str | Data |
|---|---|---|---|
| 140 | 42 | (structure) | ESI+: 349 |

TABLE 28

| PEx | PSyn | Str | Data |
|---|---|---|---|
| 141 | 34 | (structure) | ESI+: 329 |
| 142 | 34 | (structure) | ESI+: 331 |
| 143 | 8 | (structure) | ESI+: 378 |
| 144 | 12 | (structure) | ESI+: 254 |
| 145 | 12 | (structure) | ESI+: 288/290 |
| 146 | 20 | (structure) | ESI+: 393 |

TABLE 28-continued
| PEx | PSyn | Str | Data |
|---|---|---|---|
| 147 | 20 | 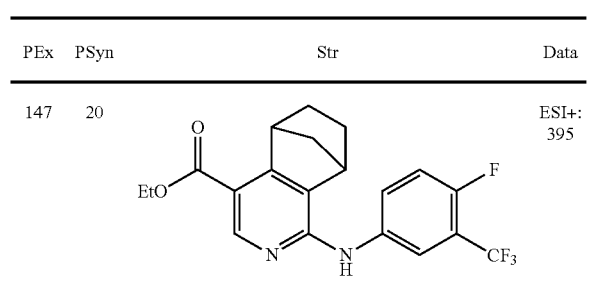 | ESI+: 395 |
TABLE 29
| PEx | PSyn | Str | Data |
|---|---|---|---|
| 148 | 20 | 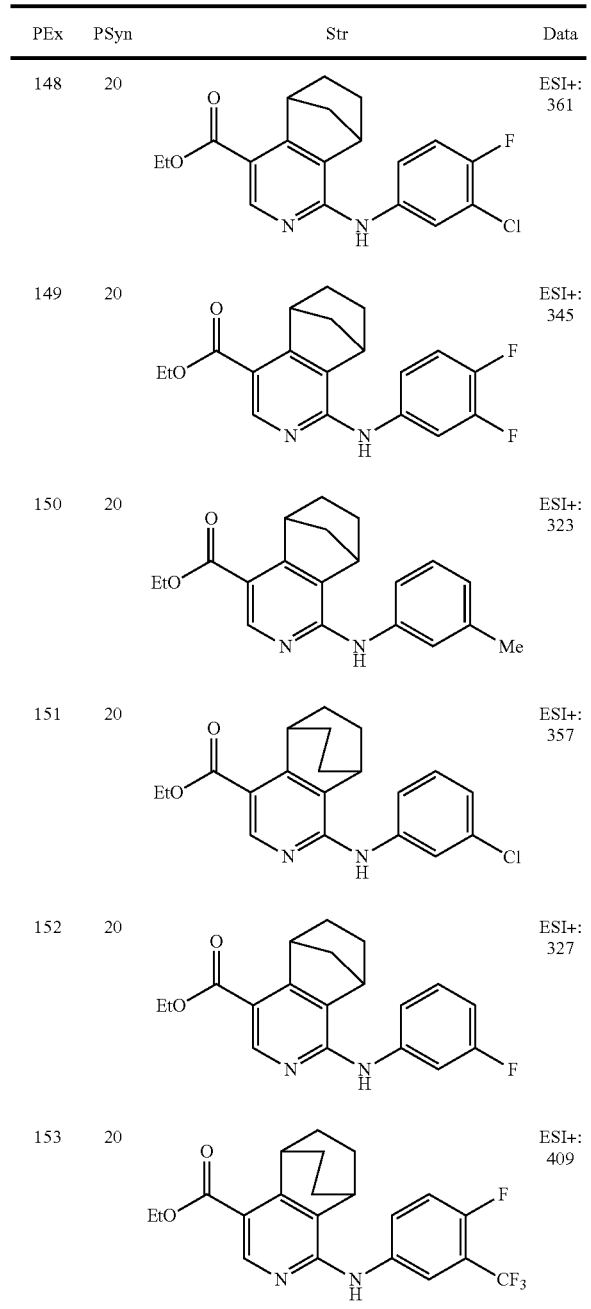 | ESI+: 361 |
| 149 | 20 | | ESI+: 345 |
| 150 | 20 | | ESI+: 323 |
| 151 | 20 | | ESI+: 357 |
| 152 | 20 | | ESI+: 327 |
| 153 | 20 | | ESI+: 409 |
TABLE 29-continued
| PEx | PSyn | Str | Data |
|---|---|---|---|
| 154 | 20 | 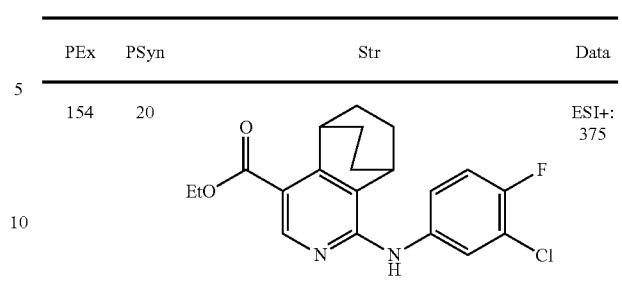 | ESI+: 375 |
TABLE 30
| PEx | PSyn | Str | Data |
|---|---|---|---|
| 155 | 20 | 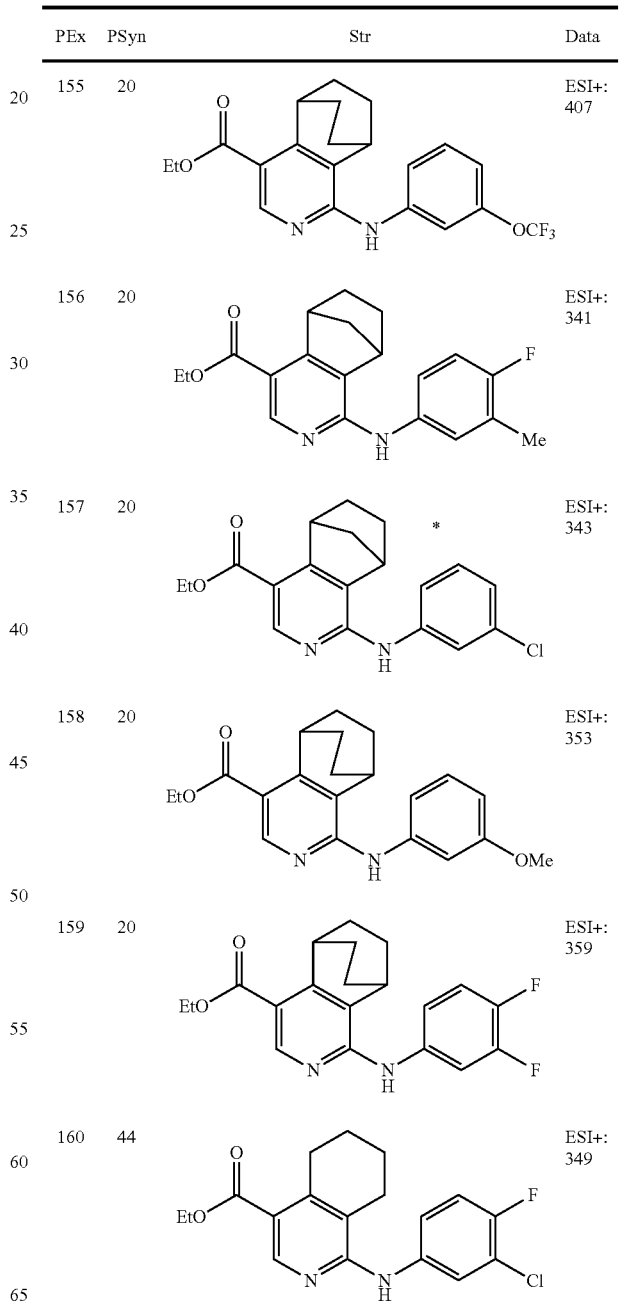 | ESI+: 407 |
| 156 | 20 | | ESI+: 341 |
| 157 | 20 | | ESI+: 343 |
| 158 | 20 | | ESI+: 353 |
| 159 | 20 | | ESI+: 359 |
| 160 | 44 | | ESI+: 349 |

TABLE 30-continued

| PEx | PSyn | Str | Data |
|---|---|---|---|
| 161 | 44 | | ESI+: 383 |

TABLE 31

| PEx | PSyn | Str | Data |
|---|---|---|---|
| 162 | 46 | | ESI+: 413 |
| 163 | 46 | | ESI+: 345 |
| 164 | 46 | | ESI+: 343 |
| 165 | 46 | | ESI+: 345 |
| 166 | 46 | | ESI+: 327 |
| 167 | 46 | | ESI+: 315 |

TABLE 31-continued

| PEx | PSyn | Str | Data |
|---|---|---|---|
| 168 | 46 | | ESI+: 383 |

TABLE 32

| PEx | PSyn | Str | Data |
|---|---|---|---|
| 169 | 46 | | ESI+: 397 |
| 170 | 46 | | ESI+: 417 |
| 171 | 46 | | ESI+: 403 |
| 172 | 10 | | ESI+: 212/214 |
| 173 | 19 | | ESI+: 266 |
| 174-1 | 19 | | No data |

TABLE 32-continued

| PEx | PSyn | Str | Data |
|---|---|---|---|
| 174-2 | 19 | (ethyl ester of chloro-substituted bicyclic isoquinoline carboxylate) | ESI+: 252 |
| 175 | 36 | (triflate of tetrahydroisoquinoline with 2,4-difluoroanilino group) | ESI+: 421 |

TABLE 33

| PEx | PSyn | Str | Data |
|---|---|---|---|
| 176 | 36 | (triflate of tetrahydroisoquinoline with difluoroadamantylamino group) | ESI+: 467 |
| 177 | 36 | (triflate of tetrahydroisoquinoline with norbornylamino group) | ESI+: 391 |

TABLE 33-continued

| PEx | PSyn | Str | Data |
|---|---|---|---|
| 178 | 36 | (triflate of tetrahydroisoquinoline with 5-chloropyridin-3-ylamino group) | ESI+: 408 |
| 179 | 36 | (triflate of tetrahydroisoquinoline with 3-(trifluoromethyl)phenoxy group) | ESI+: 442 |
| 180 | 36 | (triflate of tetrahydroisoquinoline with 3-chlorophenylthio group) | ESI+: 424 |
| 181 | 36 | (triflate of tetrahydroisoquinoline with 3-(trifluoromethoxy)anilino group) | ESI+: 457 |
| 182 | 36 | (triflate of tetrahydroisoquinoline with 3-(trifluoromethyl)anilino group) | ESI+: 441 |

TABLE 34

| PEx | PSyn | Str | Data |
|---|---|---|---|
| 183 | 36 | (triflate of bicyclic isoquinoline with 3-chloroanilino group) | ESI+: 419 |
| 184 | 36 | (triflate of bicyclic isoquinoline with 3-chloro-4-fluoroanilino group) | ESI+: 437/439 |

TABLE 34-continued

| PEx | PSyn | Str | Data |
|---|---|---|---|
| 185 | 36 | | ESI+: 471 |
| 186 | 36 | | ESI+: 453 |
| 187 | 36 | | ESI+: 479 |
| 188 | 36 | | ESI+: 463 |
| 189 | 36 | | ESI+: 399 |

TABLE 35

| PEx | PSyn | Str | Data |
|---|---|---|---|
| 190 | 36 | | ESI+: 433 |
| 191 | 36 | | ESI+: 451/453 |

TABLE 35-continued
| PEx | PSyn | Str | Data |
|---|---|---|---|
| 192 | 36 | 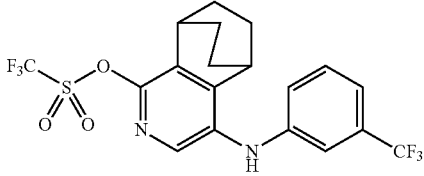 [SMILES: O=S(=O)(Oc1ncc(Nc2cccc(C(F)(F)F)c2)c2c1C1CCC2CC1)C(F)(F)F] | ESI+: 467 |
| 193 | 36 |  | ESI+: 435 |
| 194 | 36 | 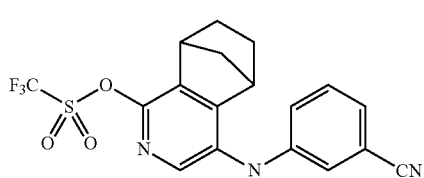 | ESI+: 410 |
| 195 | 36 | 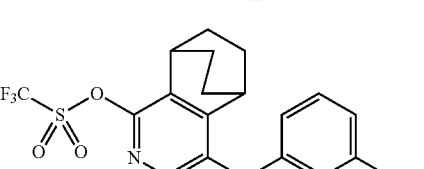 | ESI+: 483 |
| 196 | 36 | 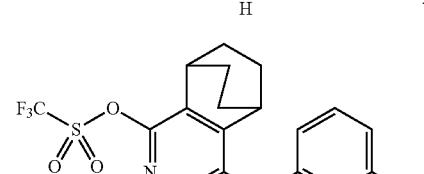 | ESI+: 417 |
TABLE 36
| PEx | PSyn | Str | Data |
|---|---|---|---|
| 197 | 36 | 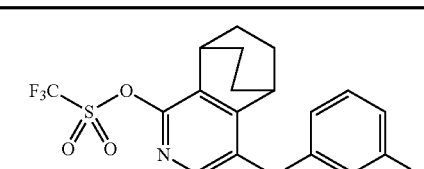 | ESI+: 413 |
| 198 | 36 | 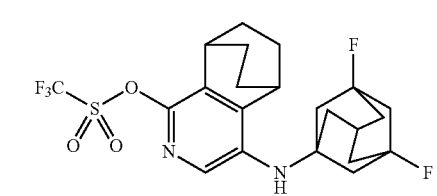 [SMILES: O=S(=O)(Oc1ncc(NC23CC4CC(F)(CC(F)(C4)C2)C3)c2c1C1CCC2CC1)C(F)(F)F] | ESI+: 493 |

TABLE 36-continued
| PEx | PSyn | Str | Data |
|---|---|---|---|
| 199 | 36 | 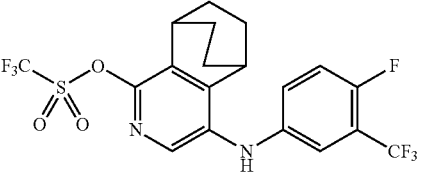 [SMILES: O=S(=O)(Oc1ncc(Nc2ccc(F)c(C(F)(F)F)c2)c2c1C1CCC2CC1)C(F)(F)F] | ESI+: 485 |
| 200 | 36 | 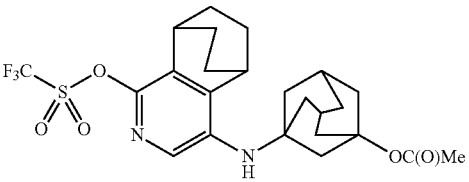 | ESI+: 515 |
| 201 | 13 | 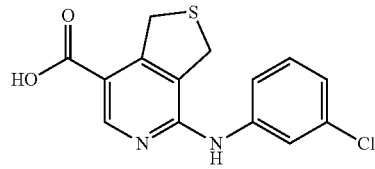 [SMILES: O=C(O)c1cnc(Nc2cccc(Cl)c2)c2c1CSC2] | ESI+: 307/309 |
| 202 | 13 | 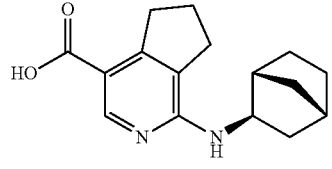 [SMILES: O=C(O)c1cnc(N[C@@H]2C[C@H]3CC[C@@H]2C3)c2c1CCC2] | ESI+: 273 |
| 203 | 36 | 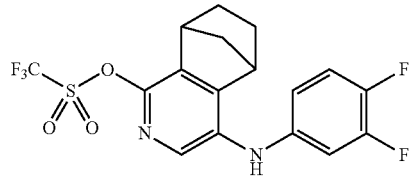 [SMILES: O=S(=O)(Oc1ncc(Nc2ccc(F)c(F)c2)c2c1C1CCC2C1)C(F)(F)F] | ESI+: 421 |
TABLE 37
| PEx | PSyn | Str | Data |
|---|---|---|---|
| 204 | 36 | 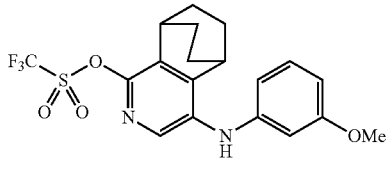 [SMILES: COc1cccc(Nc2cnc(OS(=O)(=O)C(F)(F)F)c3c2C2CCC3CC2)c1] | ESI+: 429 |
| 205 | 22 | 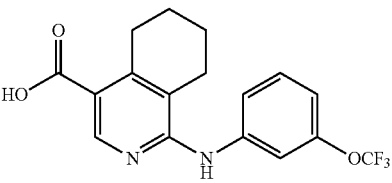 [SMILES: O=C(O)c1cnc(Nc2cccc(OC(F)(F)F)c2)c2c1CCCC2] | ESI+: 353 |
| 206 | 22 | 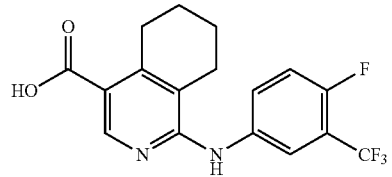 [SMILES: O=C(O)c1cnc(Nc2ccc(F)c(C(F)(F)F)c2)c2c1CCCC2] | ESI+: 353 |
| 207 | 22 | 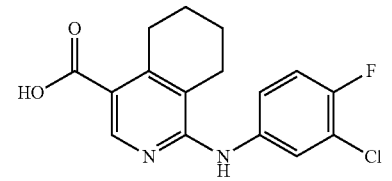 [SMILES: O=C(O)c1cnc(Nc2ccc(F)c(Cl)c2)c2c1CCCC2] | ESI+: 321 |

TABLE 37-continued

| PEx | PSyn | Str | Data |
|---|---|---|---|
| 208 | 22 | | ESI+: 303 |
| 209 | 22 | | ESI+: 317 |
| 210 | 22 | | ESI+: 315 |

TABLE 38

| PEx | PSyn | Str | Data |
|---|---|---|---|
| 211 | 22 | | ESI+: 338 |
| 212 | 22 | | ESI+: 315 |
| 213 | 22 | | ESI+: 367 |
| 214 | 22 | | ESI+: 365 |

TABLE 38-continued

| PEx | PSyn | Str | Data |
|---|---|---|---|
| 215 | 22 | | ESI+: 333 |
| 216 | 22 | | ESI+: 317 |
| 217 | 22 | | ESI+: 317 |

TABLE 39

| PEx | PSyn | Str | Data |
|---|---|---|---|
| 218 | 22 | | ESI+: 295 |
| 219 | 22 | | ESI+: 299 |
| 220 | 22 | | ESI+: 287 |
| 221 | 22 | | ESI+: 350 |

TABLE 39-continued

| PEx | PSyn | Str | Data |
|---|---|---|---|
| 222 | 22 | | ESI+: 355 |
| 223 | 22 | | ESI+: 329 |
| 224 | 22 | | ESI+: 299 |

TABLE 40

| PEx | PSyn | Str | Data |
|---|---|---|---|
| 225 | 22 | | ESI+: 313 |
| 226 | 22 | | ESI+: 309 |
| 227 | 22 | | NMR1: 1.27-1.39 (4H, m), 1.77-1.88 (4H, m), 3.67 (1H, brs), 4.3 (1H, brs), 7.3 (1H, d, J = 7.7 Hz), 7.54 (1H, t, J = 8 Hz), 8.1-8.2 (2H, m), 8.63 (1H, s), 8.91 (1H, s), 12.69 (1H, brs) |
| 228 | 22 | | ESI+: 379 |
| 229 | 22 | | ESI+: 347 |

TABLE 40-continued

| PEx | PSyn | Str | Data |
|---|---|---|---|
| 230 | 22 | (structure) | ESI+: 381 |

TABLE 41

| PEx | PSyn | Str | Data |
|---|---|---|---|
| 231 | 22 | (structure) | ESI+: 312 |
| 232 | 22 | (structure) | ESI+: 369 |
| 233 | 22 | (structure) | ESI+: 389 |
| 234 | 22 | (structure) | ESI+: 331 |
| 235 | 22 | (structure) | NMR1: 1.01-1.20 (2H, m), 1.53 (1H, m), 1.64 (1H, m), 1.88-2.07 (2H, m), 3.78 (3H, s), 3.87 (1H, s), 4.14 (1H, s), 6.57 (1H, m), 7.21 (1H, m), 7.40 (1H, m), 7.49 (1H, s), 8.51 (1H, s), 8.58 (1H, s), 12.6 (1H, s) |
| 236 | 22 | (structure) | ESI+: 375 |

TABLE 42
| PEx | PSyn | Str | Data |
|---|---|---|---|
| 237 | 22 | 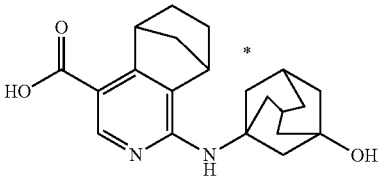 [SMILES: O=C(O)c1cnc(NC23CC4CC(CC(O)(C4)C2)C3)c2c1C1CCC2C1] | ESI+: 355 |
| 238 | 22 | 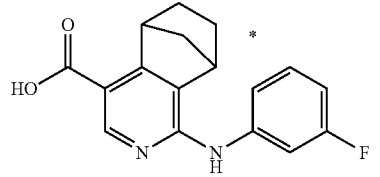 [SMILES: O=C(O)c1cnc(Nc2cccc(F)c2)c2c1C1CCC2C1] | ESI+: 299 |
| 239 | 38 | 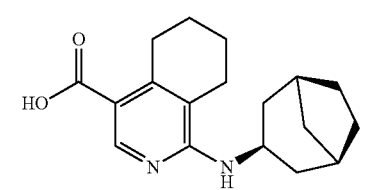 [SMILES: O=C(O)c1cnc(N[C@@H]2C[C@@H]3CC[C@@H](C3)C2)c2c1CCCC2] | ESI+: 301 |
| 240 | 38 | 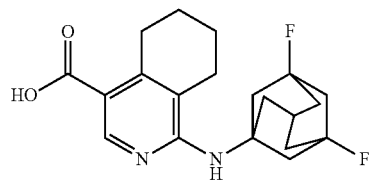 [SMILES: O=C(O)c1cnc(NC23CC4CC(F)(CC(F)(C4)C2)C3)c2c1CCCC2] | ESI+: 363 |
| 241 | 38 | 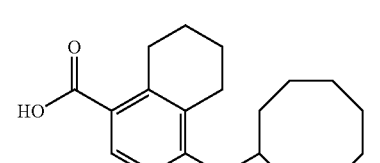 | ESI+: 303 |
| 242 | 38 | 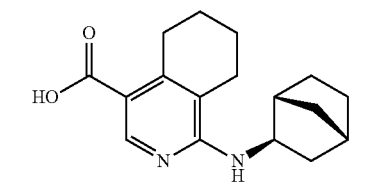 [SMILES: O=C(O)c1cnc(N[C@@H]2C[C@H]3CC[C@@H]2C3)c2c1CCCC2] | ESI+: 287 |
| 243 | 38 | 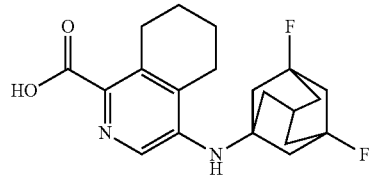 [SMILES: O=C(O)c1ncc(NC23CC4CC(F)(CC(F)(C4)C2)C3)c2c1CCCC2] | ESI+: 363 |
TABLE 43
| PEx | PSyn | Str | Data |
|---|---|---|---|
| 244 | 38 | 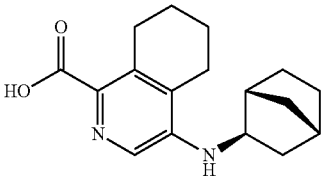 [SMILES: O=C(O)c1ncc(N[C@@H]2C[C@H]3CC[C@@H]2C3)c2c1CCCC2] | ESI+: 287 |
| 245 | 38 | 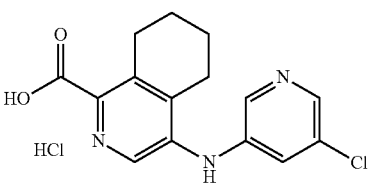 [SMILES: O=C(O)c1ncc(Nc2cncc(Cl)c2)c2c1CCCC2 ; Cl] | ESI+: 304 |
| 246 | 38 | 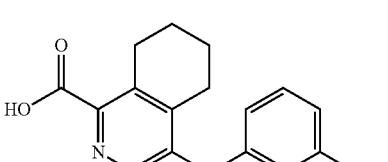 | ESI+: 338 |
| 247 | 38 | 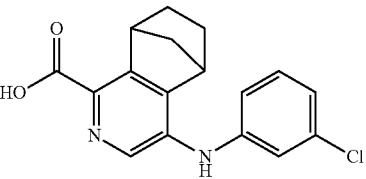 [SMILES: O=C(O)c1ncc(Nc2cccc(Cl)c2)c2c1C1CCC2C1] | ESI+: 315 |
| 248 | 38 | 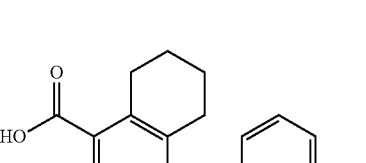 | ESI+: 320 |
| 249 | 38 | 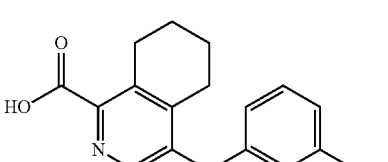 | ESI−: 335 |
| 250 | 38 | 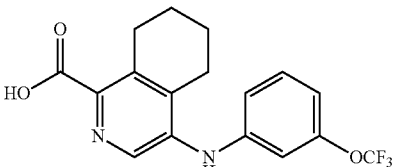 | ESI−: 351 |

TABLE 44

| PEx | PSyn | Str | Data |
|---|---|---|---|
| 251 | 38 | (structure) | ESI+: 333 |
| 252 | 38 | (structure) | ESI+: 367 |
| 253 | 38 | (structure) | ESI+: 349 |
| 254 | 38 | (structure) | ESI+: 375 |
| 255 | 38 | (structure) | ESI+: 363 |
| 256 | 38 | (structure) | ESI+: 359 |
| 257 | 38 | (structure) | ESI+: 295 |

TABLE 45

| PEx | PSyn | Str | Data |
|---|---|---|---|
| 258 | 38 | (structure) | ESI+: 329 |
| 259 | 38 | (structure) | ESI+: 347/349 |
| 260 | 38 | (structure) | ESI+: 306 |
| 261 | 38 | (structure) | ESI+: 379 |
| 262 | 38 | (structure) | ESI+: 331 |
| 263 | 38 | (structure) | ESI+: 313 |
| 264 | 38 | (structure) | ESI+: 309 |

TABLE 46
| PEx | PSyn | Str | Data |
|---|---|---|---|
| 265 | 38 | 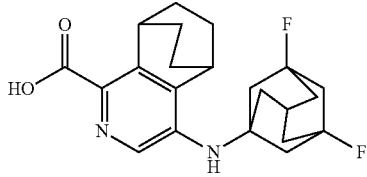 [SMILES: O=C(O)c1ncc(NC23CC4CC(F)(CC(F)(C4)C2)C3)c2c1C1CCC2CC1] | ESI+: 389 |
| 266 | 38 | 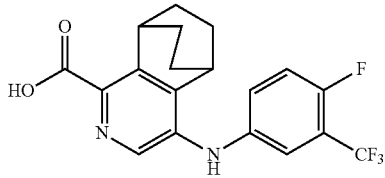 [SMILES: O=C(O)c1ncc(Nc2ccc(F)c(C(F)(F)F)c2)c2c1C1CCC2CC1] | ESI+: 381 |
| 267 | 38 | 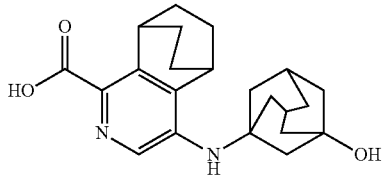 [SMILES: O=C(O)c1ncc(NC23CC4CC(CC(O)(C4)C2)C3)c2c1C1CCC2CC1] | ESI+: 369 |
| 268 | 38 | 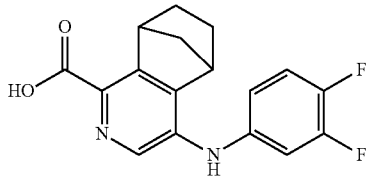 [SMILES: O=C(O)c1ncc(Nc2ccc(F)c(F)c2)c2c1C1CCC2C1] | ESI+: 317 |
| 269 | 38 | 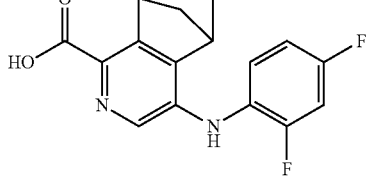 | ESI+: 317 |
| 270 | 38 | 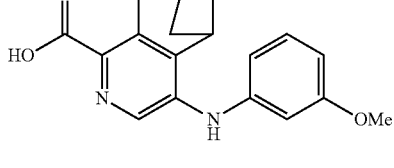 | ESI+: 325 |
| 271 | 26 | 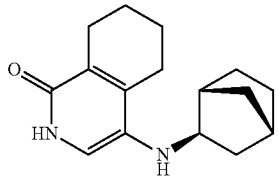 [SMILES: O=c1[nH]cc(N[C@@H]2C[C@H]3CC[C@@H]2C3)c2c1CCCC2] | ESI+: 259 |
TABLE 47
| PEx | PSyn | Str | Data |
|---|---|---|---|
| 272 | 9 | 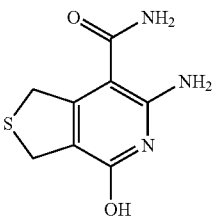 [SMILES: NC(=O)c1c(N)nc(O)c2c1CSC2] | ESI+: 212 |
| 273 | 11 | 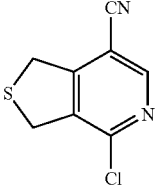 [SMILES: N#Cc1cnc(Cl)c2c1CSC2] | ESI+: 197/199 |
| 274 | 26 | 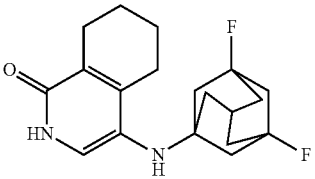 [SMILES: O=c1[nH]cc(NC23CC4CC(F)(CC(F)(C4)C2)C3)c2c1CCCC2] | ESI+: 335 |
| 275 | 26 | 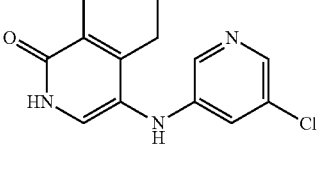 | ESI+: 276 |
| 276 | 26 | 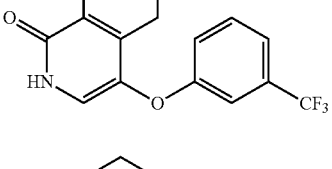 | ESI+: 310 |
| 277 | 26 | 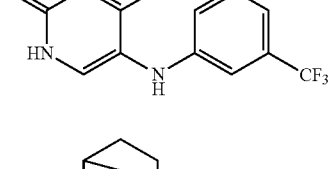 | ESI+: 309 |
| 278 | 35 | 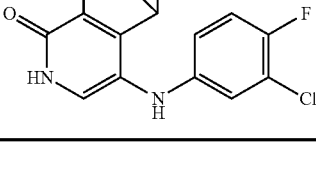 | ESI+: 305 |

TABLE 48

| PEx | PSyn | Str | Data |
|---|---|---|---|
| 279 | 26 | 4,5,6,7-tetrahydroisoquinolin-1(2H)-one with 4-NH-(3-OCF3-phenyl) | ESI+: 325 |
| 280 | 26 | 4,5,6,7-tetrahydroisoquinolin-1(2H)-one with 4-S-(3-Cl-phenyl) | ESI+: 292 |
| 281 | 35 | bicyclic isoquinolinone with 4-NH-(3-Cl-phenyl) | ESI+: 287 |
| 282 | 35 | bicyclic isoquinolinone with 4-NH-(3-CF3-phenyl) | ESI+: 321 |
| 283 | 35 | bicyclic isoquinolinone with 4-NH-(4-F-3-CF3-phenyl) | ESI+: 339 |
| 284 | 35 | bicyclic isoquinolinone with 4-NH-(3,5-diF-adamantyl) | ESI+: 347 |
| 285 | 35 | bicyclic isoquinolinone with 4-NH-(3-SO2Me-phenyl) | ESI+: 331 |

TABLE 49

| PEx | PSyn | Str | Data |
|---|---|---|---|
| 286 | 35 | bicyclic isoquinolinone with 4-NH-(3-CF3-phenyl) | ESI+: 335 |
| 287 | 35 | bicyclic isoquinolinone with 4-NH-(3-Me-phenyl) | ESI+: 269 |
| 288 | 35 | bicyclic isoquinolinone with 4-NH-(3-Cl-phenyl) | ESI+: 301 |
| 289 | 35 | bicyclic isoquinolinone with 4-NH-(3-CN-phenyl) | ESI+: 278 |
| 290 | 35 | bicyclic isoquinolinone with 4-NH-(4-F-3-Cl-phenyl) | ESI+: 319/321 |
| 291 | 35 | bicyclic isoquinolinone with 4-NH-(3-Me-phenyl) | ESI+: 281 |
| 292 | 35 | bicyclic isoquinolinone with 4-NH-(3-OCF3-phenyl) | ESI+: 351 |

TABLE 50
| PEx | PSyn | Str | Data |
|---|---|---|---|
| 293 | 35 | 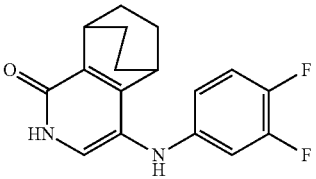 [SMILES: O=c1[nH]cc(Nc2ccc(F)c(F)c2)c2c1C1CCC2CC1] | ESI+: 303 |
| 294 | 35 | 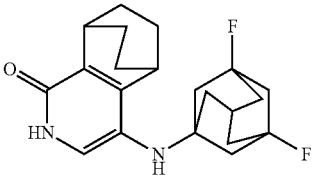 [SMILES: O=c1[nH]cc(NC23CC4CC(F)(CC(F)(C4)C2)C3)c2c1C1CCC2CC1] | ESI+: 361 |
| 295 | 35 | 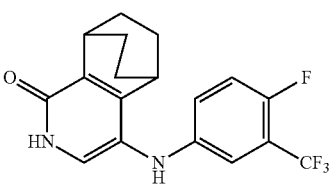 [SMILES: O=c1[nH]cc(Nc2ccc(F)c(C(F)(F)F)c2)c2c1C1CCC2CC1] | ESI+: 353 |
| 296 | 35 | 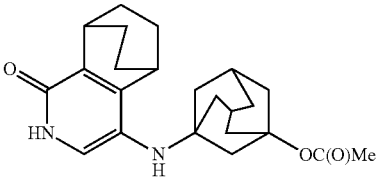 | ESI+: 383 |
| 297 | 35 | 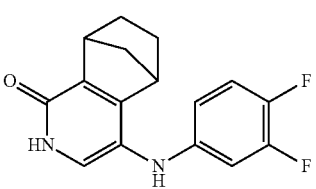 [SMILES: O=c1[nH]cc(Nc2ccc(F)c(F)c2)c2c1C1CCC2C1] | ESI+: 289 |
| 298 | 35 | 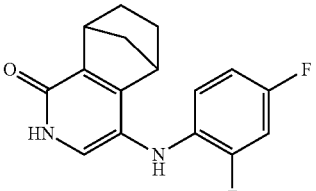 | ESI+: 289 |
| 299 | 39 | 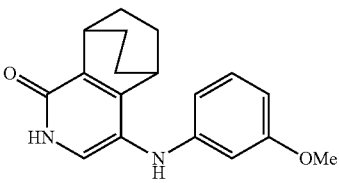 [SMILES: COc1cccc(Nc2c[nH]c(=O)c3c2C2CCC3CC2)c1] | ESI+: 297 |
TABLE 51
| PEx | PSyn | Str | Data |
|---|---|---|---|
| 300 | 37 | 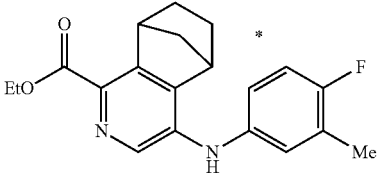 [SMILES: CCOC(=O)c1ncc(Nc2ccc(F)c(C)c2)c2c1C1CCC2C1] | ESI+: 341 |
| 301 | 37 | 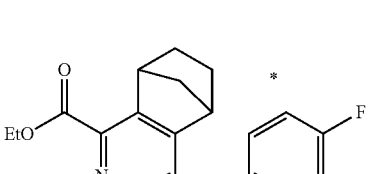 | ESI+: 357 |
| 302 | 37 | 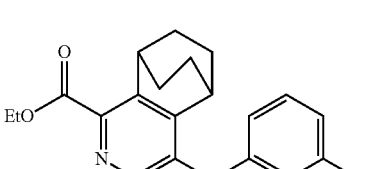 | ESI+: 355 |
| 303 | 37 | 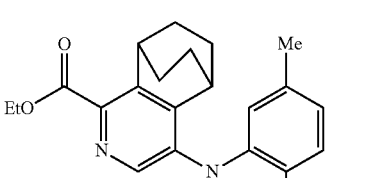 | ESI+: 355 |
| 304 | 37 | 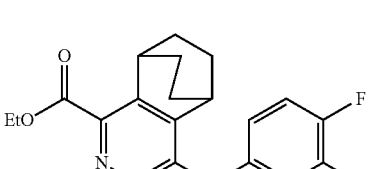 | ESI+: 355 |
| 305 | 37 | 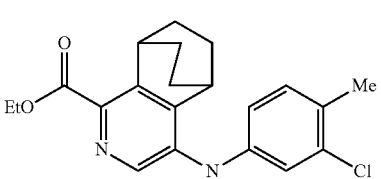 | ESI+: 371/373 |
| 306 | 37 | 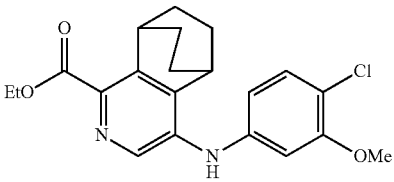 | ESI+: 387/389 |

TABLE 52
| PEx | PSyn | Str | Data |
|---|---|---|---|
| 307 | 34 | 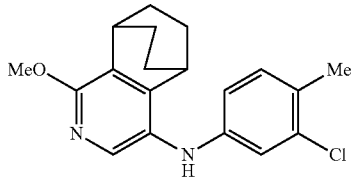 [SMILES: COc1ncc(Nc2ccc(C)c(Cl)c2)c2c1C1CCC2CC1] | ESI+: 329/331 |
| 308 | 34 | 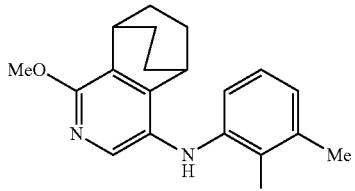 | ESI+: 313 |
| 309 | 34 | 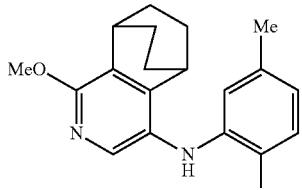 | ESI+: 313 |
| 310 | 41 | 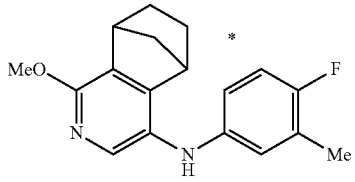 [SMILES: COc1ncc(Nc2ccc(F)c(C)c2)c2c1C1CCC2C1] | ESI+: 299 |
| 311 | 34 | 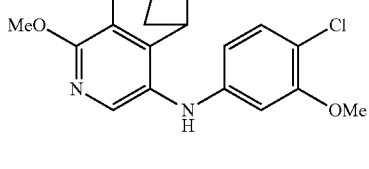 | ESI+: 345/347 |
| 312 | 41 | 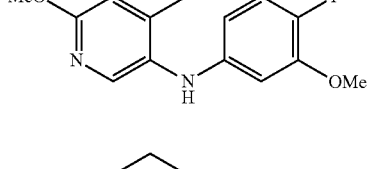 | ESI+: 315 |
| 313 | 41 | 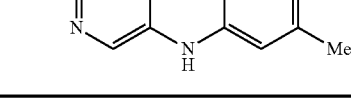 | ESI+: 313 |
TABLE 53
| PEx | PSyn | Str | Data |
|---|---|---|---|
| 314 | 21 | 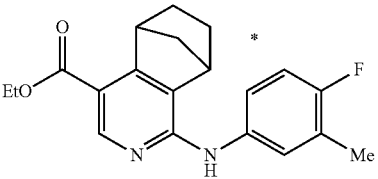 [SMILES: CCOC(=O)c1cnc(Nc2ccc(F)c(C)c2)c2c1C1CCC2C1] | ESI+: 341 |
| 315 | 21 | 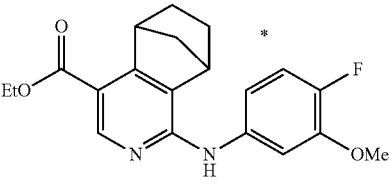 [SMILES: CCOC(=O)c1cnc(Nc2ccc(F)c(OC)c2)c2c1C1CCC2C1] | ESI+: 357 |
| 316 | 21 | 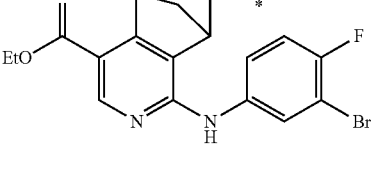 | ESI+: 405/407 |
| 317 | 21 | 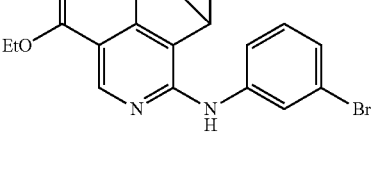 | ESI+: 387/389 |
| 318 | 21 | 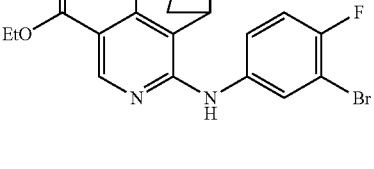 | ESI+: 419/421 |
| 319 | 21 | 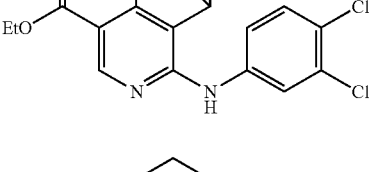 | ESI+: 377 |
| 320 | 21 | 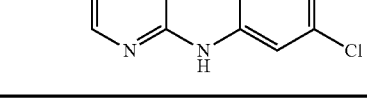 | ESI+: 357 |

TABLE 54

| PEx | PSyn | Str | Data |
|---|---|---|---|
| 321 | 21 | (structure) | ESI+: 361 |
| 322 | 21 | (structure) | ESI+: 401/403 |
| 323 | 21 | (structure) | ESI+: 391 |
| 324 | 21 | (structure) | ESI+: 371 |

TABLE 54-continued

| PEx | PSyn | Str | Data |
|---|---|---|---|
| 325 | 21 | (structure) | ESI+: 375 |
| 326 | 21 | (structure) | ESI+: 355 |
| 327 | 21 | (structure) | ESI+: 375 |

TABLE 55

| PEx | PSyn | Str | Data |
|---|---|---|---|
| 328 | 21 | (structure) | ESI+: 391 |
| 329 | 36 | (structure) | ESI+: 417 |
| 330 | 36 | (structure) | ESI+: 433 |

TABLE 55-continued

| PEx | PSyn | Str | Data |
|---|---|---|---|
| 331 | 36 | (F3C-SO2-O-[bicyclic pyridine]-NH-[4-F, 3-Me phenyl]) | ESI+: 431 |
| 332 | 36 | (F3C-SO2-O-[bicyclic pyridine]-NH-[4-Me, 3-Cl phenyl]) | ESI+: 447/449 |
| 333 | 36 | (F3C-SO2-O-[bicyclic pyridine]-NH-[2-F, 3-Me phenyl]) | ESI+: 431 |
| 334 | 36 | (F3C-SO2-O-[bicyclic pyridine]-NH-[5-Me, 2-F phenyl]) | ESI+: 431 |

TABLE 56

| PEx | PSyn | Str | Data |
|---|---|---|---|
| 335 | 36 | (F3C-SO2-O-[bicyclic pyridine]-NH-[4-Cl, 3-OMe phenyl]) | ESI+: 463/465 |
| 336 | 22 | (HOOC-[bicyclic pyridine]*-NH-[4-F, 3-Me phenyl]) | ESI+: 313 |
| 337 | 22 | (HOOC-[bicyclic pyridine]*-NH-[4-F, 3-OMe phenyl]) | ESI+: 329 |
| 338 | 22 | (HOOC-[bicyclic pyridine]*-NH-[4-F, 3-Br phenyl]) | ESI+: 377/379 |
| 339 | 22 | (HOOC-[bicyclic pyridine]*-NH-[3-Br phenyl]) | ESI+: 359/361 |
| 340 | 22 | (HOOC-[bicyclic pyridine]*-NH-[4-Me, 3-Cl phenyl]) | ESI+: 329 |

TABLE 56-continued

| PEx | PSyn | Str | Data |
|-----|------|-----|------|
| 341 | 22 | (carboxylic acid-substituted bicyclic pyridine with 3,4-dichlorophenylamino group) | ESI+: 349 |

TABLE 57

| PEx | PSyn | Str | Data |
|-----|------|-----|------|
| 342 | 22 | (carboxylic acid-substituted bicyclic pyridine with 4-chloro-3-fluorophenylamino group) | ESI+: 333 |
| 343 | 22 | (carboxylic acid-substituted bicyclic pyridine with 3-bromo-4-fluorophenylamino group) | ESI+: 391/ 393 |
| 344 | 22 | (carboxylic acid-substituted bicyclic pyridine with 3-bromophenylamino group) | ESI+: 373/ 375 |
| 345 | 22 | (carboxylic acid-substituted bicyclic pyridine with 3,4-dichlorophenylamino group) | ESI+: 363 |
| 346 | 22 | (carboxylic acid-substituted bicyclic pyridine with 3-chloro-4-methylphenylamino group) | ESI+: 343 |
| 347 | 22 | (carboxylic acid-substituted bicyclic pyridine with 4-chloro-3-fluorophenylamino group) | ESI+: 347 |

TABLE 57-continued

| PEx | PSyn | Str | Data |
|-----|------|-----|------|
| 348 | 38 | (carboxylic acid-substituted bicyclic pyridine with 4-fluoro-3-methylphenylamino group) | ESI+: 313 |

TABLE 58

| PEx | PSyn | Str | Data |
|-----|------|-----|------|
| 349 | 38 | (carboxylic acid-substituted bicyclic pyridine with 4-fluoro-3-methoxyphenylamino group) | ESI+: 329 |
| 350 | 38 | (carboxylic acid-substituted bicyclic pyridine with 3-chloro-4-methylphenylamino group) | ESI+: 343/ 345 |
| 351 | 38 | (carboxylic acid-substituted bicyclic pyridine with 2-fluoro-3-methylphenylamino group) | ESI+: 327 |
| 352 | 38 | (carboxylic acid-substituted bicyclic pyridine with 2-fluoro-5-methylphenylamino group) | ESI+: 327 |
| 353 | 38 | (carboxylic acid-substituted bicyclic pyridine with 4-fluoro-3-methylphenylamino group) | ESI+: 327 |
| 354 | 38 | (carboxylic acid-substituted bicyclic pyridine with 4-chloro-3-methoxyphenylamino group) | ESI+: 359/ 361 |

TABLE 58-continued

| PEx | PSyn | Str | Data |
|---|---|---|---|
| 355 | 35 | | ESI+: 285 |

TABLE 59

| PEx | PSyn | Str | Data |
|---|---|---|---|
| 356 | 35 | | ESI+: 299 |
| 357 | 35 | | ESI+: 299 |
| 358 | 35 | | ESI+: 299 |
| 359 | 35 | | ESI+: 315/317 |
| 360 | 39 | | ESI+: 301 |
| 361 | 39 | | ESI+: 331/333 |

TABLE 60

| PEx | PSyn | Str | Data |
|---|---|---|---|
| 362 | 22 | | ESI+: 327 |
| 363 | 22 | | ESI+: 347 |
| 364 | 22 | | ESI+: 363 |
| 365 | 37 | | ESI+: 375/377 |
| 366 | 15 | | ESI+: 190 |
| 367 | 16 | | ESI+: 268 |
| 368 | 17 | | ESI+: 262 |
| 369 | 18 | | ESI+: 248 |

TABLE 61
| PEx | PSyn | Str | Data |
|---|---|---|---|
| 370 | 22 | | ESI+: 381 |
| 371 | 46 | | ESI+: 409 |
| 372-1 | 17 | * | ESI+: 248 |
| 372-2 | 17 | * | ESI+: 248 |
| 373-1 | 18 | * | ESI+: 234 |
| 373-2 | 18 | * | ESI+: 234 |
TABLE 2
| Ex | Str |
|---|---|
| 1 | |
| 2 | |
| 3 | |
| 4 | HCl |
| 5-1 | * HCl |
| 5-2 | * HCl |
| 6 | |
TABLE 63
| Ex | Str |
|---|---|
| 7-1 | * HCl |
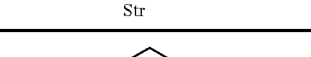
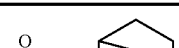

TABLE 63-continued
| Ex | Str |
|---|---|
| 7-2 | 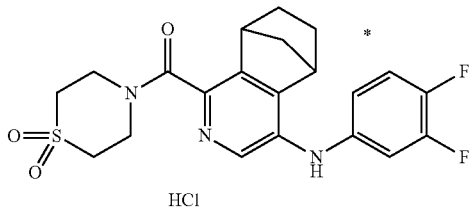 [SMILES: O=C(c1ncc(Nc2ccc(F)c(F)c2)c2c1C1CCC2C1)N1CCS(=O)(=O)CC1 ; Cl] HCl |
| 8 | 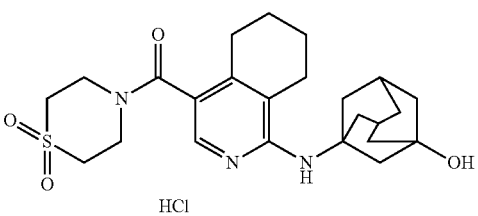 [SMILES: O=C(c1cnc(NC23CC4CC(CC(O)(C4)C2)C3)c2c1CCCC2)N1CCS(=O)(=O)CC1 ; Cl] HCl |
| 9 | 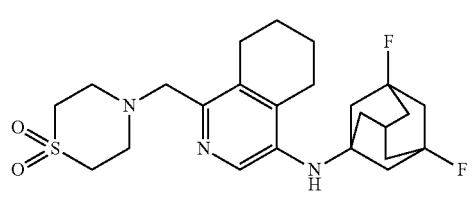 [SMILES: O=S1(=O)CCN(Cc2ncc(NC34CC5CC(F)(CC(F)(C5)C3)C4)c3c2CCCC3)CC1] |
| 10 | 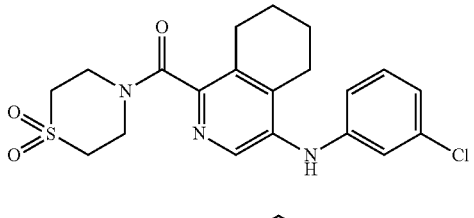 |
| 11 | 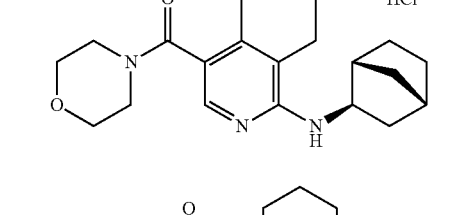 HCl |
| 12 | 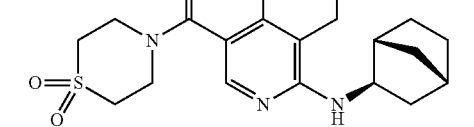 |
TABLE 64
| Ex | Str |
|---|---|
| 13 | 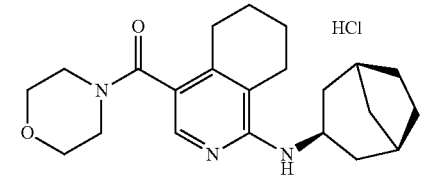 [SMILES: O=C(c1cnc(N[C@@H]2C[C@@H]3CC[C@@H](C3)C2)c2c1CCCC2)N1CCOCC1 ; Cl] HCl |
TABLE 64-continued
| Ex | Str |
|---|---|
| 14 | 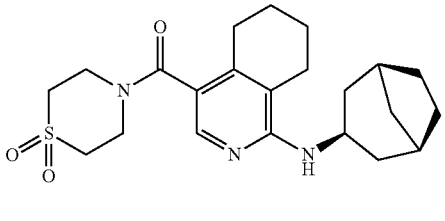 [SMILES: O=C(c1cnc(N[C@@H]2C[C@@H]3CC[C@@H](C3)C2)c2c1CCCC2)N1CCS(=O)(=O)CC1] |
| 15 | 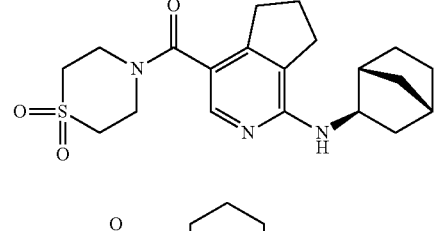 |
| 16 | 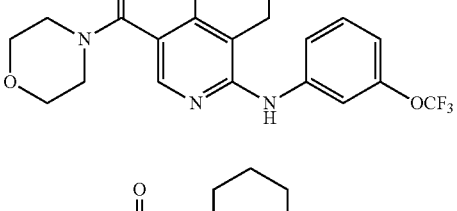 |
| 17 | 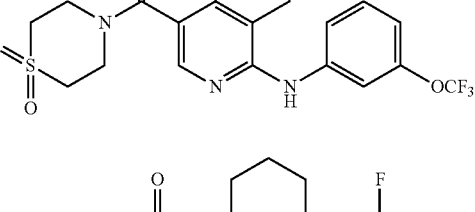 |
| 18 | 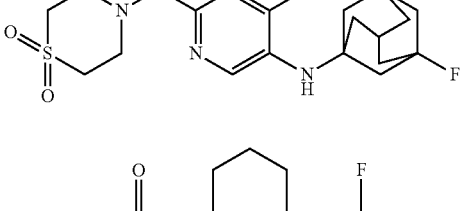 |
| 19 | 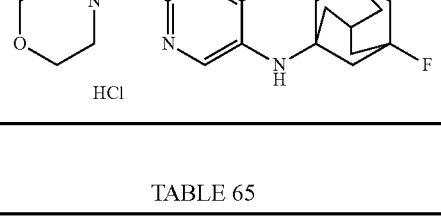 HCl |
TABLE 65
| Ex | Str |
|---|---|
| 20 | 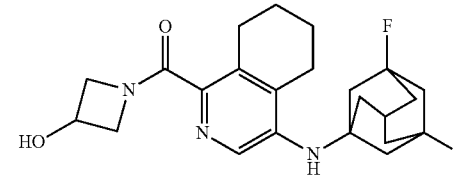 |

TABLE 65-continued
| Ex | Str |
|---|---|
| 21 | 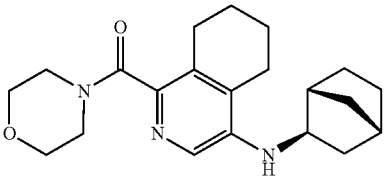 [SMILES: O=C(c1ncc(N[C@@H]2C[C@H]3CC[C@@H]2C3)c2c1CCCC2)N1CCOCC1] |
| 22 | 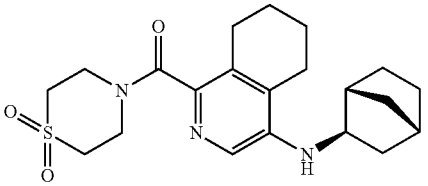 [SMILES: O=C(c1ncc(N[C@@H]2C[C@H]3CC[C@@H]2C3)c2c1CCCC2)N1CCS(=O)(=O)CC1] |
| 23 |  |
| 24 | 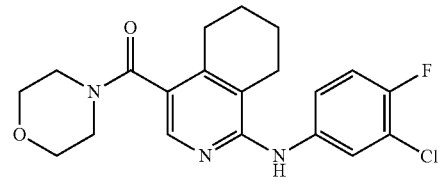 [SMILES: O=C(c1cnc(Nc2ccc(F)c(Cl)c2)c2c1CCCC2)N1CCOCC1] |
| 25 |  |
| 26 | 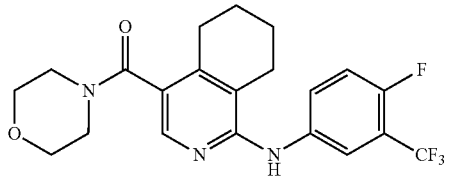 [SMILES: O=C(c1cnc(Nc2ccc(F)c(C(F)(F)F)c2)c2c1CCCC2)N1CCOCC1] |
TABLE 66
| Ex | Str |
|---|---|
| 27 | 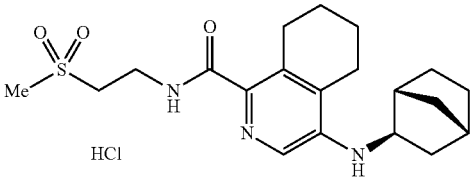 [SMILES: CS(=O)(=O)CCNC(=O)c1ncc(N[C@@H]2C[C@H]3CC[C@@H]2C3)c2c1CCCC2 ; Cl] |
TABLE 66-continued
| Ex | Str |
|---|---|
| 28 |  |
| 29 | 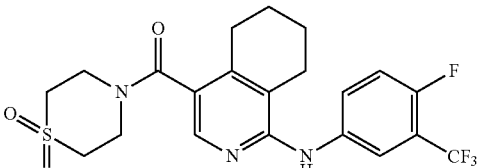 |
| 30 | 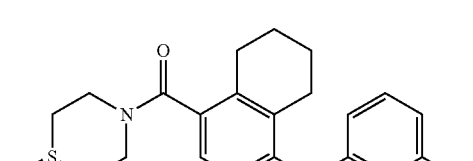 |
| 31 |  |
| 32 | 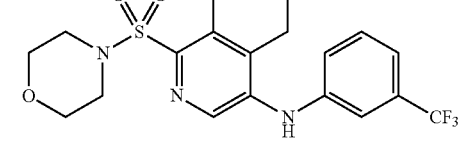 |
| 33 | 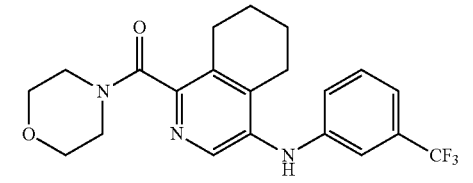 [SMILES: O=C(c1ncc(Nc2cccc(C(F)(F)F)c2)c2c1CCCC2)N1CCOCC1] |
TABLE 67
| Ex | Str |
|---|---|
| 34 | 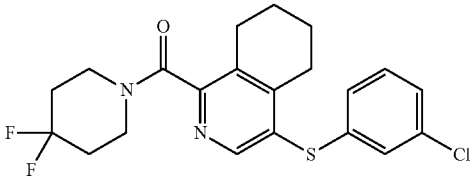 [SMILES: O=C(c1ncc(Sc2cccc(Cl)c2)c2c1CCCC2)N1CCC(F)(F)CC1] |

TABLE 67-continued

| Ex | Str |
|---|---|
| 35 | |
| 36 | |
| 37 | |
| 38 | |
| 39 | |
| 40 | |

TABLE 68

| Ex | Str |
|---|---|
| 41 | |

TABLE 68-continued

| Ex | Str |
|---|---|
| 42 | |
| 43 | |
| 44 | |
| 45 | |
| 46 | |
| 47 | |

TABLE 69

| Ex | Str |
|---|---|
| 48 | |

TABLE 69-continued

| Ex | Str |
|---|---|
| 49 | (structure) |
| 50 | (structure) |
| 51 | (structure) |
| 52 | (structure) |
| 53 | (structure) |
| 54 | (structure) |

TABLE 70

| Ex | Str |
|---|---|
| 55 | (structure) |
| 56 | (structure) |
| 57 | (structure) |
| 58 | (structure) |
| 59 | (structure) |
| 60 | (structure) |
| 61 | (structure) |

TABLE 71

| Ex | Str |
|---|---|
| 62 | (structure) |

TABLE 71-continued

| Ex | Str |
|---|---|
| 63 | (structure) |
| 64 | (structure) |
| 65 | (structure) |
| 66 | (structure) |
| 67 | (structure) |
| 68 | (structure) |

TABLE 72

| Ex | Str |
|---|---|
| 69 | (structure) |
| 70 | (structure) |
| 71 | (structure) |
| 72 | (structure) |
| 73 | (structure) |
| 74 | (structure) |
| 75 | (structure) |

TABLE 73

| Ex | Str |
|---|---|
| 76 | (structure) |

TABLE 73-continued
| Ex | Str |
|---|---|
| 77 |  |
| 78 | 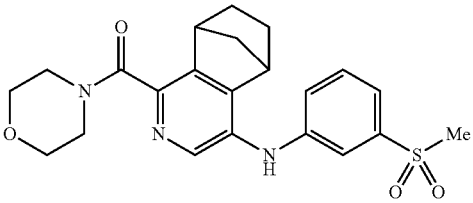 [SMILES: CS(=O)(=O)c1cccc(Nc2cnc(C(=O)N3CCOCC3)c3c2C2CCC3C2)c1] |
| 79 | 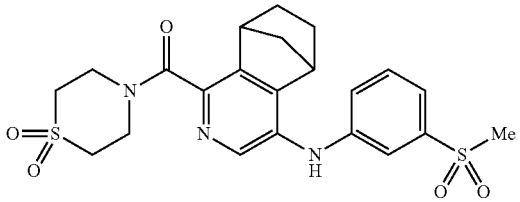 [SMILES: CS(=O)(=O)c1cccc(Nc2cnc(C(=O)N3CCS(=O)(=O)CC3)c3c2C2CCC3C2)c1] |
| 80 | 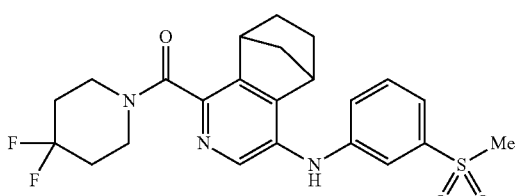 |
| 81 | 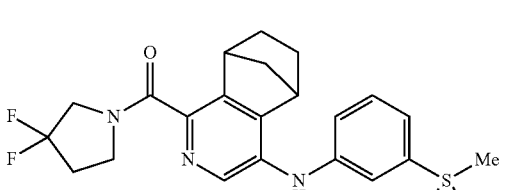 |
| 82 | 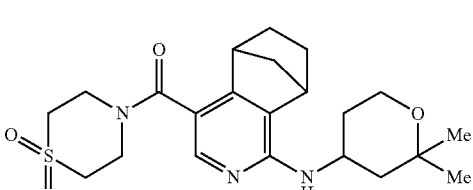 |
TABLE 74
| Ex | Str |
|---|---|
| 83 | 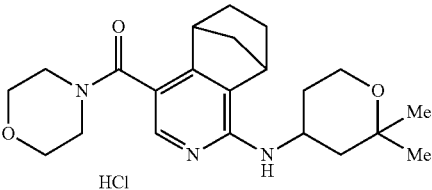 |
| 84 | 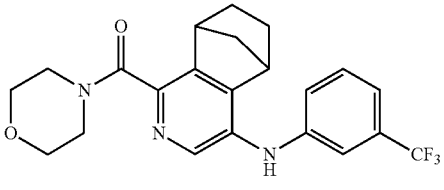 [SMILES: O=C(c1ncc(Nc2cccc(C(F)(F)F)c2)c2c1C1CCC2C1)N1CCOCC1] |
| 85 | 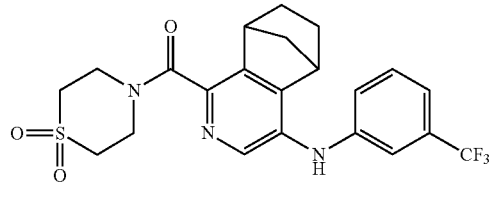 [SMILES: O=C(c1ncc(Nc2cccc(C(F)(F)F)c2)c2c1C1CCC2C1)N1CCS(=O)(=O)CC1] |
| 86 | 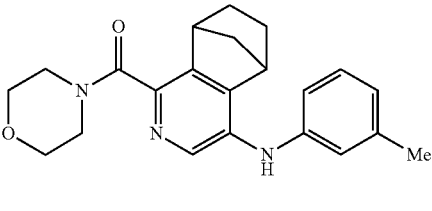 [SMILES: Cc1cccc(Nc2cnc(C(=O)N3CCOCC3)c3c2C2CCC3C2)c1] |
| 87 | 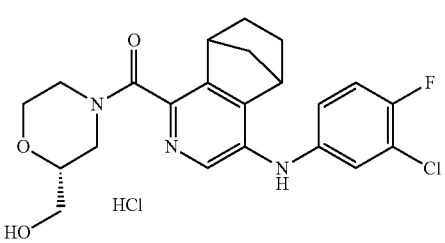 [SMILES: O=C(c1ncc(Nc2ccc(F)c(Cl)c2)c2c1C1CCC2C1)N1CCO[C@@H](CO)C1 ; Cl] |
| 88 | 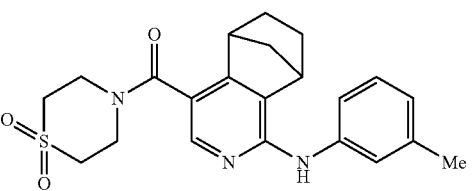 [SMILES: Cc1cccc(Nc2ncc(C(=O)N3CCS(=O)(=O)CC3)c3c2C2CCC3C2)c1] |
| 89 | |

TABLE 75

| Ex | Str |
|---|---|
| 90 | (morpholine-C(O)-[bicyclic fused pyridine]-NH-(3-methylphenyl)) |
| 91 | (thiomorpholine-1,1-dioxide-C(O)-[tetrahydroisoquinoline]-NH-(norbornyl)) |
| 92 | (thiomorpholine-1,1-dioxide-C(O)-[bicyclic fused pyridine]-NH-(norbornyl)) |
| 93 | (morpholine-C(O)-[bicyclic fused pyridine]-NH-(norbornyl)) |
| 94-1 | (thiomorpholine-1,1-dioxide-C(O)-[bicyclic fused pyridine]-NH-(3-chlorophenyl)) * |
| 94-2 | (thiomorpholine-1,1-dioxide-C(O)-[bicyclic fused pyridine]-NH-(3-chlorophenyl)) * |
| 95 | (thiomorpholine-1,1-dioxide-C(O)-[bicyclic fused pyridine]-O-(3-trifluoromethylphenyl)) |
| 96 | (morpholine-C(O)-[bicyclic fused pyridine]-O-(3-trifluoromethylphenyl)) |

TABLE 76

| Ex | Str |
|---|---|
| 97 | (morpholine-C(O)-[bicyclic fused pyridine]-NH-(3-chlorophenyl)) HCl |
| 98 | (thiomorpholine-1,1-dioxide-C(O)-[bicyclic fused pyridine]-NH-(3-chlorophenyl)) HCl |
| 99 | (thiomorpholine-1,1-dioxide-C(O)-[bicyclic fused pyridine]-NH-(hydroxyadamantyl)) HCl |
| 100 | (morpholine-C(O)-[bicyclic fused pyridine]-NH-(hydroxyadamantyl)) HCl |
| 101 | (thiomorpholine-1,1-dioxide-C(O)-[bicyclic fused pyridine]-NH-(3-chlorophenyl)) HCl |
| 102 | (morpholine-C(O)-[bicyclic fused pyridine]-NH-(3-chlorophenyl)) HCl |
| 103 | (thiomorpholine-1,1-dioxide-C(O)-[bicyclic fused pyridine]-NH-(3-trifluoromethoxyphenyl)) HCl |

TABLE 77
| Ex | Str |
|---|---|
| 104 | 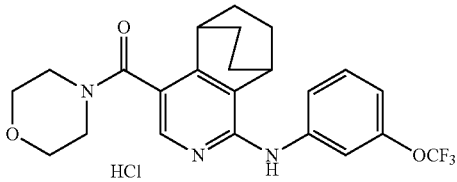 [SMILES: O=C(c1cnc(Nc2cccc(OC(F)(F)F)c2)c2c1C1CCC2CC1)N1CCOCC1 ; Cl] |
| 105 |  |
| 106 | 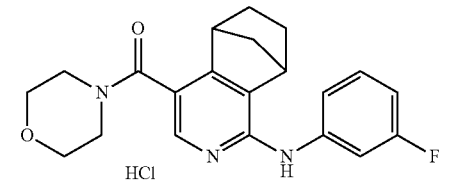 [SMILES: O=C(c1cnc(Nc2cccc(F)c2)c2c1C1CCC2C1)N1CCOCC1 ; Cl] |
| 107 | 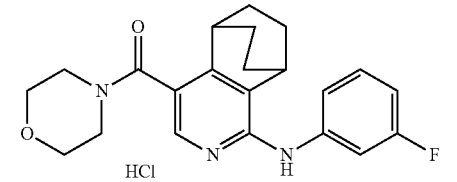 [SMILES: O=C(c1cnc(Nc2cccc(F)c2)c2c1C1CCC2CC1)N1CCOCC1 ; Cl] |
| 108 | 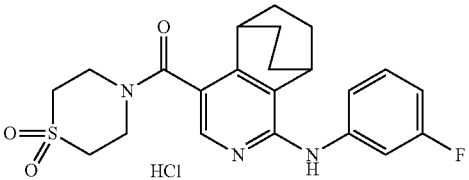 [SMILES: O=C(c1cnc(Nc2cccc(F)c2)c2c1C1CCC2CC1)N1CCS(=O)(=O)CC1 ; Cl] |
| 109 | 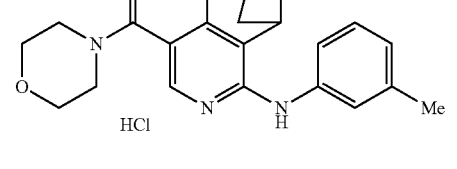 |
| 110 | 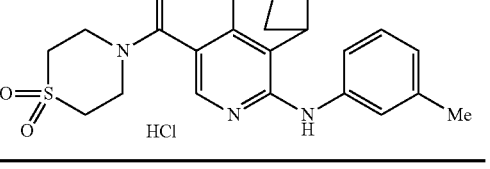 |
TABLE 78
| Ex | Str |
|---|---|
| 111 | 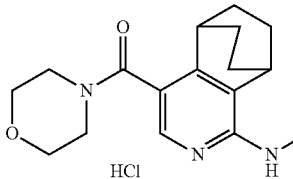 |
| 112 | 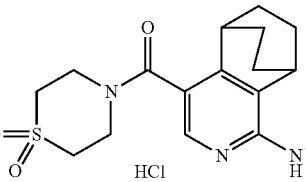 |
| 113 | 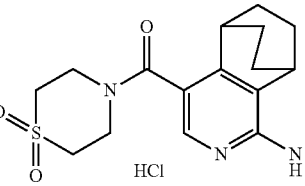 |
| 114 | 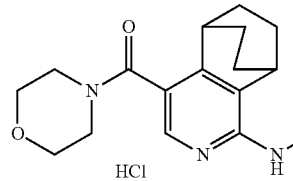 |
| 115 | 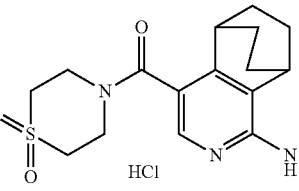 |
| 116 | 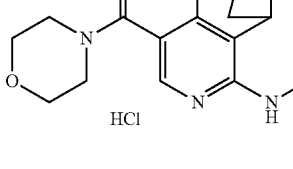 |
| 117-1 | 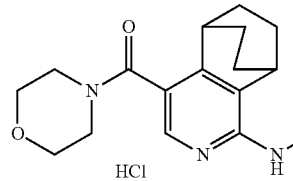 |

US 8,791,106 B2
TABLE 79
| Ex | Str |
|---|---|
| 117-2 | 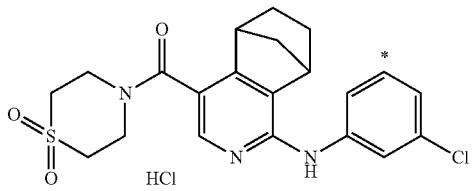 [SMILES: O=C(c1cnc(Nc2cccc(Cl)c2)c2c1C1CCC2C1)N1CCS(=O)(=O)CC1 ; Cl] |
| 118 | 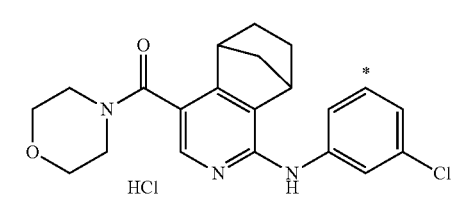 [SMILES: O=C(c1cnc(Nc2cccc(Cl)c2)c2c1C1CCC2C1)N1CCOCC1 ; Cl] |
| 119-1 | 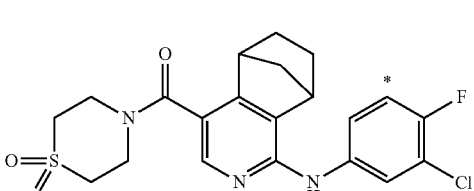 |
| 119-2 | 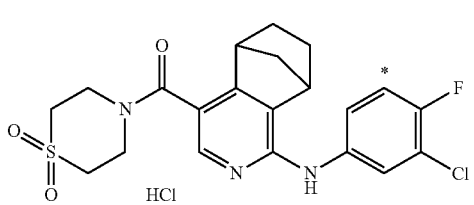 [SMILES: O=C(c1cnc(Nc2ccc(F)c(Cl)c2)c2c1C1CCC2C1)N1CCS(=O)(=O)CC1 ; Cl] |
| 120-1 | 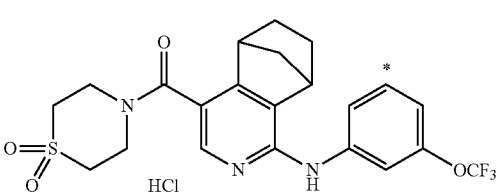 [SMILES: O=C(c1cnc(Nc2cccc(OC(F)(F)F)c2)c2c1C1CCC2C1)N1CCS(=O)(=O)CC1 ; Cl] |
| 120-2 | 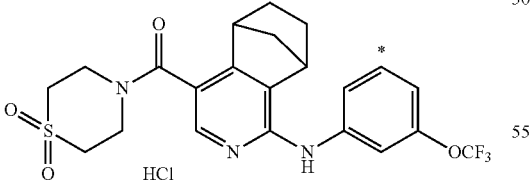 |
| 121 | 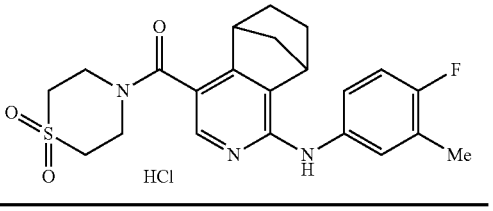 |
TABLE 80
| Ex | Str |
|---|---|
| 122 | 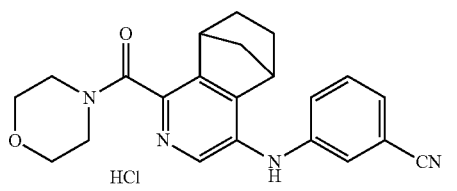 [SMILES: N#Cc1cccc(Nc2cnc(C(=O)N3CCOCC3)c3c2C2CCC3C2)c1 ; Cl] |
| 123 | 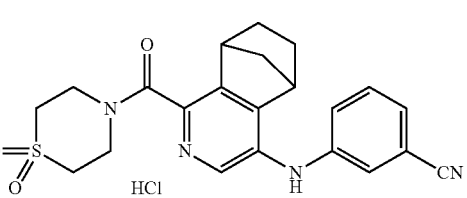 |
| 124 | 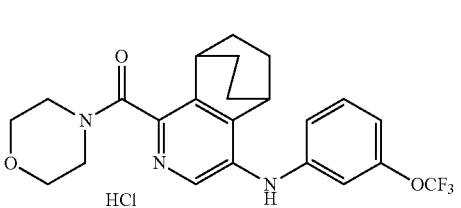 [SMILES: O=C(c1ncc(Nc2cccc(OC(F)(F)F)c2)c2c1C1CCC2CC1)N1CCOCC1 ; Cl] |
| 125 | 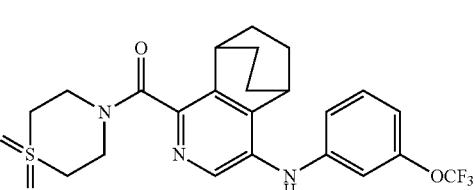 |
| 126 | 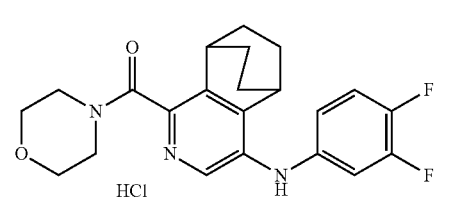 [SMILES: O=C(c1ncc(Nc2ccc(F)c(F)c2)c2c1C1CCC2CC1)N1CCOCC1 ; Cl] |
| 127 | 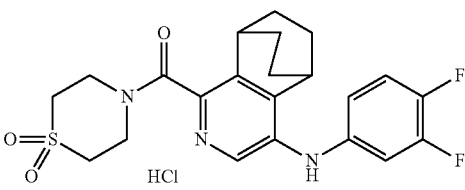 [SMILES: O=C(c1ncc(Nc2ccc(F)c(F)c2)c2c1C1CCC2CC1)N1CCS(=O)(=O)CC1 ; Cl] |
| 128 | 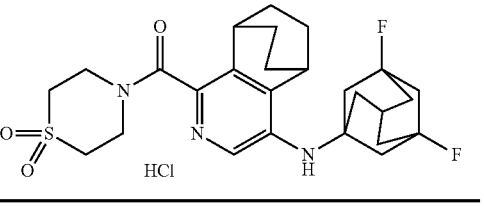 |

TABLE 81
| Ex | Str |
|---|---|
| 129 |  HCl |
| 130 | 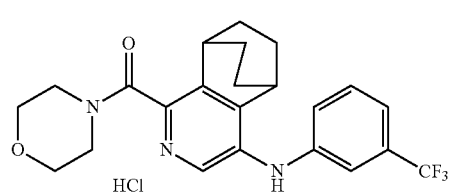 [SMILES: O=C(c1ncc(Nc2cccc(C(F)(F)F)c2)c2c1C1CCC2CC1)N1CCOCC1 ; Cl] HCl |
| 131 |  HCl |
| 132-1 | 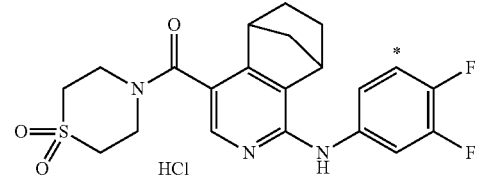 [SMILES: O=C(c1cnc(Nc2ccc(F)c(F)c2)c2c1C1CCC2C1)N1CCS(=O)(=O)CC1 ; Cl] HCl |
| 132-2 | 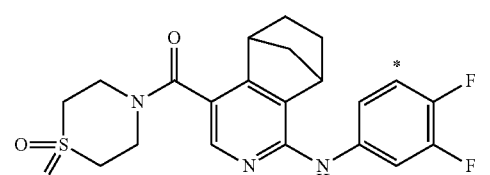 HCl |
| 133-1 | 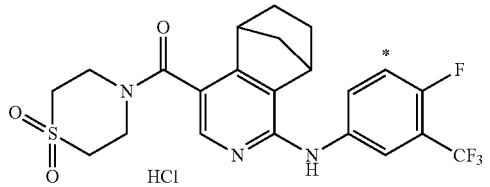 [SMILES: O=C(c1cnc(Nc2ccc(F)c(C(F)(F)F)c2)c2c1C1CCC2C1)N1CCS(=O)(=O)CC1 ; Cl] HCl |
| 133-2 | 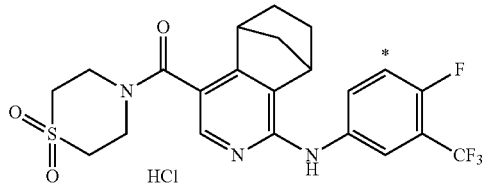 [SMILES: O=C(c1cnc(Nc2ccc(F)c(C(F)(F)F)c2)c2c1C1CCC2C1)N1CCS(=O)(=O)CC1 ; Cl] HCl |
TABLE 82
| Ex | Str |
|---|---|
| 134 | 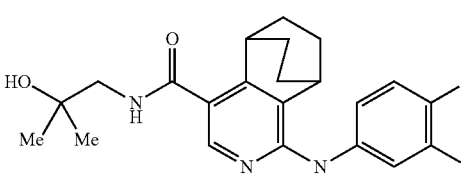 HCl |
| 135-1 | 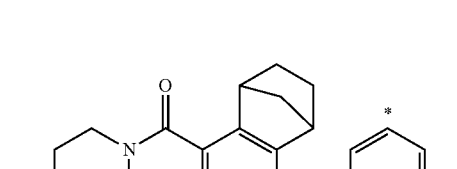 HCl |
| 135-2 | 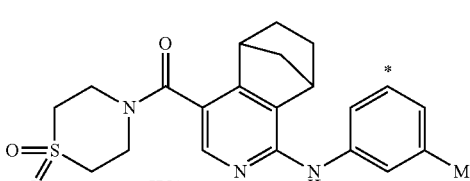 HCl |
| 136-1 | 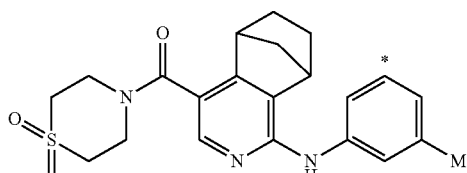 HCl |
| 136-2 | 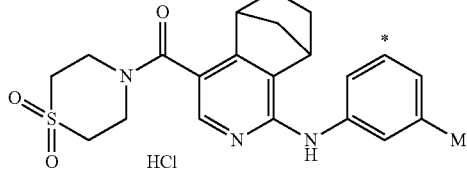 HCl |
| 137 | 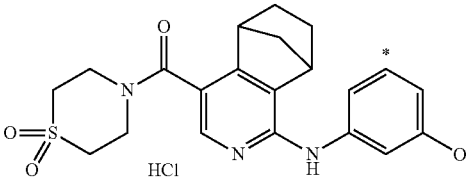 [SMILES: O=C(c1cnc(Nc2cccc(F)c2)c2c1C1CCC2C1)N1CCS(=O)(=O)CC1 ; Cl] HCl |
| 138 | 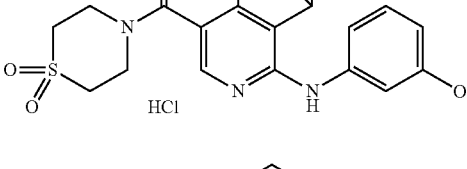 HCl |

TABLE 83
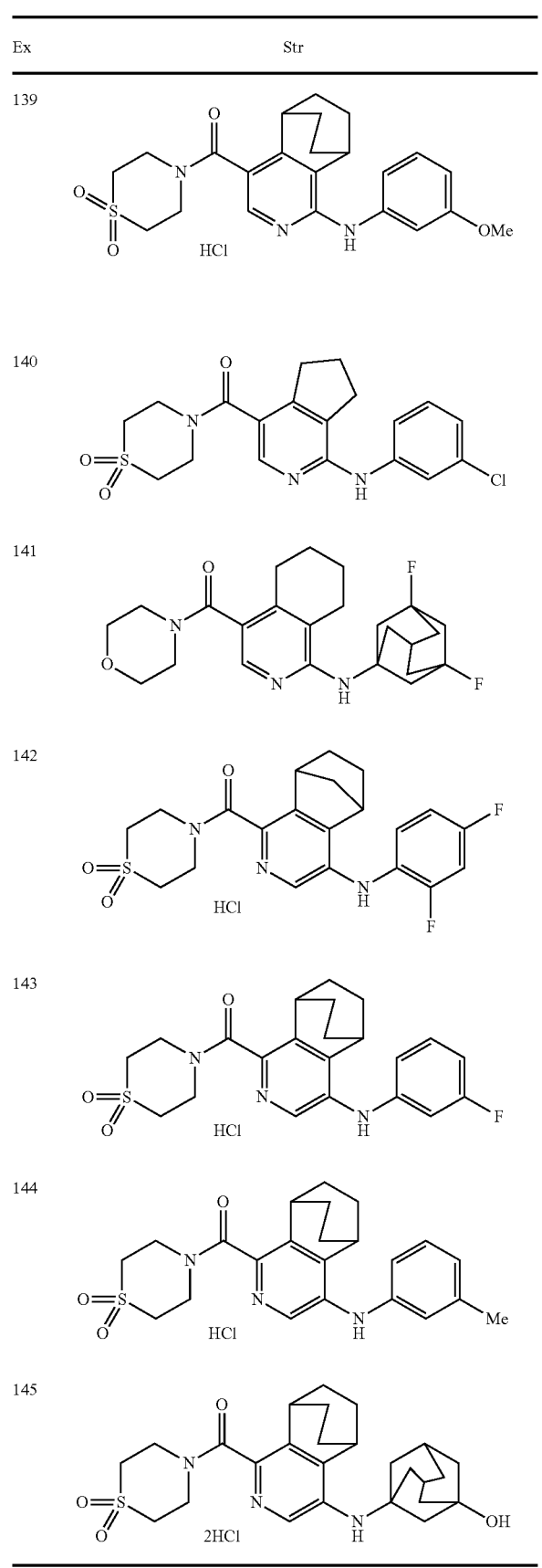
TABLE 84
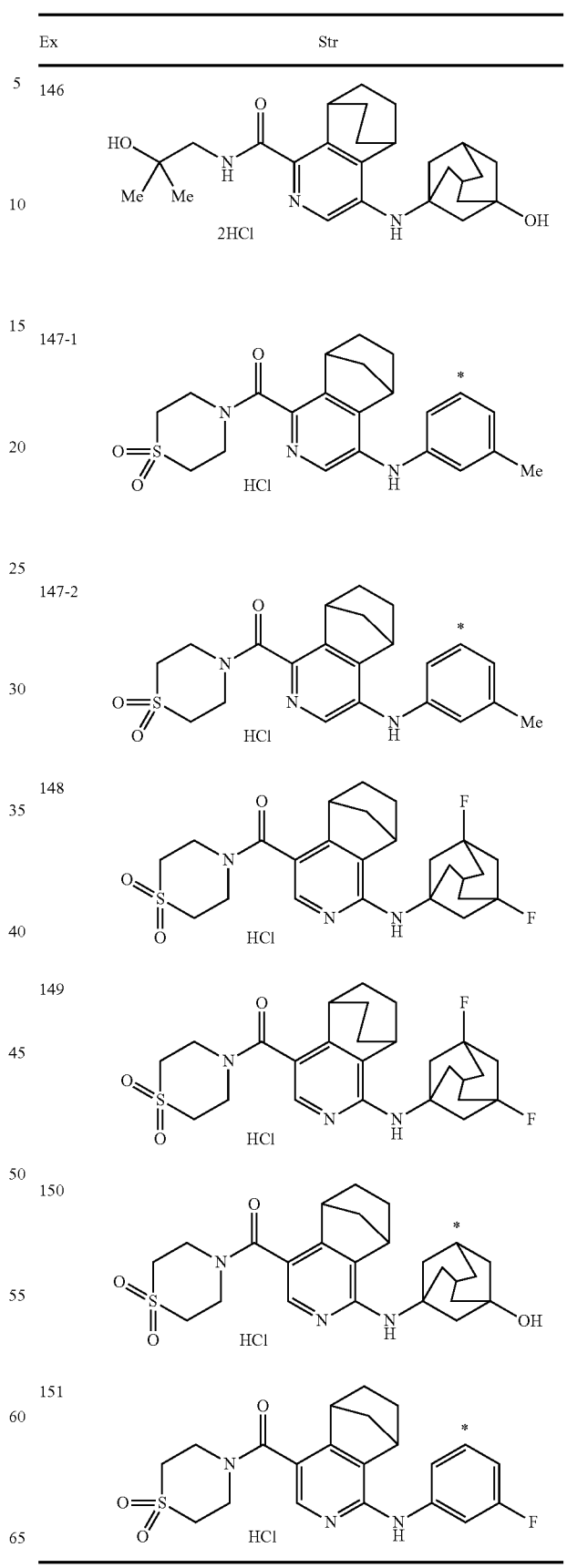

TABLE 85

| Ex | Str |
|---|---|
| 152-1 | (structure: thiomorpholine-1,1-dioxide-carbonyl-pyridine fused with bicyclic, NH-(3-fluorophenyl)*, HCl) |
| 152-2 | (structure: thiomorpholine-1,1-dioxide-carbonyl-pyridine fused with bicyclic, NH-(3-fluorophenyl)*, HCl) |
| 153-1 | (structure: thiomorpholine-1,1-dioxide-carbonyl-pyridine fused with bicyclic, NH-(3-methoxyphenyl)*, HCl) |
| 153-2 | (structure: thiomorpholine-1,1-dioxide-carbonyl-pyridine fused with bicyclic, NH-(3-methoxyphenyl)*, HCl) |
| 154 | (structure: thiomorpholine-1,1-dioxide-carbonyl-pyridine fused with bicyclic, NH-(4-fluoro-3-chlorophenyl), HCl) |
| 155 | (structure: thiomorpholine-1,1-dioxide-carbonyl-pyridine fused with tetrahydro ring, NH-(difluoroadamantyl)) |
| 156 | (structure: thiomorpholine-1,1-dioxide-carbonyl-pyridine fused with tetrahydro ring, NH-cyclooctyl) |

TABLE 86

| Ex | Str |
|---|---|
| 157 | (structure: thiomorpholine-1,1-dioxide-carbonyl-pyridine fused with bicyclic, NH-(3-methoxyphenyl), HCl) |
| 158-1 | (structure: thiomorpholine-1,1-dioxide-carbonyl-pyridine fused with bicyclic, NH-(hydroxyadamantyl)*, HCl) |
| 158-2 | (structure: thiomorpholine-1,1-dioxide-carbonyl-pyridine fused with bicyclic, NH-(hydroxyadamantyl)*, HCl) |
| 159 | (structure: thiomorpholine-1,1-dioxide-carbonyl-pyridine fused with bicyclic, NH-(4-fluoro-3-methoxyphenyl)*, HCl) |
| 160 | (structure: thiomorpholine-1,1-dioxide-carbonyl-pyridine fused with bicyclic, NH-(4-fluoro-3-methylphenyl)*) |
| 161 | (structure: thiomorpholine-1,1-dioxide-carbonyl-pyridine fused with bicyclic, NH-(4-fluoro-3-methylphenyl)*, HCl) |
| 162 | (structure: thiomorpholine-1,1-dioxide-carbonyl-pyridine fused with bicyclic, NH-(4-fluoro-3-methoxyphenyl)*, HCl) |

TABLE 87
| Ex | Str |
|---|---|
| 163-1 | |
| 163-2 | |
| 164 | |
| 165 | |
| 166 | |
| 167 | |
| 168 | |
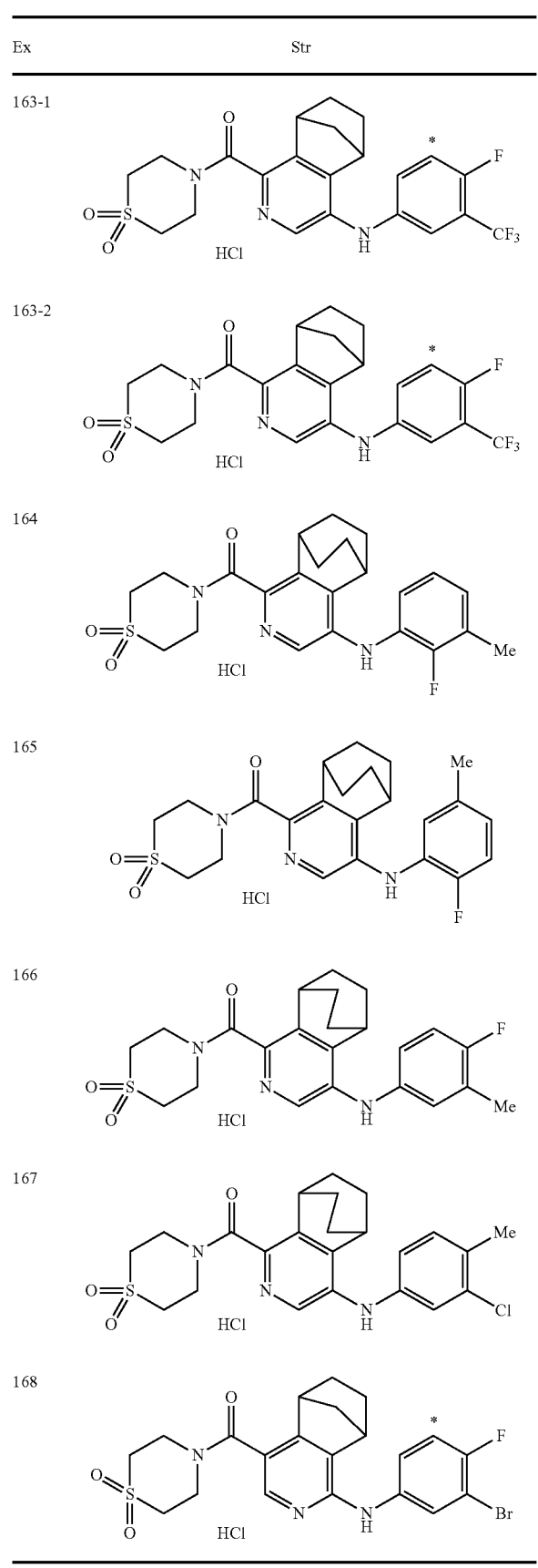
TABLE 88
| Ex | Str |
|---|---|
| 169 | |
| 170 | |
| 171 | |
| 172 | |
| 173 | |
| 174 | |
| 175 | |
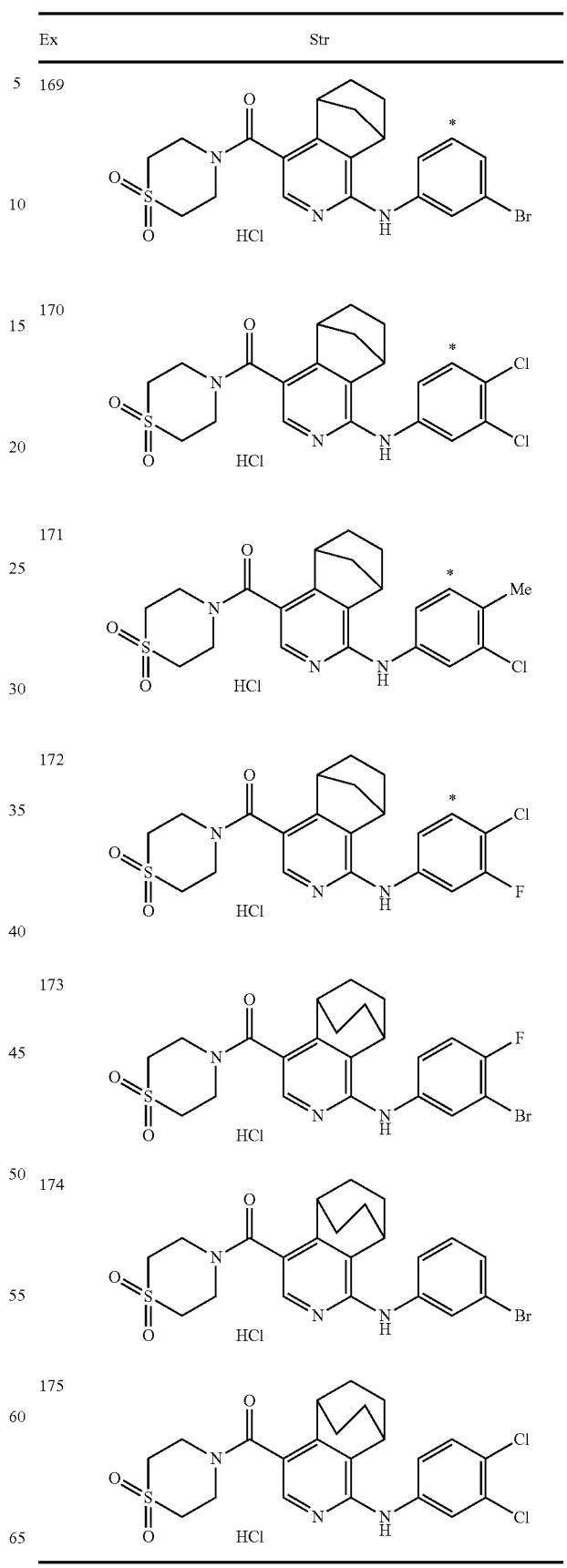

TABLE 89

| Ex | Str |
|---|---|
| 176 | 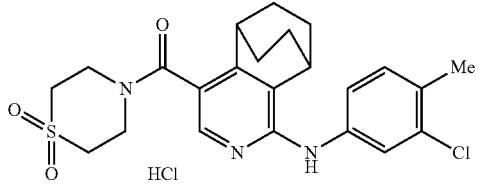 [SMILES: Cc1ccc(Nc2ncc(C(=O)N3CCS(=O)(=O)CC3)c3c2C2CCC3CC2)cc1Cl ; Cl] |
| 177 |  |
| 178 | 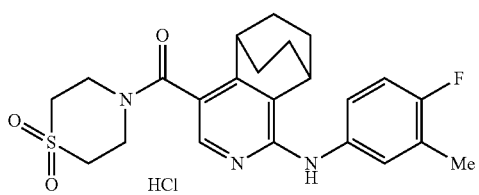 [SMILES: Cc1cc(Nc2ncc(C(=O)N3CCS(=O)(=O)CC3)c3c2C2CCC3CC2)ccc1F ; Cl] |

TABLE 89-continued

| Ex | Str |
|---|---|
| 179 | 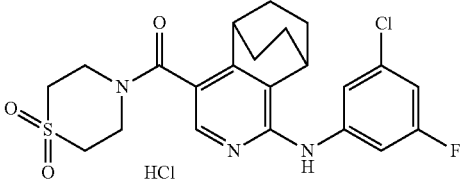 [SMILES: O=C(c1cnc(Nc2cc(F)cc(Cl)c2)c2c1C1CCC2CC1)N1CCS(=O)(=O)CC1 ; Cl] |
| 180 | 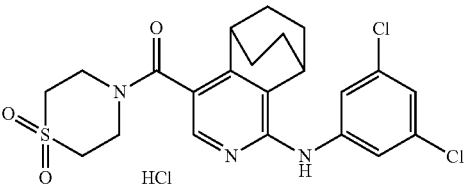 [SMILES: O=C(c1cnc(Nc2cc(Cl)cc(Cl)c2)c2c1C1CCC2CC1)N1CCS(=O)(=O)CC1 ; Cl] |

TABLE 90

| Ex | Syn | Data |
|---|---|---|
| 1 | 1 | NMR1: 1.63-1.86(4H, m), 2.38-2.72(4H, m), 3.12-3.38(2H, m), 3.40-3.70(6H, m), 6.95(1H, ddd, J = 0.7, 1.9, 8.6 Hz), 7.26(1H, t, J = 7.9 Hz), 7.6-7.66(1H, m), 7.83(1H, s), 7.88(1H, t, J = 1.9 Hz), 8.04(1H, s); ESI+: 372 |
| 2 | 2 | NMR1: 1.7-1.81(4H, m), 2.59-2.65(2H, m), 2.98-3.05(2H, m), 3.42-3.49(4H, m), 3.61-3.7(4H, m), 6.98(1H, dd, J = 2, 7.9 Hz), 7.07(1H, dd, J = 2.1, 8.2 Hz), 7.13(1H, t, J = 2 Hz), 7.3(1H, dd, J = 7.9, 8.2 Hz), 7.94(1H, s), 8.19(1H, s); ESI+: 408 |
| 3 | 3 | NMR1: 1.61-1.73(4H, m), 1.87-2.14(4H, m), 2.59-2.69(2H, m), 2.81-2.89(2H, m), 3.21-3.24(2H, m), 3.76-3.79(2H, m), 7.7(1H, dd, J = 7.7, 8 Hz), 7.85(1H, dd, J = 1.9, 8 Hz), 7.96(1H, dd, J = 1.9, 7.7 Hz), 8.04(1H, t, J = 1.9 Hz), 9.02(1H, s); ESI+: 455 |
| 4 | 4 | NMR1: 1.44-1.90(18H, m), 2.38-2.56(2H, m), 3.22-3.79(10H, m), 4.00-4.11(1H, m), 7.22-7.62(1H, m), 7.71(1H, s); ESI+: 372 |
| 5-1 | 5 | NMR1: 1.10-1.21(2H, m), 1.55(1H, d, J = 9.0 Hz), 1.70(1H, d, J = 9.0 Hz), 1.90-2.01(2H, m), 3.18-3.35(4H, m), 3.58-3.64(2H, m), 3.78-4.14(4H, m), 7.09-7.15(1H, m), 7.29(1H, dd, J = 6.4, 2.8 Hz), 7.35(1H, t, J = 9.0 Hz), 8.18(1H, s), 8.55(1H, brs); ESI+: 450, 452; [α]D: −91.25(c = 0.320, MeOH) |
| 5-2 | 5 | NMR1: 1.09-1.22(2H, m), 1.55(1H, d, J = 9.0 Hz), 1.69(1H, d, 9.0 Hz), 1.89-2.00(2H, m), 3.18-3.35 (4H, m), 3.58-3.64(2H, m), 3.72-4.74(4H, m), 7.07-7.14(1H, m), 7.28(1H, dd, J = 2.7, 6.5 Hz), 7.34(1H, t, J = 9.1 Hz), 8.17(1H, s), 8.52(1H, brs); ESI+: 450/452; [α]D: +116.73(c = 0.245, MeOH) |
| 6 | 6 | NMR1: 1.2-1.35(5H, m), 1.75-1.88(5H, m), 3.01-3.06(1H, m), 3.50-3.55(2H, m), 3.60-3.65(1H, m), 3.65- 3.75(4H, m), 7.00(1H, dd, J = 8.0, 2.0 Hz), 7.33(1H, dd, J = 8.0, 8.0 Hz), 7.70(1H, dd, J = 8.0, 2.0 Hz), 8.05(1H, d, J = 2.0 Hz), 8.78(1H, s); ESI+: 399 |
| 7-1 | 7 | NMR1: 1.08-1.21(2H, m), 1.53(1H, d, J = 9 Hz), 1.68(1H, d, J = 9 Hz), 1.89-1.95(2H, m), 3.2-3.3(4H, m), 3.57-3.62(2H, m), 3.70-4.20(4H, m), 6.89-6.93(1H, m), 7.11(1H, ddd, J = 2.7, 7, 12.7 Hz), 7.3-7.37(1H, m), 8.18(1H, s), 8.43(1H, brs); ESI+: 434; [α]D: −102.4(c = 0.275, MeOH) |
| 7-2 | 7 | NMR1: 1.08-1.21(2H, m), 1.54(1H, d, J = 9 Hz), 1.69(1 H, d, 9 Hz), 1.89-2.00(2H, m), 3.2-3.3(4H, m), 3.61(2H, s), 3.75-4.14(4H, m), 6.89-6.95(1H, m), 7.13(1H, ddd, 2.7, 7, 12.7 Hz), 7.3-7.39(1H, m), 8.19(1H, s), 8.48(1H, brs); ESI+: 434; [a]D: +103.2(c = 0.310, MeOH) |
| 8 | 8 | NMR1: 1.45-1.54(1H, m), 1.56-1.63(2H, m), 1.64-1.75(5H, m), 1.76-1.84(2H, ), 1.96-2.13(8H, m), 2.25(2H, brs), 2.42-2.51(1H, m), 2.55-2.66(1H, m), 3.58-3.84(8H, m), 7.93(1H, s); ESI+: 460 |
| 9 | 9 | NMR1: 1.63-1.85(10H, m), 1.97-2.19(6H, m), 2.38-2.51(3H, m), 2.74-2.81(2H, m), 2.83-2.9(4H, m), 3.01-3.08(4H, m), 3.59(2H, s), 4.05(1H, s), 7.99(1H, s); ESI+: 466 |

TABLE 91

| Ex | Syn | Data |
|---|---|---|
| 10 | 1 | NMR1: 1.67-1.79(4H, m), 2.56-2.62(2H, m), 2.65-2.72(2H, m), 3.1-3.18(2H, m), 3.22-3.3(2H, m), 3.56-3.64(2H, m), 4.03-4.1(2H, m), 6.84-6.9(2H, m), 6.95(1H, t, J = 2.1 Hz), 7.22(1H, t, J = 8.1 Hz), 7.8(1H, s), 8.2(1H, s); ESI+: 420; Temp: 129.5 |
| 11 | 4 | NMR1: 1.02-1.20(4H, m), 1.36-1.84(10H, m), 2.24-2.36(2H, m), 2.38-2.52(2H, m), 3.23-3.78(8H, m), 6.80-7.40(1H, brs), 7.74(1H, s), 12.70-13.50(1H, brs); ESI+: 356 |
| 12 | 1 | NMR1: 1.02-1.84(14H, m), 2.8-2.44(4H, m), 3.04-3.30(4H, m), 3.62-3.88(4H, m), 7.84(1H, s); ESI+: 404 |
| 13 | 4 | NMR1: 1.38-1.46(2H, m), 1.55-1.90(12H, m), 2.20-2.30(2H, m), 2.36-2.44(2H, m), 3.20-3.80(10H, m), 4.10-4.22(1H, m), 7.08-7.40(1H, brs), 7.72(1H, s), 13.22-13.62(1H, brs); ESI+: 370 |
| 14 | 1 | NMR1: 1.34-1.84(16H, m), 2.16-2.32(4H, m), 3.06-3.24(4H, m), 3.48-4.18(4H, m), 4.25-4.40(1H, m), 5.48(1H, d, J = 7.7 Hz), 7.80(1H, s); ESI+: 418 |
| 15 | 1 | NMR1: 1.00-1.70(8H, m), 1.90-2.26(4H, m), 2.57-2.92(4H, m), 3.13-3.25(4H, m), 3.73-3.95(4H, m), 5.85(1H, brs), 7.88-8.00(1H, m); ESI+: 390 |
| 16 | 1 | NMR1: 1.70-1.79(2H, m), 1.81-1.91(2H, m), 2.61-2.72(2H, m), 3.20-3.34(2H, brm), 3.46-3.76(8H, brm), 6.86-6.93(1H, m), 7.35-7.42(1H, m), 7.72-7.78(1H, m), 7.85(1H, brs), 7.87(1H, s), 8.18(1H, s); ESI+: 422; Temp: 168.1 |
| 17 | 1 | NMR1: 1.69-1.79(2H, m), 1.80-1.91(2H, m), 2.60-2.71(2H, m), 3.00-3.35(6H, brm), 3.72(4H, brs), 6.88-6.94(1H, m), 7.36-7.43(1H, m), 7.71-7.77(1H, m), 7.88(1H, brs), 8.04(1H, s), 8.21(1H, s); ESI+: 470.3 |
| 18 | 1 | NMR1: 1.6-1.68(2H, m), 1.71-1.88(8H, m), 2-2.23(6H, m), 2.41-2.45(3H, m), 2.57-2.65(2H, m), 3.12-3.25(4H, m), 3.56-3.64(2H, m), 4-4.07(2H, m), 4.34(1H, s), 8.08(1H, s); ESI+: 480 |
| 19 | 4 | NMR1: 1.66-1.73(2H, m), 1.75-1.84(8H, m), 2.01-2.26(6H, m), 2.43-2.52(1H, m), 2.55-2.62(4H, m), 3.13-3.2(2H, m), 3.5-3.56(2H, m), 3.61-3.71(4H, m), 6.55(1H, s), 8.16(1H, s);ESI+: 432 |
| 20 | 1 | 1HNMR: 1.57-1.67(2H, m), 1.69-1.87(8H, m), 2-2.23(6H, m), 2.43-2.53(1H, m), 2.62-2.83(2H, m), 3.71(1H, dd, J = 4.3, 10.4 Hz), 3.86(1H, dd, J = 4.3, 9.6 Hz), 4.17(1H, dd, J = 6.8, 10.4 Hz), 4.22(1H, dd, J = 6.8, 9.6 Hz), 4.33(1H, brs), 4.4-4.48(1H, m), 5.66(1H, d, J = 6.2 Hz), 8.04(1H, s); ESI+: 418 |
| 21 | 1 | NMR1: 1.05-1.17(2H, m), 1.21-1.29(2H, m), 1.4-1.57(4H, m), 1.6-1.81(5H, m), 2.19-2.26(2H, m), 2.31-2.59(5H, m), 3.09-3.18(2H, m), 3.43-3.51(2H, m), 3.55-3.68(4H, m), 4.61(1H, d, J = 5.7 Hz), 7.59(1H, s); ESI+: 356 |

TABLE 92

| Ex | Syn | Data |
|---|---|---|
| 22 | 1 | NMR1: 1.05-1.3(3H, m), 1.4-1.57(4H, m), 1.6-1.81(5H, m), 2.19-2.27(2H, m), 2.31-2.5(3H, m), 2.55-2.64(2H, m), 3.08-3.17(2H, m), 3.18-3.25(2H, m), 3.55-3.64(2H, m), 3.97-4.08(2H, m), 4.7(1H, d, J = 5.7 Hz), 7.61(1H, s); ESI+: 404 |
| 23 | 1 | NMR1: 1.69-1.79(4H, m), 1.88-2.12(4H, m), 2.56-2.69(4H, m), 3.24-3.32(2H, m), 3.73-3.8(2H, m), 7.28(1H, t, J = 2.2 Hz), 8.02(1H, d, J = 2.2 Hz), 8.04(1H, s), 8.18(1H, d, J = 2.2 Hz), 8.24(1H, s); ESI+: 407 |
| 24 | 1 | NMR1: 1.68-1.78(2H, m), 1.81-1.91(2H, m), 2.58-2.69(2H, m), 3.20-3.33(2H, brm), 3.48-3.77(8H, brm), 7.31-7.37(1H, m), 7.67(1H, ddd, J = 2.7, 4.3, 9.0 Hz), 7.85(1H, s), 8.02(1H, dd, J = 2.7, 6.9 Hz), 8.07(1H, s); ESI+: 390 |
| 25 | 1 | NMR1: 1.68-1.78(2H, m), 1.80-1.91(2H, m), 2.57-2.70(2H, m), 3.00-3.38(6H, brm), 3.72(4H, brs), 7-31-7.38(1H, m), 7.68(1H, ddd, J = 2.7, 4.3, 9.0 Hz), 8.01(1H, s), 8.03(1H, dd, J = 2.7, 6.9 Hz), 8.10(1H, s); ESI+: 438 |
| 26 | 1 | NMR1: 1.68-1.80(2H, m), 1.81-1.93(2H, m), 2.59-2.77(2H, m), 3.16-3.35(2H, brm), 3.48-3.79(8H, brm), 7.39-7.47(1H, m), 7.85(1H, s), 8.06-8.18(2H, m), 8.24(1H, s); ESI+: 424 |
| 27 | 4 | NMR1: 1.09-1.32(4H, m), 1.42-1.59(5H, m), 1.61-1.82(6H, m), 2.22-2.28(2H, m), 2.96-3.02(2H, m), 3.03(3H, s), 3.32-3.4(2H, m), 3.62-3.7(2H, m), 6.55(1H, s), 7.65(1H, s), 8.71(1H, brs); ESI+: 392 |
| 28 | 1 | NMR1: 3.18-3.28(4H, m), 3.80-4.00(4H, m), 4.19-4.32(4H, m), 6.99-7.04(1H, m), 7.31(1H, t, J = 8 Hz), 7.66(1H, d, J = 8 Hz), 7.93-7.97(1H, m), 8.18(1H, s), 8.53(1H, s); ESI+: 424/426 |

TABLE 92-continued

| Ex | Syn | Data |
|---|---|---|
| 29 | 1 | NMR1: 1.68-1.78(2H, m), 1.80-1.91(2H, m), 2.58-2.72(2H, m), 3.00-4.53(10H, brm), 7.40-7.49(1H, m), 8.02(1H, s), 8.06-8.13(1H, m), 8.18(1H, dd, J = 2.7, 6.0 Hz), 8.27(1H, s); ESI+: 472 |
| 30 | 1 | NMR1: 1.63-1.90(4H, m), 2.46-2.70(4H, m), 3.02-3.36(4H, m), 3.54-3.90(3H, m), 4.18-4.45(1H, m), 6.93-6.98(1H, m), 7.27(1H, t, J = 8.1 Hz), 7.62-7.65(1H, m), 7.90(1H, t, J = 2.0 Hz), 8.00(1H, s), 8.07(1H, s); ESI+: 420; Temp: 250.5 |
| 31 | 2 | NMR1: 1.71-1.81(4H, m), 2.61-2.67(2H, m), 2.99-3.06(2H, m), 3.42-3.49(4H, m), 3.63-3.69(4H, m), 7.26(1H, d, J = 7.9 Hz), 7.35-7.41(2H, m), 7.5(1H, dd, J = 7.9, 8.2 Hz), 8.1(1H, s), 8.22(1H, s); ESI+: 442 |
| 32 | 1 | NMR1: 1.68-1.78(4H, m), 2.57-2.71(4H, m), 3.12-3.19(2H, m), 3.48-3.55(2H, m), 3.66(4H, brs), 7.24(1H, dd, J = 2.3, 8.2 Hz), 7.41(1H, brs), 7.5(1H, d, J = 7.8 Hz), 7.61(1H, dd, J = 7.8, 8.2 Hz), 8.05(1H, s); ESI+: 407 |
| 33 | 1 | NMR1: 1.67-1.79(4H, m), 2.59-2.77(4H, m), 3.09-3.18(2H, m), 3.25-3.32(2H, m), 3.56-3.65(2H, m), 4.03-4.13(2H, m), 7.28(1H, d, J = 8.2 Hz), 7.43(1H, brs), 7.52(1H, d, J = 7.8 Hz), 7.62(1H, dd, J = 7.8, 8.2 Hz), 8.04(1H, s); ESI+: 455 |

TABLE 93

| Ex | Syn | Data |
|---|---|---|
| 34 | 1 | NMR1: 1.67-1.78(4H, m), 1.88-2.12(4H, m), 2.61-2.75(4H, m), 3.2-3.27(2H, m), 3.73-3.8(2H, m), 7.17-7.19(1H, m), 7.36-7.4(3H, m), 8.24(1H, s); ESI+: 423 |
| 35 | 1 | NMR1: 1.90-2.15(2H, m), 2.75-2.92(4H, m), 3.38-3.65(8H, m), 6.95(1H, dd, J = 10, 2 Hz), 7.28(1H, t, J = 10 Hz), 7.70(1H, dd, J = 10, 2 Hz), 7.98(1H, s), 8.00(1H, t, J = 2 Hz), 8.43(1H, s); ESI+: 358/360 |
| 36 | 1 | NMR1: 1.68-1.79(4H, m), 2.59-2.61(2H, m), 2.67-2.7(2H, m), 3.11-3.17(2H, m), 3.23-3.28(2H, m), 3.59-3.62(2H, m), 4.05-4.08(2H, m), 7.13(1H, d, J = 7.7 Hz), 7.19(1H, d, J = 8.2 Hz), 7.24(1H, brs), 7.43(1H, dd, J = 7.7, 8.2 Hz), 7.98(1H, s), 8.23(1H, s); ESI+: 454; Temp: 183.2 |
| 37 | 1 | NMR1: 1.67-1.79(4H, m), 2.56-2.62(2H, m), 2.65-2.71(2H, m), 3.11-3.17(2H, m), 3.23-3.29(2H, m), 3.59-3.62(2H, m), 4.05-4.08(2H, m), 6.76(1H, d, J = 8.2 Hz), 6.86(1H, brs), 6.94(1H, dd, J = 1.7, 8.2 Hz), 7.32(1H, t, J = 8.2 Hz), 7.93(1H, s), 8.23(1H, s); ESI+: 470 |
| 38 | 4 | NMR1: 0.99(3H, s), 1.04(3H, s), 1.07-1.24(2H, m), 1.33-1.42(1H, m), 1.49-1.63(3H, m), 1.64-1.76(3H, m), 1.77-1.86(2H, m), 1.92-2.04(1H, m), 2.32-2.46(1H, m), 2.44-2.58(1H, m), 2.54-2.68(2H, m), 3.02-3.38(4H, brm), 3.59-3.84(4H, brm), 4.20-4.33(1H, m), 7.39(1H, brs), 8.00(1H, brs); ESI+: 420 |
| 39 | 1 | NMR1: 1-1.16(2H, m), 1.51(1H, d, J = 8.8 Hz), 1.65(1H, d, J = 8.9 Hz), 1.86-1.96(2H, m), 3.38-3.68(9H, m), 3.84(1H, brs), 6.9-6.94(1H, m), 7.26(1H, t, J = 8.1 Hz), 7.66-7.71(1H, m), 7.97(1H, s), 7.99(1H, t, J = 2.1 Hz), 8.68(1H, s); ESI+: 384 |
| 40 | 1 | NMR1: 1.01-1.17(2H, m), 1.51(1H, d, J = 8.9 Hz), 1.66(1H, d, J = 8.9 Hz), 1.85-2(2H, m), 3.23(4H, brs), 3.47(1H, brs), 3.84(1H, brs), 3.9(4H, brs), 6.89-6.96(1H, m), 7.27(1H, t, J = 8.1 Hz), 7.63-7.72(1H, m), 8.01(1H, t, J = 2 Hz), 8.09(1H, s), 8.71(1H, s); 1H, ESI+: 432 |
| 41 | 4 | NMR1: 1.22-1.38(4H, m), 1.72-1.88(4H, m), 3.18(3H, brs), 3.34(2H, brs), 3.42(1H, brs), 3.71(2H, brs), 3.81(3H, s), 4.08(2H, brs), 6.62(1H, dd, J = 8.8, 2.4 Hz), 6.84(1H, d, J = 2.4 Hz), 7.26(1H, d, J = 8.8 Hz), 8.36(1H, s), 8.41(1H, brs); ESI+: 476/478 |
| 42 | 1 | NMR1: 1.02-1.1(2H, m), 1.12(6H, s), 1.49(1H, d, J = 8.9 Hz), 1.61(1H, d, J = 8.9 Hz), 1.9-1.96(2H, m), 3.2-3.25(2H, m), 3.83(1H, brs), 3.92(1H, brs), 4.54(1H, s), 6.9-6.95(1H, m), 7.27(1H, t, J = 8.1 Hz), 7.64-7.68(1H, m), 7.97(1H, t, J = 6.1 Hz), 8.06(1H, t, J = 2 Hz), 8.34(1H, s), 8.71(1H, s); ESI+: 386 |
| 43 | 1 | NMR1: 1.63-1.72(2H, m), 1.74-1.84(2H, m), 2.07-2.17(3H, m), 2.20-2.31(3H, m), 2.35-2.46(8H, m), 3.24(4H, brs), 3.76(4H, brs), 5.36(1H, s), 7.90(1H, s); ESI+: 498 |

TABLE 94

| Ex | Syn | Data |
|---|---|---|
| 44 | 4 | NMR1: 0.75-0.90(2H, m), 0.90(1.5H, s), 0.91(1.5H, s), 0.99(3H, s), 1.04(3H, s), 1.35-1.43(1H, m), 1.48-1.59(2H, m), 1.66-1.75(2H, m), 1.75-1.85(2H, m), 1.86-1.99(2H, m), 2.33-2.46(1H, m), 2.45-2.54(1H, m), 2.55-266(2H, m), 3.03-3.34(4H, brm), 3.60-3.84(4H, brm), 4.25-4.38(2H, m), 7.42(1H, brs), 7.99(1H, s); ESI+: 434 |
| 45 | 4 | NMR1: 0.76-0.89(2H, m), 0.90(1.5H, s), 0.91(1.5H, s), 0.99(3H, s), 1.03(3H, s), 1.35-1.44(1H, m), 1.48-1.61(2H, m), 1.67-1.76(2H, m), 1.76-2.00(4H, m), 2.35-2.46(1H, m), 2.45-2.56(1H, m), 2.59-2.78(2H, m), 3.24-3.78(8H, m), 4.18-4.32(1H, m), 7.39(1H, brs), 7.74(1H, s); ESI+: 386 |
| 46 | 4 | NMR1: 0.99(3H, s), 1.04(3H, s), 1.08-1.24(2H, m), 1.15(6H, s), 1.34-1.42(1H, m), 1.52-1.63(3H, m), 1.65-1.76(3H, m), 1.76- |

TABLE 94-continued

| Ex | Syn | Data |
|---|---|---|
| | | 1.84(2H, m), 1.90-1.99(1H, m), 2.35-2.46(1H, m), 2.45-2.54(1H, m), 2.77-2.83(2H, m), 3.22(2H, d, J = 6.0 Hz), 4.18-4.30(1H, m), 7.44(1H, brs), 7.80(1H, s), 8.46(1H, brs); ESI+: 374 |
| 47 | 4 | NMR1: 0.99(3H, s), 1.03(3H, s), 1.06-1.24(2H, m), 1.34-1.43(1H, m), 1.51-1.63(1H, m), 1.63-1.77(3H, m), 1.77-1.87(2H, m), 1.93-2.02(1H, m), 2.34-2.46(1H, m), 2.45-2.55(1H, m), 2.59-2.79(2H, m), 3.33(4H, brs), 3.66(4H, brs), 4.12-4.25(1H, m), 7.41(1H, brs), 7.75(1H, s); ESI+: 372 |
| 48 | 4 | NMR1: 0.99(3H, s), 1.04(3H, s), 1.08-1.25(2H, m), 1.30(6H, s), 1.34-1.42(1H, m), 1.51-1.63(3H, m), 1.65-1.85(5H, m), 1.90-1.99(1H, m), 2.34-2.45(1H, m), 2.44-2.54(1H, m), 2.73-2.81(2H, m), 3.48(2H, brs), 4.19-4.32(1H, m), 7.40(1H, brs), 7.72(1H, s), 7.94(1H, brs); ESI+: 374 |
| 49 | 1 | NMR1: 1.06-1.18(2H, m), 1.51(1H, d, J = 9 Hz), 1.66(1H, d, J = 9 Hz), 1.85-1.97(2H, m), 3.36-3.57(6H, m), 3.65(4H, brs), 6.87(1H, dd, J = 1.6, 7.9 Hz), 6.94-6.99(2H, m), 7.24(1H, dd, J = 7.9, 8.1 Hz), 8.17(1H, s), 8.32(1H, brs); ESI+: 384 |
| 50 | 1 | NMR1: 1.06-1.21(2H, m), 1.51(1H, d, J = 9 Hz), 1.66(1H, d, J = 9 Hz), 1.85-1.99(2H, m), 3.18-3.29(4H, m), 3.51(1H, brs), 3.6(1H, brs), 3.82-4.14(4H, m), 6.9(1H, dd, J = 1.5, 7.8 Hz), 6.98-7.03(2H, m), 7.26(1H, dd, J = 7.8, 8.1 Hz), 8.18(1H, s), 8.38(1H, brs); ESI+: 432 |
| 51 | 1 | NMR1: 0.967(3H, s), 0.974(1.5H, s), 0.98(1.5H, s), 1.01-1.27(6H, m), 1.32-1.47(2H, m), 1.48-1.68(4H, m), 1.81-1.90(1H, m), 1.91-2.04(1H, m), 3.19-3.29(4H, m), 3.43(1H, s), 3.62(1H, s), 3.84-4.01(4H, m), 4.03-4.16(1H, m), 6.14(1H, t, J = 8.6 Hz), 7.91(1H, s); ESI+: 432 |
| 52 | 1 | NMR1: 1.73-1.90(4H, m), 2.61-2.75(2H, m), 2.75-2.84(2H, m), 3.02-3.37(4H, brm), 3.50-3.86(4H, brm), 4.37(1H, brs), 7.49-7.54(1H, m), 7.58(1H, m), 7.60-7.65(1H, m), 7.67-7.73(1H, m), 7.95(1H, s); ESI+: 455; Temp: 181.9 |

TABLE 95

| Ex | Syn | Data |
|---|---|---|
| 53 | 1 | NMR1: 1.66-1.79(3H, m), 1.81-1.93(3H, m), 2.53-2.69(4H, m), 3.35-3.43(2H, m), 3.56-3.63(1H, m), 3.64-3.82(5H, m), 7.40-7.47(1H, m), 7.85(1H, s), 8.08-8.16(2H, m), 8.23(1H, s); ESI+: 438 |
| 54 | 4 | NMR1: 1.1-1.19(2H, m), 1.57(1H, d, J = 9 Hz), 1.73(1H, d, J = 9 Hz), 1.92-2.01(2H, m), 3.35-3.74(10H, m), 6.87(1H, d, J = 8.2 Hz), 7.02(1H, brs), 7.12(1H, dd, J = 1.6, 8.2 Hz), 7.39(1H, t, J = 8.2 Hz), 8.26(1H, s), 8.72(1H, s); ESI+: 434 |
| 55 | 1 | NMR1: 1.05-1.22(2H, m), 1.51(1H, d, J = 9 Hz), 1.67(1H, d, J = 9 Hz), 1.85-1.99(2H, m), 3.19-3.3(4H, m), 3.51(1H, brs), 3.6(1H, brs), 3.83-4.13(4H, m), 6.81(1H, d, J = 8.2 Hz), 6.92(1H, brs), 7.05(1H, dd, J = 1.6, 8.2 Hz), 7.35(1H, t, J = 8.2 Hz), 8.2(1H, s), 8.49(1H, s); ESI+: 482 |
| 56 | 4 | NMR1: 1.07-1.13(8H, m), 1.53(1H, d, J = 9 Hz), 1.65(1H, d, J = 9 Hz), 1.88-2(2H, m), 3.2-3.3(2H, m), 3.55(1H, brs), 4.31-4.36(2H, m), 6.83(1H, d, J = 8.2 Hz), 6.96(1H, brs), 7.08(1H, dd, J = 1.5, 8.2 Hz), 7.36(1H, t, J = 8.2 Hz), 8.26(1H, s), 8.3(1H, t, J = 6 Hz), 8.6(1H, s); ESI+: 436 |
| 57 | 4 | NMR1: 1.12-1.18(2H, m), 1.57(1H, d, J = 9.1 Hz), 1.71(1H, d, J = 9.1 Hz), 1.93-1.99(2H, m), 3.36-3.71(10H, m), 7.39-7.45(3H, m), 8.22(1H, s), 8.69(1H, s); ESI+: 436 |
| 58 | 1 | NMR1: 1.06-1.21(2H, m), 1.51(1H, d, J = 9 Hz), 1.65(1H, d, J = 9 Hz), 1.86-1.99(2H, m), 3.18-3.29(4H, m), 3.49(1H, brs), 3.6(1H, brs), 3.84-4.12(4H, m), 7.31-7.43(3H, m), 8.16(1H, s), 8.45(1H, s); ESI+: 484 |
| 59 | 1 | NMR1: 1.06-1.21(2H, m), 1.50(1H, d, J = 9.0 Hz), 1.65(1H, d, J = 9.0 Hz), 1.87-1.96(2H, m), 3.18-3.30(4H, m), 3.50(1H, brs), 3.60(1H, brs), 3.83-4.14(4H, m), 7.02-7.07(1H, m), 7.18(1H, dd, J = 6.4, 2.8 Hz), 7.31(1H, t, J = 9.0 Hz), 8.13(1H, s), 8.28(1H, brs); ESI+: 450/452 |
| 60 | 1 | NMR1: 0.96(3H, s), 0.98(3H, s), 1.03-1.18(2H, m), 1.21-1.31(1H, m), 1.32-1.40(1H, m), 1.44-1.54(1H, m), 1.51-1.63(2H, m), 1.63-1.74(3H, m), 1.74-1.83(2H, m), 1.83-1.92(1H, m), 1.93-2.02(1H, m), 2.27-2.39(2H, m), 2.42-2.57(1H, m), 3.36-3.45(2H, m), 3.53-3.61(1H, m), 3.63-3.78(5H, m), 4.08-4.20(1H, m), 5.37(1H, d, J = 7.9 Hz), 7.68(1H, s); ESI+: 386 |
| 61 | 4 | NMR1: 1.05-1.28(2H, m), 1.58(1H, d, J = 8.9 Hz), 1.73(1H, d, J = 8.9 Hz), 1.92-2.04(2H, m), 3.29(4H, brs), 3.54(1H, s), 3.90 (1H, s), 3.94(4H, brs), 7.02(1H, d, J = 8.0 Hz), 7.47(1H, dd, J = 8.0, 8.2 Hz), 7.73(1H, d, J = 8.2 Hz), 7.87(1H, s), 8.12(1H, s), 9.42(1H, brs); ESI+: 482 |
| 62 | 4 | NMR1: 1.06-1.16(1H, m), 1.17-1.26(1H, m), 1.58(1H, d, J = 9.0 Hz), 1.73(1H, d, J = 9.0 Hz), 1.92-2.06(2H, m), 3.49(1H, s), 3.54(4H, brs), 3.65(4H, brs), 3.91(1H, s), 7.04(1H, d, J = 7.9 Hz), 7.48(1H, dd, J = 7.9, 8.1 Hz), 7.71(1H, d, J = 8.1 Hz), 7.81(1H, s), 7.99(1H, s), 9.54(1H, brs); ESI+: 434 |

TABLE 96

| Ex | Syn | Data |
|---|---|---|
| 63 | 1 | NMR1: 1.05-1.22(2H, m), 1.56(1H, d, J = 8.7 Hz), 1.70(1H, d, J = 8.7 Hz), 1.89-2.03(2H, m), 3.46(1H, s), 3.53(4H, brs), 3.64(4H, brs), 3.86(1H, s), 7.39-7.48(1H, m), 7.99(1H, s), 8.15-8.25(2H, m), 8.88(1H, s); ESI+: 436 |
| 64 | 1 | NMR1: 1.06-1.19(2H, m), 1.50(1H, d, J = 9.0 Hz), 1.65(1H, d, J = 9.0 Hz), 1.84-1.97(2H, m), 3.36-3.44(1H, m), 3.45-3.57(5H, m), 3.60-3.71(4H, m), 6.98-7.04(1H, m), 7.14(1H, dd, J = 6.6, 2.4 Hz), 7.29(1H, t, J = 9.0 Hz), 8.12(1H, s), 8.23(1H, brs); ESI+: 402 |
| 65 | 4 | NMR1: 1.06-1.16(1H, m), 1.16-1.25(1H, m), 1.58(1H, d, J = 8.9 Hz), 1.73 (1H, d, J = 8.9 Hz), 1.92-2.06(2H, m), 3.29(4H, brs), 3.54(1H, s), 3.90(1H, s), 3.94(4H, brs), 7.47-7.54(1H, m), 8.07-8.13(1H, m), 8.10(1H, s), 8.18(1H, dd, J = 2.6, 6.3 Hz), 9.53(1H, brs); ESI+: 484 |
| 66 | 4 | NMR1: 1.00(3H, s), 1.02(1.5H, s), 1.03(1.5H, s), 1.05-1.20(4H, m), 1.34-1.51(2H, m), 1.52-1.76(5H, m), 1.90-2.08(3H, m), 3.46(1H, s), 3.54(4H, m), 3.64(4H, m), 3.88(0.5H, s), 3.94(0.5H, s), 4.06-4.20(1H, m), 7.80(1H, s), 8.09(1H, brs); ESI+: 384 |
| 67 | 4 | NMR1: 1.00(3H, s), 1.02(1.5H, s), 1.03(1.5H, s), 1.05-1.19(4H, m), 1.33-1.81(8H, m), 1.86-2.08(4H, m), 3.48-3.84(9H, m), 3.88(0.5H, s), 3.94(0.5H, s), 4.03-4.18(1H, m), 7.80(1H, s), 8.10(1H, brs); ESI+: 398 |
| 68 | 4 | NMR: 1.08-1.17(1H, m), 1.15(6H, s), 1.16-1.24(1H, m), 1.57(1H, d, J = 9.0 Hz), 1.70(1H, d, J = 9.0 Hz), 1.92-2.07(2H, m), 3.26(1H, dd, J = 6.0, 13.1 Hz), 3.28(1H, dd, J = 6.1, 13.1 Hz), 3.89(1H, s), 4.01(1H, s), 7.52-7.61(1H, m), 7.96-8.04(1H, m), 8.14-8.22(1H, m), 8.30(1H, s), 8.36(1H, brs), 9.79(1H, brs); ESI+: 438 |
| 69 | 4 | NMR1: 1.09-1.23(2H, m), 1.34(6H, s), 1.57(1H, d, J = 8.9 Hz), 1.70(1H, d, J = 8.9 Hz), 1.92-2.09(2H, m), 3.52(2H, s), 3.88(1H, m), (1H, s), 3.94(1H, s), 7.52-7.60(1H, m), 7.73(1H, brs), 7.94-8.04(1H, m), 8.13-8.20(1H, m), 8.22(1H, s), 9.75(1H, brs); ESI+: 438 |
| 70 | 4 | NMR1: 1.07-1.17(1H, m), 1.18-1.26(1H, m), 1.58(1H, d, J = 9.0 Hz), 1.74(1H, d, J = 9.0 Hz), 1.92-2.06(2H, m), 3.29(4H, brs), 3.54(1H, s), 3.91(1H, s), 3.94(4H, brs), 7.41(1H, d, J = 7.6 Hz), 7.60(1H, dd, J = 7.6, 8.1 Hz), 8.01(1H, d, J = 8.1 Hz), 8.13(2H, s), 9.62(1H, brs); ESI+: 466 |
| 71 | 1 | NMR1: 1.06-1.22(2H, m), 1.56(1H, d, J = 8.9 Hz), 1.70(1H, d, J = 8.9 Hz), 1.91-2.03(2H, m), 3.46(1H, s), 3.54(4H, brs), 3.64(4H, brs), 3.90(1H, s), 7.24(1H, d, J = 7.7 Hz), 7.51(1H, dd, J = 7.7, 8.3 Hz), 8.01(1H, s), 8.15(1H, d, J = 8.3 Hz), 8.21(s, 1H), 8.88(1H, s); ESI+: 418 |
| 72 | 4 | NMR1: 1.05-1.16(1H, m), 1.16-1.27(1H, m), 1.57(1H, d, J = 8.9 Hz), 1.73(1H, d, J = 8.9 Hz), 1.91-2.04(2H, m), 3.29(4H, brs), 3.54(1H, s), 3.90(1H, s), 3.94(4H, brs), 7.40-7.52(1H, m), 7.63(1H, ddd, J = 2.7, 4.1, 8.9 Hz), 8.00(1H, dd, J = 2.7, 6.7 Hz), 8.08(1H, s), 9.63(1H, brs); ESI+: 450 |

TABLE 97

| Ex | Syn | Data |
|---|---|---|
| 73 | 1 | NMR: 1.05-1.21(2H, m), 1.55(1H, d, J = 8.9 Hz), 1.69(1H, d, J = 8.9 Hz), 1.89-2.03(2H, m), 3.45(1H, s), 3.53(4H, brs), 3.64(4H, brs), 3.86(1H, s), 7.31-7.37(1H, m), 7.73(1H, ddd, J = 2.7, 4.2, 9.1 Hz), 7.99(1H, s), 8.14(1H, dd, J = 2.7, 6.9 Hz), 8.72(1H, s); ESI+: 402 |

TABLE 97-continued

| Ex | Syn | Data |
|---|---|---|
| 74 | 1 | NMR1: 1.05-1.21(2H, m), 1.55(1H, d, J = 8.9 Hz), 1.70(1H, d, J = 8.9 Hz), 1.91-2.02(2H, m), 3.27(4H, brs), 3.51(1H, s), 3.87(1H, s), 3.94(4H, brs), 7.36(1H, dd, J = 9.3, 19.8 Hz), 7.48-7.55(1H, m), 8.04(1H, ddd, J = 2.6, 7.5, 14.0 Hz), 8.10(1H, s), 8.87(1H, s); ESI+: 434 |
| 75 | 1 | NMR1: 1.05-1.22(2H, m), 1.55(1H, d, J = 8.9 Hz), 1.69(1H, d, J = 8.9 Hz), 1.90-2.04(2H, m), 3.46(1H, s), 3.53(4H, brs), 3.64(4H, brs), 3.86(1H, s), 7.34(1H, dd, J = 9.3, 19.9 Hz), 7.48-7.56(1H, m), 7.99(1H, s), 8.04(1H, ddd, J = 2.7, 7.5, 14.2 Hz), 8.74(1H, s); ESI+: 386 |
| 76 | 1 | NMR: 0.98-1.13(2H, m), 1.45(1H, d, J = 8.9 Hz), 1.54(1H, d, J = 8.9 Hz), 1.73-2.19(14H, m), 2.38-2.47(1H, m), 3.38-3.76(10H, m), 4.89(1H, s), 7.99(1H, s); ESI+: 444 |
| 77 | 1 | NMR: 0.97-1.15(2H, m), 1.45(1H, d, J = 8.8 Hz), 1.54(1H, d, J = 8.8 Hz), 1.73-1.93(8H, m), 1.99-2.2(6H, m), 2.41-2.49(1H, m), 3.23(4H, brs), 3.56(1H, brs), 3.75(1H, brs), 3.88-4.11(4H, m), 5.02(1H, s), 8.02(1H, s); ESI+: 492 |
| 78 | 1 | NMR: 1.08-1.2(2H, m), 1.52(1H, d, J = 9 Hz), 1.68(1H, d, J = 9 Hz), 1.80-2.00(2H, m), 3.18(3H, s), 3.37-3.7(10H, m), 7.28-7.36(2H, m), 7.46-7.51(2H, m), 8.23(1H, s), 8.6(1H, s); ESI+: 428 |
| 79 | 1 | NMR1: 1.07-1.23(2H, m), 1.52(1H, d, J = 8.9 Hz), 1.68(1H, d, J = 8.9 Hz), 1.86-1.99(2H, m), 3.17-3.31(7H, m), 3.5(1H, brs), 3.61(1H, brs), 3.85-4.13(4H, m), 7.33-7.38(2H, m), 7.49-7.53(2H, m), 8.24(1H, s), 8.65(1H, s); ESI+: 476 |
| 80 | 1 | NMR1: 1.07-1.2(2H, m), 1.52(1H, d, J = 9 Hz), 1.68(1H, d, J = 9 Hz), 1.86-2.12(6H, m), 3.19(3H, s), 3.47-3.82(6H, m), 7.31-7.37(2H, m), 7.47-7.52(2H, m), 8.23(1H, s), 8.61(1H, s); ESI+: 462 |
| 81 | 1 | NMR: 1.08-1.2(2H, m), 1.51(1H, d, J = 8.8 Hz), 1.67(1H, d, J = 8.8 Hz), 1.87-1.99(2H, m), 2.39-2.52(3H, m), 3.19(3H, s), 3.51(1H, brs), 3.71-4.09(4H, m), 7.34-7.39(2H, m), 7.49-7.53(2H, m), 8.26(1H, s), 8.66(1H, s); ESI+: 448 |
| 82 | 4 | NMR: 1.05-1.15(2H, m), 1.23(3H, s), 1.29(1.5H, s), 1.30(1.5H, s), 1.35-1.47(1H, m), 1.51-1.67(2H, m), 1.68-1.75(1H, m), 1.76-1.85(1H, m), 1.89-2.01(3H, m), 3.30(4H, brs), 3.50(4H, brs), 3.67-3.75(1H, m), 3.75-4.00(3H, m), 4.39-4.52(1H, m), 8.00(0.5H, s), 8.01(0.5H, s); ESI+: 434 |

TABLE 98

| Ex | Syn | Data |
|---|---|---|
| 83 | 4 | NMR1: 1.04-1.15(2H, m), 1.23(3H, s), 1.28(1.5H, s), 1.29(1.5H, s), 1.35-1.48(1H, m), 1.52-1.66(2H, m), 1.68-1.75(1H, m), 1.76-1.88(1H, m), 1.89-2.03(3H, m), 3.41-3.50(5H, brm), 3.64(4H, brs), 3.68-3.79(2H, m), 3.86(0.5H, s), 3.92(0.5H, s), 4.32-4.45(1H, m), 7.83(1H, s); ESI+: 386 |
| 84 | 1 | NMR1: 1.06-1.20(2H, m), 1.52(1H, d, J = 9.2 Hz), 1.67(1H, d, J = 9.2 Hz), 1.85-2.00(2H, m), 3.36-3.44(1H, m), 3.44-3.58(5H, m), 3.60-3.72(4H, m), 7.15(1H, d, J = 7.7 Hz), 7.23(1H, brs), 7.25-7.30(1H, m), 7.45(1H, dd, J = 7.8, 7.7 Hz), 8.20(1H, s), 8.50(1H, s); ESI+: 418 |
| 85 | 1 | NMR1: 1.06-1.23(2H, m), 1.52(1H, d, J = 8.8 Hz), 1.67(1H, d, J = 8.8 Hz), 1.86-2.00(2H, m), 3.18-3.30(4H, m), 3.49(1H, brs), 3.61(1H, brs), 3.83-3.98(2H, m), 3.98-4.15(2H, m), 7.18(1H, d, J = 7.8 Hz), 7.27(1H, brs), 7.29-7.34(1H, m), 7.47(1H, dd, J = 8.0, 7.8 Hz), 8.21(1H, s), 8.54(1H, s); ESI+: 466 |
| 86 | 1 | NMR1: 1.06-1.20(2H, m), 1.48(1H, d, J = 9.0 Hz), 1.63(1H, d, J = 9.0 Hz), 1.83-1.97(2H, m), 2.25(3H, s), 3.37-3.46(1H, m), 3.47-3.58(5H, m), 3.58-3.71(4H, m), 6.71(1H, d, J = 7.6 Hz), 6.82-6.89(2H, m), 7.13(1H, t, J = 7.6 Hz), 8.02(1H, s), 8.13(1H, s); ESI+: 364 |
| 87 | 1 | NMR1: 1.05-1.22(2H, m), 1.49(1H, d, J = 9.2 Hz), 1.63(1H, d, J = 9.2 Hz), 1.84-1.97(2H, m), 2.26(3H, s), 3.18-3.28(4H, m), 3.55(1H, brs), 3.59(1H, brs), 3.85-4.13(4H, m), 6.74(1H, d, J = 7.6 Hz), 6.86-6.92(2H, m), 7.15(1H, t, J = 7.6 Hz), 8.08(1H, s), 8.13(1H, s); ESI+: 412 |
| 88 | 4 | NMR1: 1.12-1.21(2H, m), 1.58(1H, d, J = 9.2 Hz), 1.73(1H, d, J = 9.2 Hz), 1.93-2.02(2H, m), 2.69-2.79(1H, m), 2.92-3.05(1H, m), 3.12-4.58(10H, m), 7.11-7.17(1H, m), 7.29-7.39(2H, m), 8.19(1H, s), 8.65(1H, brs); ESI+: 432 |
| 89 | 1 | NMR1: 1.04-1.19(2H, m), 1.53(1H, d, J = 8.8 Hz), 1.68(1H, d, 8.8 Hz), 1.89-2.00(2H, m), 2.31(3H, m), 3.27(4H, brs), 3.50(1H, s), 3.86(1H, s), 3.94(4H, brs), 6.75-6.80(1H, m), 7.14-7.21(1H, m), 7.57(1H, s), 7.59-7.63(1H, m), 8.07(1H, s), 8.48(1H, brs); ESI+: 412 |
| 90 | 1 | NMR1: 1.03-1.19(2H, m), 1.53(1H, d, J = 8.8 Hz), 1.67(1H, d, J = 8.8 Hz), 1.88-2.01(2H, m), 2.31(3H, s), 3.44(1H, s), 3.53(4H, brs), 3.64(4H, m), 3.86(1H, s), 6.76(1H, d, J = 7.4 Hz), 7.17(1H, dd, J = 7.4, 8.1 Hz), 7.56(1H, s), 7.61(1H, d, J = 8.1 Hz), 7.95(1H, s), 8.44(1H, s); ESI+: 364 |
| 91 | 1 | NMR1: 1.36-1.46(m, 2H), 1.63-1.82(m, 6H), 1.83-1.93(m, 4H), 2.11-2.16(m, 1H), 2.35-2.42(m, 2H), 2.49-2.58 (m, 4H), 3.22(brs, 4H), 3.79(brs, 4H), 5.68(s, 1H), 7.85(s, 1H); ESI+: 404 |
| 92 | 1 | NMR1: 0.99-1.09(2H, m), 1.35-1.43(2H, m), 1.44(1H, d, J = 8.7 Hz), 1.58(1H, d, J = 8.7 Hz), 1.67-1.79(4H, m), 1.79-1.95(6H, m), 2.10-2.16(1H, m), 3.20-3.28(4H, m), 3.42(1H, s), 3.69(1H, s), 3.85-4.02(4H, m), 6.43(1H, s), 7.91(1H, s); ESI+: 416 |

TABLE 99

| Ex | Syn | Data |
|---|---|---|
| 93 | 1 | NMR1: 0.98-1.09(2H, m), 1.35-1.43(2H, m), 1.44(1H, d, J = 8.7 Hz), 1.57(1H, d, J = 8.7 Hz), 1.67-1.84(6H, m), 1.85-1.96(4H, m), 2.10-2.15(1H, m), 3.37(1H, s), 3.44-3.58(4H, m), 3.61-3.66(4H, m), 3.68(1H, s), 6.36(1H, s), 7.80(1H, s); ESI+: 368 |
| 94-1 | 5 | NMR1: 1.06-1.21(2H, m), 1.51(1H, d, J = 9 Hz), 1.66(1H, d, J = 9 Hz), 1.85-1.99(2H, m), 3.18-3.29(4H, m), 3.51(1H, b.s), 3.6(1H, b.s), 3.82-4.14(4H, m), 6.9(1H, dd, J = 1.5, 7.8 Hz), 6.98-7.03(2H, m), 7.26(1H, dd, J = 7.8, 8.1 Hz), 8.18(1H, s), 8.38(1H, s); ESI+: 432 |
| 94-2 | 5 | NMR1: 1.06-1.21(2H, m), 1.51(1H, d, J = 9 Hz), 1.66(1H, d, J = 9 Hz), 1.85-1.99(2H, m), 3.18-3.29(4H, m), 3.51(1H, brs), 3.6(1H, brs), 3.82-4.14(4H, m), 6.9(1H, dd, J = 1.5, 7.8 Hz), 6.98-7.03(2H, m), 7.26(1H, dd, J = 7.8, 8.1 Hz), 8.18(1H, s), 8.38(1H, s); ESI+: 432 |
| 95 | 1 | NMR1: 1.10-1.21(1H, m), 1.24-1.34(1H, m), 1.62(1H, d, J = 9.1 Hz), 1.81(1H, d, J = 9.1 Hz), 1.96-2.09(2H, m), 3.28(4H, brs), 3.59(1H, s), 3.61(1H, s), 3.84(4H, brs), 7.49-7.54(1H, m), 7.58-7.64(2H, m), 7.67-7.73(1H, m), 8.05(1H, s); ESI+: 467 |
| 96 | 1 | NMR1: 1.09-1.19(1H, m), 1.23-1.32(1H, m), 1.63(1H, d, J = 9.1 Hz), 1.81(1H, d, J = 9.1 Hz), 1.95-2.09(2H, m), 3.35(4H, brs), 3.52(1H, s), 3.61(1H, s), 3.63(4H, brs), 7.48-7.53(1H, m), 7.56-7.64(2H, m), 7.65-7.72(1H, m), 7.94(1H, s); ESI+: 419 |
| 97 | 4 | NMR1: 1.27-1.31(4H, m), 1.77-1.82(4H, m), 3.09(1H, brs), 3.26-3.3(3H, m), 3.5-3.55(2H, m), 3.68(4H, brs), 6.86(1H, dd, J = 1.7, 7.6 Hz), 6.91(1H, dd, J = 1.7, 8.3 Hz), 6.96(1H, t, J = 1.7 Hz), 7.24(1H, dd, J = 7.6, 8.3 Hz), 8.33(1H, s), 8.41(1H, brs); ESI+: 398 |
| 98 | 4 | NMR1: 1.27-1.3(4H, m), 1.76-1.8(4H, m), 3.15-3.2(3H, m), 3.27-3.34(3H, m), 3.69-3.74(4H, m), 4.06-4.11(2H, m), 6.85(1H, ddd, J = 0.8, 2.0, 7.9 Hz), 6.9(1H, ddd, J = 0.8, 2.1, 8.1 Hz), 6.96(1H, dd, J = 2.0, 2.1 Hz), 7.24(1H, dd, J = 7.9, 8.1 Hz), 8.33(1H, s), 8.40(1H, s); ESI+: 446; Temp: 165.3 |
| 99 | 4 | NMR1: 1.05-1.13(2H, m), 1.44-1.54(2H, m), 1.55-1.63(2H, m), 1.64-1.78(4H, m), 1.87-2.03(6H, m), 2.06-2.15(2H, m), 2.26(2H, brs), 3.50(1H, s), 3.64-4.03(9H, brm), 7.98(1H, s); ESI+: 472 |
| 100 | 4 | NMR1: 1.04-1.14(2H, m), 1.44-1.55(2H, m), 1.56-1.63(2H, m), 1.56-1.63(2H, m), 1.65-1.78(4H, m), 1.88-2.02(6H, m), 2.07-2.15(2H, m), 2.26(2H, brs), 3.45(1H, s), 3.47-3.80(8H, brm), 3.94(1H, s), 7.88(1H, s); ESI+: 424 |
| 101 | 4 | NMR1: 1.24-1.43(4H, m), 1.75-1.90(4H, m), 3.14(1H, s), 3.33(4H, brs), 3.68(1H, s), 3.79(4H, brs), 7.09-7.16(1H, m), 7.36-7.43(1H, m), 7.57-7.62(1H, m), 7.85(1H, s), 8.14(1H, s), 9.25(1H, brs); ESI+: 446; Temp: 159.1 |
| 102 | 4 | NMR1: 1.24-1.45(4H, m), 1.77-1.92(4H, m), 3.10(1H, s), 3.36(4H, brs), 3.67(1H, s), 3.70(4H, brs), 7.08-7.15(1H, m), 7.35-7.42(1H, m), 7.56-7.62(1H, m), 7.84(1H, s), 8.01(1H, s), 9.22(1H, brs); ESI+: 398 |

TABLE 100

| Ex | Syn | Data |
|---|---|---|
| 103 | 4 | NMR1: 1.24-1.45(4H, m), 1.75-1.91(4H, m), 3.14(1H, s), 3.34(4H, brs), 3.69(1H, s), 3.78(4H, brs), 6.99-7.05 (1H, m), 7.44-7.51(1H, m), 7.67-7.72(1H, m), 7.80(1H, m), 8.15(1H, s), 9.29(1H, m); ESI+: 496 |
| 104 | 4 | NMR1: 1.23-1.45(4H, m), 1.76-1.91(4H, m), 3.10(1H, s), 3.27-3.80(9H, m), 6.97-7.05(1H, m), 7.43-7.50(1H, m), 7.66-7.73(1H, m), 7.78(1H, s), 8.01(1H, s), 9.23(1H, brs); ESI+: 448 |
| 105 | 4 | NMR: 1.08-1.25(2H, m), 1.58(1H, d, J = 8.9 Hz), 1.73 (1H, d, J = 8.9 Hz), 1.92-2.04(2H, m), 3.29(4H, brs), 3.54 (1H, s), 3.90(1H, s), 3.95(4H, brs), 6.84-6.98(1H, m), 7.36-7.48 (2H, m), 7.69(1H, d, J = 11.7 Hz), 8.10(1H, s), 9.54(1H, brs); ESI+: 416 |
| 106 | 4 | NMR: 1.05-1.26(2H, m), 1.58(1H, d, J = 9.0 Hz), 1.73(1H, d, J = 9.0 Hz), 1.92-2.06(2H, m), 3.29(4H, s), 3.54(4H, brs), 3.65(4H, brs), 3.90(4H, s), 6.87(1H, dd, J = 8.0, 8.2 Hz), 7.38 (1H, dd, J = 8.0, 15.1 Hz), 7.47(1H, d, J = 8.2 Hz), 7.73 (1H, d, J = 11.9 Hz), 7.99(1H, s), 9.30(1H, brs); ESI+: 368 |
| 107 | 4 | NMR1: 1.18-1.42(4H, m), 1.69-1.9(4H, m), 3.07(1H, brs), 3.32(2H, brs), 3.43-3.78(7H, m), 6.81-6.93(1H, m), 7.32-7.43(2H, m), 7.59(1H, d, J = 11.8 Hz), 7.96(1H, s), 9.32(1H, brs); ESI+: 382 |
| 108 | 4 | NMR1: 1.2-1.41(4H, m), 1.71-1.9(4H, m), 3.1(1H, brs), 3.3 (4H, brs), 3.65(1H, s), 3.75(4H, brs), 6.8-6.92(1H, m), 7.32-7.43(2H, m), 7.61(1H, d, J = 12 Hz), 8.1(1H, s), 9.27(1H, brs); ESI+: 430 |
| 109 | 4 | NMR1: 1.2-1.42(4H, m), 1.73-1.9(4H, m), 2.33(3H, s), 3.09(1H, brs), 3.33(2H, brs), 3.43-3.76(7H, m), 7.05 (1H, d, J = 6.6 Hz), 7.27-7.37(3H, m), 7.85(1H, s), 9.63(1H, brs); ESI+: 378 |
| 110 | 4 | NMR1: 1.22-1.4(4H, m), 1.74-1.87(4H, m), 2.33(3H, s), 3.05-3.39(5H, m), 3.49-3.98(5H, m), 7.03(1H, brs), 7.26-7.4(3H, m), 8(1H, s), 9.51(1H, brs); ESI+: 426 |
| 111 | 4 | NMR1: 1.19-1.41(4H, m), 1.72-1.87(4H, m), 3.06 (1H, brs), 3.31(2H, brs), 3.42-3.78(7H, m), 7.31(1H, d, J = 7.4 Hz), 7.53(1H, t, J = 7.9 Hz), 7.94-8.01(2H, m), 8.04(1H, s), 9.14(1H, s); ESI+: 432 |
| 112 | 4 | NMR1: 1.22-1.39(4H, m), 1.73-1.86(4H, m), 3.1(1H, brs), 3.29(4H, brs), 3.65(1H, s), 3.75(4H, brs), 7.32 (1H, d, J = 7.5 Hz), 7.54(1H, t, J = 8 Hz), 7.97(1H, d, J = 8.1 Hz), 8.07(1H, s), 8.12(1H, s), 9.19(1H, brs); ESI+: 480; Temp: 159.8 |
| 113 | 4 | NMR1: 1.24-1.44(4H, m), 1.75-1.92(4H, m), 3.14(1H, s), 3.34(4H, brs), 3.68(1H, s), 3.78(4H, brs), 7.41-7.48(1H, m), 7.60(1H, ddd, J = 2.7, 4.2, 8.9 Hz), 7.96-8.01(1H, m), 8.11(1H, s), 9.32(1H, brs); ESI+: 464 |
| 114 | 4 | NMR1: 1.23-1.46(4H, m), 1.77-1.92(4H, m), 3.11(1H, s), 3.25-3.85(9H, m), 7.42-7.50(1H, m), 7.60(1H, ddd, J = 2.7, 4.2, 8.9 Hz), 7.92-7.98(1H, m), 7.97(1H, s), 9.49(1H, s); ESI+: 416 |

TABLE 101

| Ex | Syn | Data |
|---|---|---|
| 115 | 4 | NMR: 1.24-1.46(4H, m), 1.75-1.91(4H, m), 3.14(1H, s), 3.33(4H, brs), 3.68(1H, s), 3.77(4H, brs), 7.48-7.56 (1H, m), 8.02-8.08(1H, m), 8.11-8.17(1H, m), 8.13(1H, s), 9.31(1H, brs); ESI+: 498 |
| 116 | 4 | NMR1: 1.23-1.46(4H, m), 1.76-1.92(4H, m), 3.10(1H, s), 3.34(4H, brs), 3.47-3.80(5H, m), 7.46-7.55(1H, m), 7.99(1H, m), 8.03-8.09(1H, m), 8.11 (1H, dd, J = 2.6, 6.4 Hz), 9.23(1H, brs); ESI+: 450 |
| 117-1 | 4 | NMR1: 1.06-1.26(2H, m), 1.57(1H, d, J = 9.0 Hz), 1.73(1H, d, J = 9.0 Hz), 1.91-2.06(2H, m), 3.29(4H, brs), 3.54(1H, s), 3.89(1H, s), 3.94(4H, brs), 7.11 (1H, d, J = 7.5 Hz), 7.39(1H, t, J = 8.1 Hz), 7.60-7.67(1H, m), 7.92(1H, s), 8.11(1H, s), 9.32(1H, brs); ESI+: 432; [a]D: +81.4(c = 0.535, MeOH) |
| 117-2 | 4 | NMR1: 1.06-1.26(2H, m), 1.58(1H, d, J = 9.0 Hz), 1.73(1H, d, J = 9.0 Hz), 1.91-2.06(2H, m), 3.29(4H, brs), 3.54(1H, s), 3.90(1H, s), 3.95(4H, brs), 7.14(1H, d, J = 7.6 Hz), 7.40(1H, dd, J = 7.6, 8.2 Hz), 7.62(1H, d, J = 8.2 Hz), 7.89(1H, s), 8.11(1H, s), 9.47(1H, brs); ESI+: 432; [a]D: −77.1(c = 0.53, MeOH); Temp: 172.9 |
| 118 | 4 | NMR1: 1.05-1.16(1H, m), 1.17-1.28(1H, m), 1.59(1H, d, J = 9.0 Hz), 1.73(1H, d, J = 9.0 Hz), 1.92-2.06(2H, m), 3.49 (1H, s), 3.56(4H, brs), 3.65(4H, brs), 3.89(1H, s), 7.14(1H, d, J = 7.4 Hz), 7.40(1H, dd, J = 7.4, 8.2 Hz), 7.60(1H, d, J = 8.2 Hz), 7.87(1H, s), 7.98(1H, s), 9.49(1H, brs); ESI+: 384; [a]D: +74.0(c = 0.525, MeOH) |
| 119-1 | 4 | NMR1: 1.02-1.22(2H, m), 1.53(1H, d, J = 9 Hz), 1.69(1H, d, J = 9 Hz), 1.89-2(2H, m), 3.25(4H, brs), 3.5(1H, brs), 3.84(1H, brs), 3.9(4H, brs), 7.4(1H, t, J = 9.1 Hz), 7.59-7.65(1H, m), 8.01(1H, dd, J = 2.4, 6.7 Hz), 8.05(1H, s), 9.32 (1H, brs); ESI+: 450; [a]D: +68.0(c0.525, MeOH) |
| 119-2 | 4 | NMR1: 1.05-1.16(1H, m), 1.16-1.27(1H, m), 1.57(1H, d, J = 8.9 Hz), 1.73(1H, d, J = 8.9 Hz), 1.91-2.04(2H, m), 3.28 (4H, brs), 3.54(1H, s), 3.88(1H, s), 3.94(4H, brs), 7.40-7.48(1H, m), 7.65(1H, ddd, J = 2.7, 4.1, 8.9 Hz), 8.04(1H, dd, J = 2.7, 6.7 Hz), 8.08(1H, s), 9.41(1H, brs); ESI+: 450; [a]D: −71.5(c = 0.465, MeOH); Temp: 178.2 |
| 120-1 | 4 | NMR1: 1.02-1.22(2H, m), 1.53(1H, d, J = 9.2 Hz), 1.69(1H, d, J = 9.2 Hz), 1.89-2(2H, m), 3.25(4H, brs), 3.49(1H, brs), 3.86(1H, brs), 3.9(4H, b.s), 6.96(1H, d, J = 7.8 Hz), 7.43(1H, t, J = 8.3 Hz), 7.7(1H, d, J = 8.3 Hz), 7.85(1H, s), 8.08(1H, s), 9.26(1H, brs); ESI+: 482; [a]D: +70.4(c0.490, MeOH) |
| 120-2 | 4 | NMR1: 1.05-1.28(2H, m), 1.58(1H, d, J = 8.9 Hz), 1.73(1H, d, J = 8.9 Hz), 1.92-2.04(2H, m), 3.29(4H, brs), 3.54(1H, s), 3.90(1H, s), 3.94(4H, brs), 7.02(1H, d, J = 8.0 Hz), 7.47(1H, dd, J = 8.0, 8.2 Hz), 7.73(1H, d, J = 8.2 Hz), 7.87(1H, s), 8.12(1H, s), 9.39(1H, brs); ESI+: 482; [a]D: −76.4 (c = 0.495, MeOH); Temp: 159.4 |

TABLE 102

| Ex | Syn | Data |
|---|---|---|
| 121 | 4 | NMR1: 1.03-1.23(2H, m), 1.54(1H, d, J = 8.8 Hz), 1.7(1H, d, J = 8.8 Hz), 1.89-2.02(2H, m), 2.25(3H, d, J = 1.5 Hz), 3.24(4H, brs), 3.51(1H, brs), 3.8(1H, brs), 7.18(1H, t, J = 9 Hz), 7.37-7.51(2H, m), 7.95(1H, s), 9.47(1H, brs); ESI+: 430 |
| 122 | 4 | NMR1: 1.11-1.18(2H, m), 1.56(1H, d, J = 9.1 Hz), 1.72 (1H, d, J = 9.1 Hz), 1.92-1.99(2H, m), 3.38-3.72(10H, m), 7.31 (1H, dt, J = 7.5, 1.2 Hz), 7.36-7.42(2H, m), 7.46(1H, t, J = 7.9 Hz), 8.28(1H, s), 8.7(1H, m, brs); ESI+: 375 |
| 123 | 4 | NMR1: 1.09-1.22(2H, m), 1.53(1H, d, J = 9 Hz), 1.69(1H, d, J = 9 Hz), 1.88-1.99(2H, m), 3.2-3.31(4H, m), 3.53(1H, brs), 3.61(1H, brs), 3.84-4.14(4H, m), 7.29(1H, dt, J = 7.5, 1.2 Hz), 7.34-7.38(2H, m), 7.45(1H, t, J = 8 Hz), 8.24(1H, s), 8.6(1H, brs); ESI+: 423 |
| 124 | 4 | NMR1: 1.26-1.31(4H, m), 1.77-1.81(4H, m), 3.09(1H, brs), 3.25-3.27(2H, m), 3.31(1H, brs), 3.51-3.53(2H, m), 3.68(4H, brs), 6.77(1H, d, J = 8.2 Hz), 6.87(1H, brs), 6.95(1H, d, J = 8.2 Hz), 7.33(1H, t, J = 8.2 Hz), 8.35(1H, s), 8.47(1H, brs); ESI+: 448 |
| 125 | 4 | NMR1: 1.27-1.32(4H, m), 1.76-1.81(4H, m), 3.15-3.19(3H, m), 3.3-3.33(3H, m), 3.7-3.72(2H, m), 4.02-4.04(2H, m), 6.78 (1H, d, J = 8.2 Hz), 6.89(1H, brs), 6.97(1H, d, J = 8.2 Hz), 7.33(1H, t, J = 8.2 Hz), 8.36(1H, s), 8.48(1H, brs); ESI+: 496; Temp: 178.2 |
| 126 | 4 | NMR1: 1.25-1.31(4H, m), 1.76-1.82(4H, m), 3.09(1H, brs), 3.23-3.27(2H, m), 3.32(1H, b.s), 3.51-3.53(2H, m), 3.66 (4H, brs), 6.74-6.81(1H, m), 6.98(1H, ddd, J = 2.7, 7, 13 Hz), 7.25-7.33(1H, m), 8.29(2H, s); ESI+: 400 |
| 127 | 4 | NMR1: 1.27-1.31(4H, m), 1.77-1.81(4H, m), 3.17-3.19(3H, m), 3.31-3.38(3H, m), 3.69-3.73(2H, m), 4.03-4.07(2H, m), 6.81-6.85(1H, m), 7.03(1H, ddd, J = 2.6, 7, 12.8 Hz), 7.28-7.35(1H, m), 8.31(1H, s), 8.38(1H, brs); ESI+: 448; Temp: 177.4 |
| 128 | 4 | NMR1: 1.2-1.28(4H, m), 1.73-1.83(10H, m), 1.99-2.19(7H, m), 2.42-2.5(1H, m), 3.13-3.22(3H, m), 3.28-3.36(2H, m), 3.57-3.61(1H, m), 3.66-3.72(2H, m), 4.05-4.1(2H, m), 8.22(1H, s); ESI+: 506 |
| 129 | 4 | NMR1: 1.26-1.32(4H, m), 1.76-1.82(4H, m), 3.15-3.19(3H, m), 3.29-3.34(3H, m), 3.68-3.74(2H, m), 4.06-4.1(2H, m), 7.29-7.33(1H, m), 7.36-7.41(1H, m), 8.32(1H, s), 8.49(1H, brs); ESI+: 498 |
| 130 | 4 | NMR1: 1.30(4H, d, J = 10.8 Hz), 1.81(4H, d, J = 10.8 Hz), 3.11 (1H, brs), 3.28(2H, t, J = 4.5 Hz), 3.37(1H, brs), 3.54(2H, t, J = 4.5 Hz), 3.69(4H, s), 7.19(1H, d, J = 7.8 Hz), 7.26- |

TABLE 102-continued

| Ex | Syn | Data |
|---|---|---|
| | | 7.32(2H, m), 7.47(1H, dd, J = 8.0, 7.8 Hz), 8.39(1H, s), 8.73(1H, brs); ESI+: 432 |
| 131 | 4 | NMR1: 1.30(4H, d, J = 8.2 Hz), 1.80(4H, d, J = 8.2 Hz), 3.16-3.25(3H, m), 3.29-3.38(3H, m), 3.68-3.76(2H, m), 4.05-4.14(2H, m), 7.18(1H, d, J = 7.7 Hz), 7.26-7.32(2H, m), 7.47(1H, dd, J = 7.8, 7.7 Hz), 8.38(1H, s), 8.67(1H, brs); ESI+: 480 |

TABLE 103

| Ex | Syn | Data |
|---|---|---|
| 132-1 | 4 | NMR1: 1.02-1.20(2H, m), 1.53(1H, d, J = 9.2 Hz), 1.68(1H, d, J = 9.2 Hz), 1.89-2.00(2H, m), 3.24(4H, brs), 3.49(1H, s), 3.85(1H, s), 3.90(4H, brs), 7.34-7.47(2H, m), 7.87-7.96(1H, m), 8.05(1H, s), 9.26(1H, brs); ESI+: 434; [a]D: +75.0(c0.550, MeOH) |
| 132-2 | 4 | NMR1: 1.06-1.25(2H, m), 1.58(1H, d, J = 9.0 Hz), 1.73(1H, d, J = 9.0 Hz), 1.92-2.04(2H, m), 3.29(4H, brs), 3.53(1H, s), 3.89(1H, s), 3.94(4H, brs), 7.39-7.51(2H, m), 7.93(1H, d, J = 7.7, 13.5 Hz), 8.08(1H, s), 9.44(1H, brs); ESI+: 434; [a]D: −73.4(c = 0.40, MeOH) |
| 133-1 | 4 | NMR1: 1.03-1.21(2H, m), 1.54(1H, d, J = 8.8 Hz), 1.68(1H, d, J = 8.8 Hz), 1.89-2.00(2H, m), 3.24(4H, brs), 3.49(1H, s), 3.84(1H, s), 3.90(4H, brs), 7.46(1H, t, J = 9.8 Hz), 8.04-8.10(1H, m), 8.06(1H, s), 8.17(1H, dd, J = 2.6, 6.0 Hz), 9.24(1H, brs); ESI+: 484 ; [a]D: +60.0(c0.485, MeOH) |
| 133-2 | 4 | NMR1: 1.06-1.16(1H, m), 1.16-1.25(1H, m), 1.58(1H, d, J = 8.9 Hz), 1.72(1H, d, J = 8.9 Hz), 1.92-2.06(2H, m), 3.28(4H, brs), 3.53(1H, s), 3.89(1H, s), 3.93(4H, brs), 7.47-7.54(1H, m), 8.07-8.13(1H, m), 8.10(1H, s), 8.20(1H, dd, J = 2.6, 6.3 Hz), 9.33(1H, brs); ESI+: 484; [a]D: −65.5(c = 0.535, MeOH); Temp: 184.1 |
| 134 | 4 | NMR1: 1.15(6H, s), 1.27-1.40(4H, m), 1.77-1.90(4H, m), 3.25(1H, s), 3.26(1H, s), 3.67(2H, s), 7.42-7.50(1H, m), 7.60(1H, ddd, J = 2.8, 4.2, 9.0 Hz), 7.96-8.02(1H, m), 8.15(1H, s), 8.33(1H, brs), 9.34(1H, brs); ESI+: 418 |
| 135-1 | 4 | NMR1: 1.03-1.25(2H, m), 1.54(1H, d, J = 8.8 Hz), 1.72(1H, d, J = 9.2 Hz), 1.86-2.04(2H, m), 2.33(3H, s), 3.25(4H, brs), 3.51(1H, s), 3.81(1H, s), 3.90(4H, brs), 6.95-7.08(1H, m), 7.26-7.41(3H, m), 7.97(1H, s), 9.65(1H, brs); ESI+: 412 |
| 135-2 | 4 | NMR1: 1.08-1.18(1H, m), 1.19-1.29(1H, m), 1.58(1H, d, J = 9.0 Hz), 1.76(1H, d, J = 9.0 Hz), 1.91-2.07(2H, m), 2.37(3H, s), 3.29(4H, brs), 3.56(1H, s), 3.85(1H, s), 3.94(4H, s), 7.03-7.13(1H, m), 7.31-7.43(3H, m), 8.02(1H, s), 9.86(1H, brs); ESI+: 412; [a]D: −89.3(c = 0.44, MeOH) |
| 136-1 | 4 | NMR1: 1.03-1.25(2H, m), 1.55(1H, d, J = 8.8 Hz), 1.71(1H, d, J = 8.8 Hz), 1.90-2.02(2H, m), 3.25(4H, brs), 3.51(1H, s), 3.77(3H, s), 3.84(1H, s), 3.90(4H, brs), 6.75(1H, d, J = 8.0 Hz), 7.15(1H, d, J = 8.0 Hz), 7.22(1H, d, J = 7.7 Hz), 7.31(1H, t, J = 8.0 Hz), 7.99(1H, s), 9.58(1H, brs); ESI+: 428 |
| 136-2 | 4 | NMR1: 1.07-1.18(1H, m), 1.18-1.29(1H, m), 1.59(1H, d, J = 9.0 Hz), 1.75(1H, d, J = 9.0 Hz), 1.92-2.07(2H, m), 3.29(4H, brs), 3.55(1H, s), 3.81(3H, s), 3.88(1H, s), 3.94(4H, brs), 6.79(1H, d, J = 6.9 Hz), 7.18(1H, d, J = 7.7 Hz), 7.26(1H, s), 7.35(1H, dd, J = 6.9, 7.7 Hz), 8.03(1H, s), 9.66(1H, brs); ESI+: 428; [a]D: −78.7(c = 0.44, MeOH) |
| 137 | 4 | NMR1: 1.22-1.33(4H, m), 1.44-1.53(4H, m), 1.55-1.63(2H, m), 1.65-1.82(7H, m), 1.95-2.04(4H, m), 2.05-2.13(2H, m), 2.26(2H, brs), 3.09(1H, s), 3.15-3.98(9H, brm), 8.02(1H, s); ESI+: 486 |

TABLE 104

| Ex | Syn | Data |
|---|---|---|
| 138 | 4 | NMR1: 1.24-1.44(4H, m), 1.74-1.91(4H, m), 3.14(1H, s), 3.34(4H, m), 3.69(1H, s), 3.78(4H, brs), 7.40-7.52(2H, m), 7.82-7.94(1H, m), 8.11(1H, s), 9.34(1H, brs); ESI+: 448; Temp: 186.5 |
| 139 | 4 | NMR1: 1.27-1.47(4H, m), 1.74-1.92(4H, m), 3.16(1H, s), 3.36(4H, brs), 3.74(1H, s), 3.81(3H, s), 4.20(4H, brs), 6.83(1H, d, J = 7.4 Hz), 7.14(1H, d, J = 7.8 Hz), 7.21(1H, s), 7.38(1H, dd, J = 7.4, 7.8 Hz), 8.07(1H, s), 9.73(1H, brs); ESI+: 442 |
| 140 | 1 | NMR1: 2.00-2.15(214, m), 2.80-2.95(4H, m), 3.15-3.27(4H, m), 3.75-4.05(4H, m), 6.96(1H, dd, J = 8, 2 Hz), 7.28(1H, t, J = 8 Hz), 7.70(1H, dd, J = 8, 2 Hz), 8.02(1H, t, J = 2 Hz), 8.11(1H, s), 8.47(1H, s); ESI+: 406/408 |
| 141 | 1 | NMR1: 1.58-1.84(8H, m), 1.94-2.12(4H, m), 2.22-2.46(6H, m), 3.42-3.68(4H, m), 5.12(1H, s), 7.68(1H, s); ESI+: 432 |
| 142 | 4 | NMR1: 1.09-1.19(2H, m), 1.51(1H, d, J = 9 Hz), 1.67(1H, d, J = 9 Hz), 1.87-1.98(2H, m), 3.19-3.29(4H, m), 3.56-3.61(2H, m), 3.8-3.98(4H, m), 7.06-7.11(1H, m), 7.28-7.39(2H, m), 7.73(1H, d, J = 2 Hz), 8.14(1H, brs); ESI+: 434 |
| 143 | 4 | NMR1: 1.30(4H, d, J = 7.4 Hz), 1.80(4H, d, J = 7.4 Hz), 3.15-3.25(3H, m), 3.29-3.41(3H, m), 3.68-3.77(2H, m), 4.04-4.14(2H, m), 6.63-6.71(1H, m), 6.77-6.88(2H, m), 7.27(1H, q, J = 7.9 Hz), 8.37(1H, s), 8.51(1H, brs); ESI+: 430 |
| 144 | 4 | NMR1: 1.31(4H, d, J = 8.8 Hz), 1.79(4H, d, J = 7.6 Hz), 2.26(3H, s), 3.15-3.26(3H, m), 3.26-3.37(2H, m), 3.45(1H, s), 3.68-3.76(2H, m), 4.03-4.13(2H, m), 6.78(1H, d, J = 7.6 Hz), 6.87-6.94(2H, m), 7.18(1H, t, J = 7.6 Hz), 8.26(1H, s); ESI+: 426 |
| 145 | 4 | NMR1: 1.23-1.38(4H, m), 1.42-1.60(6H, m), 1.73-1.95(10H, m), 2.22-2.30(2H, m), 3.09-3.26(3H, m), 3.28-3.43(2H, m), 3.61-3.76(3H, m), 4.05-4.19(2H, m), 8.43(1H, s); ESI+: 486 |
| 146 | 4 | NMR1: 1.13(6H, s), 1.30(4H, d, J = 6.8 Hz), 1.44-1.48(2H, m), 1.49-1.58(4H, m), 1.75-1.91(10H, m), 2.23-2.28(2H, m), 3.26(2H, d, J = 6.4 Hz), 3.62(1H, brs), 4.22(1H, brs), 8.41-8.55(2H, m); ESI+: 440 |
| 147-1 | 5 | NMR1: 1.11-1.21(2H, m), 1.56(1H, d, J = 9.0 Hz), 1.71(1H, d, J = 9.0 Hz), 1.91-2.00(2H, m), 2.28(3H, s), 3.22-3.33(4H, m), 3.60(1H, brs), 3.69(1H, brs), 3.79-4.14(4H, brs), 6.83(1H, d, J = 7.5 Hz), 6.94-7.01(2H, m), 7.21(1H, dd, J = 7.5, 7.4 Hz), 8.15(1H, s), 8.43(1H, brs); ESI+: 412; [a]D: −130.9(c = 0.555, MeOH) |
| 147-2 | 5 | NMR1: 1.10-1.21(2H, m), 1.54(1H, d, J = 9.2 Hz), 1.69(1H, d, J = 9.2 Hz), 1.89-2.00(2H, m), 2.28(3H, s), 3.20-3.32(4H, m), 3.60(1H, brs), 3.66(1H, brs), 3.78-4.14(4H, brs), 6.81(1H, d, J = 7.5 Hz), 6.92-6.99(2H, m), 7.20(1H, dd, J = 7.8, 7.5 Hz), 8.15(1H, s), 8.36(1H, brs); ESI+: 412; [a]D: +132.20(c = 0.295, MeOH) |

TABLE 105

| Ex | Syn | Data |
|---|---|---|
| 148 | 4 | NMR1: 1.03-1.13(2H, m), 1.46-1.53(1H, m), 1.61-1.69(1H, m), 1.77-1.86(2H, m), 1.87-1.99(5H, m), 2.01-2.12(2H, m), 2.22-2.36(3H, m), 2.36-2.50(2H, m), 2.45-2.52(1H, m), 3.48(1H, s), 3.85(1H, s), 3.93(4H, brs), 4.30(4H, brs), 8.03(1H, s); ESI+: 492 |
| 149 | 4 | NMR1: 1.21-1.37(4H, m), 1.68-1.87(6H, m), 1.91-2.01(2H, m), 2.03-2.13(3H, m), 2.25-2.38(3H, m), 2.38-2.47(2H, m), 2.47-2.54(1H, m), 3.09(1H, s), 3.29(4H, brs), 3.56(1H, s), 3.82(4H, brs), 8.11(1H, s); ESI+: 506 |
| 150 | 4 | NMR1: 1.05-1.13(2H, m), 1.44-1.54(2H, m), 1.55-1.63(2H, m), 1.64-1.78(4H, m), 1.87-2.03(6H, m), 2.06-2.15(2H, m), 2.26(2H, brs), 3.50(1H, s), 3.64-4.03(9H, brm), 7.98(1H, s); ESI+: 472; [a]D: −69.9(c = 0.505, MeOH) |
| 151 | 4 | NMR1: 1.08-1.25(2H, m), 1.58(1H, d, J = 8.9 Hz), 1.73(1H, d, J = 8.9 Hz), 1.92-2.04(2H, m), 3.29(4H, brs), 3.54(1H, s), 3.90(1H, s), 3.95(4H, brs), 6.88(1H, dd, J = 8.0, 9.0 Hz), 7.39(1H, dd, J = 8.0, 15.2 Hz), 7.47(1H, d, J = 9.0 Hz), 7.73(1H, d, J = 11.9 Hz ), 8.10(1H, s), 9.35(1H, brs); ESI+: 416; [a]D: −84.8(c = 0.42, MeOH) |
| 152-1 | 4 | NMR1:1.10-1.21(2H, m), 1.57(1H, d, J = 9.2 Hz), 1.73(1H, d, J = 9.2 Hz), 1.91-2.02(2H, m), 3.28(4H, brs), 3.61(1H, brs), 3.68(1H, brs), 3.77-4.16(4H, m), 6.75(1H, dt, J = 2.3, 8.0 Hz), 6.89-6.99(2H, m), 7.32(1H, q, J = 7.6 Hz), 8.27(1H, s), 8.70(1H, brs); ESI+: 416; [a]D: −130.8(c = 0.500, MeOH) |
| 152-2 | 4 | NMR1: 1.10-1.21(2H, m), 1.56(1H, d, J = 9.2 Hz), 1.71(1H, d, J = 9.2 Hz), 1.90-2.01(2H, m), 3.19-3.36(4H, m), 3.61(1H, brs), 3.65(1H, brs), 3.78-4.17(4H, m), 6.73(1H, dt, J = 8.2, 2.1 Hz), 6.90, (1H, dt, J = 11.4, 2.2 Hz), 6.94(1H, |

TABLE 105-continued

| Ex | Syn | Data |
|---|---|---|
| | | dd, J = 7.6, 1.6 Hz), 7.31(1H, q, J = 7.7 Hz), 8.26(1H, s), 8.62(1H, brs); ESI+: 416; [a]D: +120.00(c = 0.310, MeOH) |
| 153-1 | 4 | NMR1: 1.11-1.19(2H, m), 1.55(1H, d, J = 9.1 Hz), 1.70(1H, d, J = 9.1 Hz), 1.91-1.99(2H, m), 3.26(4H, brs), 3.60(1H, brs), 3.67(1H, brs), 3.73(3H, s), 3.78-4.64(4H, m), 6.56(1H, dd, J = 1.9, 8.1 Hz), 6.68(1H, t, J = 2.2 Hz), 6.70-6.75(1H, m), 7.21(1H, t, J = 8.1 Hz), 8.2(1H, s), 8.40(1H, brs); ESI+: 428; [a]D: −136.0(c = 0.520, MeOH) |
| 153-2 | 4 | NMR1: 1.11-1.19(2H, m), 1.55(1H, d, J = 9 Hz), 1.69(1H, d, J = 9 Hz), 1.91-1.99(2H, m), 3.2-3.3(4H, m), 3.61(1H, brs), 3.66(1H, brs), 3.73(3H, s), 3.85-4.16(4H, m), 6.55(1H, dd, J = 2.1, 8.1 Hz), 6.68(1H, t, J = 2.1 Hz), 6.70-6.75(1H, m), 7.21(1H, t, J = 8.1 Hz), 8.2(1H, s), 8.39(1H, brs); ESI+: 428; [a]D: +119.85(c = 0.30, MeOH) |
| 154 | 4 | NMR1: 1.29(4H, d, J = 7.6 Hz), 1.79(4H, d, J = 7.6 Hz), 3.13-3.23(3H, m), 3.27-3.36(3H, m), 3.68-3.75(2H, m), 4.03-4.13 (2H, m), 6.97-7.03(1H, m), 7.15(1H, dd, J = 6.4, 2.8 Hz), 7.30(1H, t, J = 7.6 Hz), 8.29(1H, s), 8.36(1H, brs); ESI+: 464/466 |
| 155 | 1 | NMR1: 1.58-1.86(8H, m), 1.95-2.13(4H, m), 2.22-2.50 (6H, m), 3.09-3.28(2H, m), 3.62-3.92(2H, m), 5.15(1H, s), 7.84(1H, s) ESI+: 480 |

TABLE 106

| Ex | Syn | Data |
|---|---|---|
| 156 | 1 | NMR1: 1.41-1.82(18H, m), 2.31(2H, t, J = 6.3 Hz), 3.08-3.92 (10H, m), 4.10-4.22(1H, m), 5.52(1H, d, J = 7.8 Hz), 7.81(1H, s); ESI+: 420 |
| 157 | 4 | NMR1: 1.17-1.35(4H, m), 1.71-1.86(4H, m), 3.15-3.35(5H, m), 3.42(1H, brs), 3.67-3.77(5H, m), 4.04-4.1(2H, m), 6.5(1H, dd, J = 2.1, 8.2 Hz), 6.6-6.65(2H, m), 7.17(1H, t, J = 8.2 Hz), 8.26(1H, brs), 8.31(1H, s); ESI+: 442 |
| 158-1 | 4 | NMR1: 1.07-1.2(2H, m), 1.42-1.62(8H, m), 1.62-1.71 (1H, m), 1.78-1.87(7H, m), 1.9-2(2H, m), 2.21-2.27(2H, m), 3.2-3.34(4H, m), 3.55-4.1(6H, m), 8.12(1H, s); ESI+: 472 |
| 158-2 | 4 | NMR1: 1.07-1.2(2H, m), 1.42-1.62(8H, m), 1.65-1.73(1H, m), 1.78-1.87(7H, m), 1.9-2(2H, m), 2.21-2.27(2H, m), 3.2-3.34(4H, m), 3.55-4.1(6H, m), 8.15(1H, s); ESI+: 472 |
| 159 | 4 | NMR1: 1.07-1.18(1H, m), 1.20-1.30(1H, m), 1.58(1H, d, J = 9.0 Hz), 1.75(1H, d, J = 9.0 Hz), 1.94-2.07(2H, m), 3.29 (4H, brs), 3.56(1H, s), 3.87(1H, s), 3.88(3H, s), 3.93 (4H, brs), 7.14-7.23(1H, m), 7.25-7.34(1H, m), 7.43-7.51(1H, m), 8.02(1H, s), 9.78(1H, brs); ESI+: 446; [a]D: −69.6(c = 0.51, MeOH) |
| 160 | 4 | NMR1: 1.09-1.17(1H, m), 1.19-1.28(1H, m), 1.58(1H, d, J = 9.0 Hz), 1.75(1H, d, J = 9.0 Hz), 1.92-2.06(2H, m), 2.30(3H, s), 3.29(4H, brs), 3.55(1H, s), 3.85(1H, s), 3.93 (4H, brs), 7.21-7.29(1H, m), 7.39-7.45(1H, m), 7.46-7.51(1H, m), 8.00(1H, s), 9.84(1H, brs); ESI+: 430; [a]D: −75.6(c = 0.55, MeOH) |
| 161 | 4 | NMR1: 1.09-1.22(2H, m), 1.56(1H, d, J = 9.0 Hz), 1.70 (1H, d, J = 9.0 Hz), 1.91-2.01(2H, m), 2.22(3H, s), 3.21-3.35(4H, m), 3.60(1H, brs), 3.68(1H, brs), 3.77-4.16(4H, m), 7.00-7.06(1H, m), 7.08-7.15(2H, m), 8.06(1H, s), 8.43(1H, brs); ESI+: 430 |
| 162 | 4 | NMR1: 1.11-1.21(2H, m), 1.57(1H, d, J = 9.0 Hz), 1.71 (1H, d, J = 9.0 Hz), 1.92-2.01(2H, m), 3.21-3.33(4H, m), 3.60(1H, brs), 3.70(1H, brs), 3.78-4.14(4H, m), 3.82(3H, s), 6.70-6.76(1H, m), 6.97(1H, dd, J = 7.6, 2.6 Hz), 7.17(1H, dd, J =11.2, 8.6 Hz), 8.14(1H, s), 8.49(1H, brs); ESI+: 446 |
| 163-1 | 5 | NMR1: 1.09-1.21(2H, m), 1.55(1H, d, J = 9.0 Hz), 1.69 (1H, d, J = 9.0 Hz), 1.89-52.00(2H, m), 3.18-3.34(4H, m), 3.57 (1H, brs), 3.61(1H, brs), 3.77-4.13(4H, m), 7.37-7.46 (3H, m), 8.20(1H, s), 8.64(1H, brs); FAB+: 484 |
| 163-2 | 5 | NMR1: 1.09-1.22(2H, m), 1.55(1H, d, J = 9.0 Hz), 1.69(1H, d, J = 9.0 Hz), 1.89-52.00(2H, m), 3.18-3.34(4H, m), 3.56 (1H, brs), 3.61(1H, brs), 3.77-4.32(4H, m), 7.37-7.45(3H, m), 8.20(1H, s), 8.62(1H, brs); FAB+: 484 |

TABLE 107

| Ex | Syn | Data |
|---|---|---|
| 164 | 4 | NMR1: 1.3(4H, d, J = 9.6 Hz), 1.78(4H, d, J = 8.4 Hz), 2.26 (3H, d, J = 1.6 Hz), 3.18(3H, brs), 3.31(2H, brs), 3.4(1H, brs), 3.7(2H, brs), 4.08(2H, brs), 6.9(2H, q, J = 7.3 Hz), 7(1H, t, J = 7.6 Hz), 7.98(1H, d, J = 1.6 Hz), 8.07(1H, brs); ESI+: 444; Temp: 146 |
| 165 | 4 | NMR1: 1.31(4H, d, J = 8.4 Hz), 1.79(4H, d, J = 8.4 Hz), 2.23 (3H, s), 3.11-3.47(6H, m), 3.7(2H, brs), 4.08(2H, brs), 6.81-6.89(1H, m), 6.92(1H, d, J = 8 Hz), 7.14(1H, dd, J = 8, 11.2 Hz), 7.97(1H, d, J = 2 Hz), 8.15(1H, brs); ESI+: 444; Temp: 178.7 |
| 166 | 4 | NMR1: 1.22-1.39(4H, m), 1.72-1.90(4H, m), 2.21(3H, s), 3.13-3.39(5H, m), 3.48(1H, brs), 3.71(2H, brs), 4.08(2H, brs), 6.93-7.00(1H, m), 7.05(1H, dd, J = 6.8, 2.4 Hz), 7.09(1H, t, J = 9.1 Hz), 8.17(1H, s), 8.29(1H, brs); ESI+: 444 |
| 167 | 4 | NMR1: 1.23-1.38(4H, m), 1.73-1.86(4H, m), 2.26(3H, s), 3.15-3.27(3H, m), 3.27-3.42(3H, m), 3.72(2H, brs), 4.08(2H, brs), 6.96(1H, dd, J = 8.4, 2.2 Hz), 7.09(1H, d, J = 2.2 Hz), 7.24(1H, d, J = 8.4 Hz), 8.29(1H, s), 8.40(1H, brs); ESI+: 460/462; Temp: 147.3 |
| 168 | 4 | NMR1: 1.07-1.16(1H, m), 1.18-1.27(1H, m), 1.58(1H, d, J = 9.0 Hz), 1.73(1H, d, J = 9.0 Hz), 1.91-2.06(2H, m), 3.29 (4H, brs), 3.55 (1H, s), 3.90(1H, s), 3.94(4H, brs), 7.40-7.48 (1H, m), 7.65-7.71(1H, m), 8.07-8.13(1H, m), 8.08(1H, s), 9.69(1H, brs); ESI+: 494; [a]D: −67.5(c = 0.48, MeOH) |
| 169 | 4 | NMR1: 1.07-1.16(1H, m), 1.17-1.26(1H, m), 1.58(1H, d, J = 9.0 Hz), 1.73(1H, d, J = 9.0 Hz), 1.91-2.04(2H, m), 3.29 (4H, brs), 3.54 (1H, s), 3.89(1H, s), 3.94(4H, brs), 7.28(1H, d, J = 7.8 Hz), 7.35(1H, dd, J = 7.7, 7.8 Hz), 7.66(1H, d, J = 7.7 Hz), 8.00(1H, s), 8.11(1H, s), 9.57(1H, brs); ESI+: 476; [a]D: −72.7(c = 0.44, MeOH) |
| 170 | 4 | NMR1: 1.06-1.15(1H, m), 1.16-1.25(1H, m), 1.57(1H, d, J = 8.9 Hz), 1.72(1H, dJ = 8.9 Hz), 1.92-2.05(2H, m), 3.29(4H, brs), 3.54(1H, s), 3.92(1H, s), 3.94(4H, brs), 7.60 (1H, d, J = 8.9 Hz), 7.70(1H, dd, J = 2.5, 8.9 Hz), 8.13(1H, s), 8.14(1H, d, J = 2.5 Hz), 9.47(1H, brs); ESI+: 466; [a]D: −74.4(c = 0.48, MeOH) |
| 171 | 4 | NMR1: 1.07-1.16(1H, m), 1.18-1.28(1H, m), 1.58(1H, dJ = 9.0 Hz), 1.72(1H, dJ = 9.0 Hz), 1.92-2.05(2H, m), 2.36(3H, s), 3.29(4H, brs), 3.55(1H, s), 3.89(1H, s), 3.94(4H, brs), 7.40 (1H, d, J = 8.3 Hz), 7.48(1H, d, J = 1.8, 8.3 Hz), 7.79(1H, s), 8.06(1H, s), 9.80(1H, brs); ESI+: 446; [a]D: −82.3(c = 0.46, MeOH) |
| 172 | 4 | NMR1: 1.06-1.25(2H, m), 1.57(1H, d, J = 8.9 Hz), 1.72(1H, d, J = 8.9 Hz), 1.92-2.05(2H, m), 3.28(4H, brs), 3.53 (1H, s), 3.92 (1H, s), 3.94(4H, brs), 7.50-7.58(2H, m), 7.96-8.04(1H, m), 8.13(1H, s), 9.39(1H, brs); ESI+: 450; [a]D: −79.1 (c = 0.54, MeOH) |

TABLE 108

| Ex | Syn | Data |
|---|---|---|
| 173 | 4 | NMR1: 1.23-1.46(4H, m), 1.75-1.91(4H, m), 3.15(1H, s), 3.35(4H, brs), 3.72(1H, s), 3.78(4H, brs), 7.41-7.49 (1H, m), 7.64(1H, ddd, J = 2.8, 4.2, 8.8 Hz), 8.04(1H, dd, J = 2.8, 6.2 Hz), 8.11(1H, s), 9.65(1H, brs); ESI+: 508 |
| 174 | 4 | NMR1: 1.25-1.45(4H, m), 1.75-1.90(4H, m), 3.14(1H, s), 3.34(4H, brs), 3.69(1H, s), 3.79(4H, brs), 7.28(1H, d, J = 7.7 Hz), 7.35(1H, dd, J = 7.7, 8.1 Hz), 7.63(1H, d, J = 8.1 Hz), 7.95(1H, s), 8.14(1H, s), 9.40(1H, brs); ESI+: 490 |
| 175 | 4 | NMR1: 1.23-1.45 (4H, m), 1.74-1.90(4H, m), 3.13(1H, s), 3.34(4H, brs), 3.68(1H, s), 3.78(4H, brs), 7.59(1H, d, J = 8.8 Hz), 7.68(1H, dd, J = 2.4, 8.8 Hz), 8.09(1H, d, J = 2.4 Hz), 8.16(1H, s), 9.28(1H, brs); ESI+: 480 |
| 176 | 4 | NMR1: 1.24-1.45(4H, m), 1.76-1.91(4H, m), 2.35(3H, s), 3.14(1H, s), 3.33 (4H, brs), 3.67(1H, s), 3.79(4H, brs), 7.37(1H, d, J = 8.2 Hz), 7.5(1H, dd, J = 1.4, 8.2 Hz), 7.81(1H, s), 8.09 (1H, s), 9.24(1H, brs); ESI+: 460 |
| 177 | 4 | NMR1: 1.24-1.43 (4H, m), 1.74-1.91(4H, m), 3.13(1H, s), 3.34 (4H, brs), 3.67(1H, s), 3.77(4H, brs), 7.50-7.55(2H, m), 7.91-7.97(1H, m), 8.16(1H, s), 9.18(1H, brs); ESI+: 464 |
| 178 | 4 | NMR1: 1.24-1.46(4H, m), 1.79-1.91(4H, m), 2.30(3H, s), 3.16 (1H, s), 3.35(4H, brs), 3.73(1H, s), 3.79(4H, brs), 7.22-7.31 (1H, m), 7.36-7.44(1H, m), 7.47(1H, dd, J = 2.2, 6.8 Hz), 8.02(1H, s), 9.71(1H, brs); ESI+: 444 |

TABLE 108-continued

| Ex | Syn | Data |
|---|---|---|
| 179 | 4 | NMR1: 1.24-1.43(4H, m), 1.74-1.90(4H, m), 3.13(1H, s), 3.34 (4H, brs), 3.67(1H, s), 3.77(4H, brs), 6.96-7.02(1H, m), 7.65-7.68(1H, m), 7.70(1H, d, J = 2 Hz), 8.21(1H, s), 9.25(1H, brs); ESI+: 464; Temp: 162.3 |
| 180 | 4 | NMR1: 1.24-1.41(4H, m), 1.76-1.89(4H, m), 3.13(1H, s), 3.33(4H, brs), 3.67(1H, s), 3.78(4H, brs), 7.18(1H, s), 7.85 (1H, s), 7.86(1H, s), 8.22(1H, s), 9.30(1H, brs); ESI+: 480 |

INDUSTRIAL APPLICABILITY

The compound as an active ingredient of the medication of the present invention has potent agonist action on a cannabinoid receptor type 2 and has excellent pharmacological action based on the agonist action. Accordingly, the pharmaceutical composition of the present invention can be used as an agent for preventing or treating cannabinoid receptor type 2-related diseases, such as inflammatory disease and pain.

The invention claimed is:

1. A compound of Formula (I) or a salt thereof,

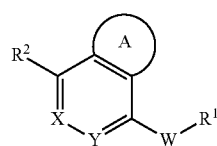

(I)

wherein,

X represents CH or C-lower alkyl,

Y represents N,

W represents —NH—, —N(lower alkyl)-, —O—, —S—, —S(O)—, or —S(O)$_2$—,

R$^1$ represents cycloalkyl which may be substituted, aryl which may be substituted, an aromatic heterocycle which may be substituted, or a non-aromatic heterocycle which may be substituted, R$^2$ represents —Z—NR$^3$R$^4$ or —Z-nitrogen-containing non-aromatic heterocyclic which is bonded to Z at a nitrogen atom, which may be substituted, A portion represents a group represented by Formula (II), (III), or (IV),

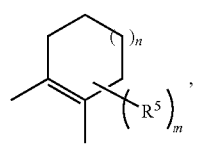

(II)

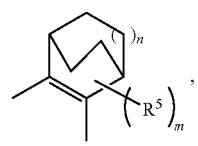

(III)

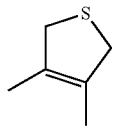

(IV)

R$^3$ represents H or lower alkyl,

R$^4$ represents lower alkyl substituted with one or more groups selected from the group consisting of —OH, —O-lower alkyl, halogen, cycloalkyl, cyano, —S-lower alkyl, —S(O)-lower alkyl, —S(O)$_2$-lower alkyl, and —O-halogeno-lower alkyl, each R$^5$ is the same or different and independently represents lower alkyl or halogen, Z represents —C(O)—, —CH$_2$—, or —S(O)$_2$—, m represents an integer of 0 to 10, and n represents an integer of 0 to 2.

2. The compound or salt thereof according to claim 1, wherein R$^1$ represents cycloalkyl which may be substituted with one or more substituents selected from D group, aryl which may be substituted with one or more substituents selected from D group, an aromatic heterocycle which may be substituted with one or more substituents selected from D group, or a non-aromatic heterocycle which may be substituted with one or more substituents selected from D group, R$^2$ represents —Z—NR$^3$R$^4$ or —Z-nitrogen-containing non-aromatic heterocuclic which is bonded to Z at a nitrogen atom, which may be substituted with one or more substituents selected from D group, and D group includes (1) halogen, (2) —OH, —O-lower alkyl, —O-halogeno-lower alkyl and —SH, (3) cyano and nitro, (4) cycloalkyl, —O-cycloalkyl, and —C(O)-cycloalkyl, which may be respectively substituted with one or more groups selected from the group consisting of lower alkyl, halogen, —OH, —O-lower alkyl, —O-halogeno-lower alkyl, and halogeno-lower alkyl, (5) aryl, —O-aryl, and —C(O)-aryl, which may be respectively substituted with one or more groups selected from the group consisting of lower alkyl, halogen, —OH, —O-lower alkyl, —O-halogeno-lower alkyl, and halogeno-lower alkyl, (6) an aromatic heterocycle, —O-aromatic heterocycle, and —C(O)-aromatic heterocycle, which may be respectively substituted with one or more groups selected from the group consisting of lower alkyl, halogen, —OH, —O-lower alkyl, —O-halogeno-lower alkyl, and halogeno-lower alkyl, (7) a non-aromatic heterocycle, —O-non-aromatic heterocycle, and —C(O)-non-aromatic heterocycle, which may be respectively substituted with one or more groups selected from the group consisting of lower alkyl, halogen, —OH, —O-lower alkyl, —O-halogeno-lower alkyl, and halogeno-lower alkyl, (8) —C(O)-lower alkyl, —C(O)O-lower alkyl, —NH—C(O)-lower alkyl, —NH-lower alkyl, —N(lower alkyl)$_2$, —CONH-lower alkyl, and CON(lower alkyl)$_2$, in which lower alkyl moieties may be respectively substituted with one or more groups selected from the group consisting of halogen, —OH, —O-lower alkyl, and —O-halogeno-lower alkyl, (9) NH$_2$ and CONH$_2$,

(10) —S-lower alkyl, —S(O)-lower alkyl, and —S(O)₂-lower alkyl, in which lower alkyl moieties may be respectively substituted with one or more groups selected from the group consisting of halogen, —OH, —O-lower alkyl, and —O-halogeno-lower alkyl, and

(11) lower alkyl and —O-lower alkyl which may be respectively substituted with group(s) selected from substituents described in the above sections (1) to (10).

3. The compound or salt thereof according to claim 2, wherein R² represents a group represented by Formula (V), (VI), or (VII):

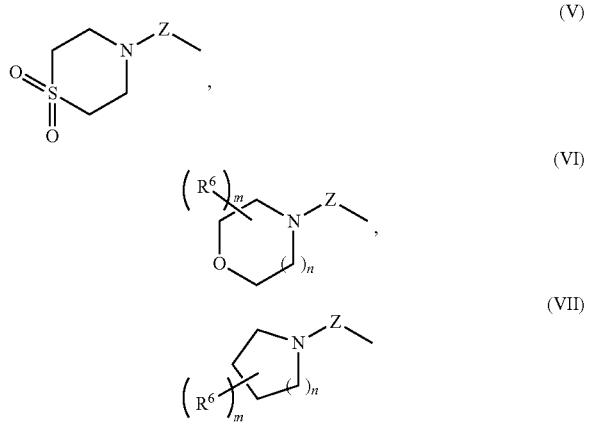

wherein each R⁶ is the same or different and independently represents lower alkyl which may be substituted with one or more groups selected from —OH, halogen, cycloalkyl, cyano, —S-lower alkyl, —S(O)-lower alkyl, and —S(O)₂-lower alkyl, —OH, —O-lower alkyl, halogen, cycloalkyl, cyano, —O-lower alkylene-OH, —S-lower alkyl, —S(O)-lower alkyl, —S(O)₂-lower alkyl, or —O-halogeno-lower alkyl.

4. The compound or salt thereof according to claim 3, wherein R² represents a group represented by Formula (V) or (VI), Z represents —C(O)—, W represents —NH or —O—, and A portion represents a group represented by Formula (II) or (III).

5. The compound or salt thereof according to claim 4, wherein X represents CH, Y represents N, R¹ represents i) cycloalkyl which may be substituted with one or more groups selected from the group consisting of lower alkyl, halogen, and OH, or ii) aryl which may be substituted with one or more groups selected from the group consisting of lower alkyl, halogen, halogeno-lower alkyl, and —O-halogeno-lower alkyl, A portion represents a group represented by Formula (II) in which n represents 0 or 1 and m represents 0, n in Formula (VI) represents 1 or 2, and m in Formula (VI) represents 0.

6. The compound or salt thereof according to claim 5, wherein n in Formula (II) represents 0, n in Formula (VI) represents 1, R¹ represents phenyl which may be substituted with one or more groups selected from the group consisting of halogen, —O-halogeno-lower alkyl, and halogeno-lower alkyl.

7. The compound or salt thereof according to claim 4, wherein X represents CH, Y represents N, R¹ represents i) cycloalkyl which may be substituted with one or more groups selected from the group consisting of lower alkyl, halogen, and OH, ii) aryl which may be substituted with one or more groups selected from the group consisting of lower alkyl, halogen, halogeno-lower alkyl, —O-lower alkyl, and —O-halogeno-lower alkyl, or iii) a non-aromatic heterocycle which may be substituted with one or more groups selected from the group consisting of lower alkyl, halogen, and —OH, A portion represents a group represented by Formula (III) in which n represents 0 or 1 and m represents 0, n in Formula (VI) represents 1 or 2, and m in Formula (VI) represents 0.

8. The compound or salt thereof according to claim 7, wherein R¹ represents phenyl which may be substituted with one or more groups selected from the group consisting of halogen, —O-halogeno-lower alkyl, and halogeno-lower alkyl, R² represents Formula (V), and W represents —NH—.

9. The compound or salt thereof according to claim 1, which is a compound selected from the group consisting of:

{1-[(3-chlorophenyl)amino]-5,6,7,8-tetrahydroisoquinolin-4-yl}(1,1-dioxidothiomorpholin-4-yl)methanone, morpholin-4-yl(1-{[3-(trifluoromethoxy)phenyl]amino}-5,6,7,8-tetrahydroisoquinolin-4-yl)methanone, (1,1-dioxidothiomorpholin-4-yl){1-[3-(trifluoromethyl)phenoxy]-5,6,7,8-tetrahydroisoquinolin-4-yl}methanone, {1-[(3-chlorophenyl)amino]-5,6,7,8-tetrahydro-5,8-ethanoisoquinolin-4-yl}(1,1-dioxidothiomorpholin-4-yl)methanone, (1,1-dioxidothiomorpholin-4-yl)(1-{[3-(trifluoromethyl)phenyl]amino}-5,6,7,8-tetrahydro-5,8-ethanoisoquinolin-4-yl)methanone, {1-[(3-chloro-4-fluorophenyl)amino]-5,6,7,8-tetrahydro-5,8-methanoisoquinolin-4-yl}(1,1-dioxidothiomorpholin-4-yl)methanone, (1,1-dioxidothiomorpholin-4-yl)(1-{[3-(trifluoromethoxy)phenyl]amino}-5,6,7,8-tetrahydro-5,8-methanoisoquinolin-4-yl)methanone, (1,1-dioxidothiomorpholin-4-yl)(1-{[4-fluoro-3-(trifluoromethyl)phenyl]amino}-5,6,7,8-tetrahydro-5,8-methanoisoquinolin-4-yl)methanone, {1-[(3-chlorophenyl)amino]-5,6,7,8-tetrahydro-5,8-methanoisoquinolin-4-yl}(1,1-dioxidothiomorpholin-4-yl)methanone, {1-[(3,4-difluorophenyl)amino]-5,6,7,8-tetrahydro-5,8-ethanoisoquinolin-4-yl}(1,1-dioxidothiomorpholin-4-yl)methanone, {1-[(3-chloro-5-fluorophenyl)amino]-5,6,7,8-tetrahydro-5,8-ethanoisoquinolin-4-yl}(1,1-dioxidothiomorpholin-4-yl)methanone, or a salt of said compound.

10. A pharmaceutical composition, comprising a compound or salt thereof according to claim 1 and a pharmaceutically acceptable excipient.

11. A method of treating pain of arthrosis deformans, comprising administering an effective amount of a compound or pharmaceutically acceptable salt thereof according to claim 1 to a patient in need thereof.

12. The compound or salt thereof according to claim 9, which is:

{1-[(3-chloro-4-fluorophenyl)amino]-5,6,7,8-tetrahydro-5,8-methanoisoquinolin-4-yl}(1,1-dioxidothiomorpholin-4-yl)methanone.

13. The compound or salt thereof according to claim 9, which is:

(1,1-dioxidothiomorpholin-4-yl)(1-{[3-(trifluoromethoxy)phenyl]amino}-5,6,7,8-tetrahydro-5,8-methanoisoquinolin-4-yl)methanone.

14. The compound or salt thereof according to claim 9, which is:
(1,1-dioxidothiomorpholin-4-yl)(1-{[4-fluoro-3-(trifluoromethyl)phenyl]amino}-5,6,7,8-tetrahydro-5,8-methanoisoquinolin-4-yl)methanone.

15. The compound or salt thereof according to claim 9, which is:
{1-[(3,4-difluorophenyl)amino]-5,6,7,8-tetrahydro-5,8-ethanoisoquinolin-4-yl}(1,1-dioxidothiomorpholin-4-yl)methanone.

16. The compound or salt thereof according to claim 9, which is:
(−)-{1-[(3-chloro-4-fluorophenyl)amino]-5,6,7,8-tetrahydro-5,8-methanoisoquinolin-4-yl}(1,1-dioxidothiomorpholin-4-yl)methanone monohydrochloride.

17. The compound or salt thereof according to claim 13, which is:
(−)-(1,1-dioxidothiomorpholin-4-yl)(1-{[3-(trifluoromethoxy)phenyl]amino}-5,6,7,8-tetrahydro-5,8-methanoisoquinolin-4-yl)methanone monohydrochloride.

18. The compound or salt thereof according to claim 13, which is:
(−)-(1,1-dioxidothiomorpholin-4-yl)(1-{[4-fluoro-3-(trifluoromethyl)phenyl]amino}-5,6,7,8-tetrahydro-5,8-methanoisoquinolin-4-yl)methanone monohydrochloride.

19. The compound or salt thereof according to claim 9, which is:
{1-[(3,4-difluorophenyl)amino]-5,6,7,8-tetrahydro-5,8-ethanoisoquinolin-4-yl}(1,1-dioxidothiomorpholin-4-yl)methanone monohydrochloride.

20. A method of treating chronic lower back pain, comprising administering an effective amount of a compound or pharmaceutically acceptable salt thereof according to claim 1 to a patient in need thereof.

* * * * *